US008153157B2

United States Patent
Obae et al.

(10) Patent No.: US 8,153,157 B2
(45) Date of Patent: Apr. 10, 2012

(54) POROUS CELLULOSE AGGREGATE AND MOLDING COMPOSITION THEREOF

(75) Inventors: Kazuhiro Obae, Tokyo (JP); Hideki Amakawa, Tokyo (JP); Ichiro Ibuki, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 1113 days.

(21) Appl. No.: 11/918,979

(22) PCT Filed: Apr. 21, 2006

(86) PCT No.: PCT/JP2006/308414
§ 371 (c)(1),
(2), (4) Date: Oct. 22, 2007

(87) PCT Pub. No.: WO2006/115198
PCT Pub. Date: Nov. 2, 2006

(65) Prior Publication Data
US 2009/0022791 A1 Jan. 22, 2009

(30) Foreign Application Priority Data

Apr. 22, 2005 (JP) ................... 2005-124477

(51) Int. Cl.
*A61K 9/14* (2006.01)
(52) U.S. Cl. ....................................... 424/489
(58) Field of Classification Search ............... None
See application file for complete search history.

(56) References Cited

U.S. PATENT DOCUMENTS

| 4,159,345 A | 6/1979 | Takeo et al. |
| 5,574,150 A * | 11/1996 | Yaginuma et al. ............ 536/56 |
| 2004/0043964 A1 | 3/2004 | Gomi et al. |

FOREIGN PATENT DOCUMENTS

| JP | 53-127553 | 11/1978 |
| JP | 63-90501 | 4/1988 |
| JP | 2-208 | 1/1990 |
| JP | 2-84401 | 3/1990 |
| JP | 6-316535 | 11/1994 |
| JP | 9-132601 | 5/1997 |
| JP | 2001-122973 | 5/2001 |
| JP | 2005-232260 | 9/2005 |
| WO | 94/23703 | 10/1994 |
| WO | 2005/073286 | 8/2005 |

OTHER PUBLICATIONS

English language version of the International Search Report (PCT/ISA/210) of the International Application PCT/JP2006/308414 (mailed on Jul. 18, 2006).
European Search Report issued on Feb. 11, 2010 in corresponding European Patent Application 06745545.1.

* cited by examiner

*Primary Examiner* — Susan Tran
(74) *Attorney, Agent, or Firm* — Staas & Halsey LLP

(57) ABSTRACT

A porous cellulose aggregate characterized by having a secondary aggregate structure resulting from aggregation of primary cellulose particles, having a pore volume within a particle of 0.265 to 2.625 cm$^3$/g, containing I-type crystals and having an average particle size of over 30 to 250 μm, a specific surface area of 0.1 to less than 20 m$^2$/g, a repose angle of 25° to less than 44° and a swelling degree of 5% or more, and characterized by having the property of disintegrating in water.

4 Claims, 4 Drawing Sheets

POROUS CELLULOSE AGGREGATE AND MOLDING COMPOSITION THEREOF

CROSS REFERENCE TO RELATED APPLICATIONS

This application claims the benefit under 35 U.S.C. Section 371, of PCT International Application Number PCT/JP2006/308414, filed Apr. 21, 2006 and Japanese Application No. 2005-124477, filed Apr. 22, 2005 in Japan, the contents of which are incorporated herein by reference.

TECHNICAL FIELD

The present invention relates to a porous cellulose aggregate that is useful mainly as an excipient in the field of chemical engineering, in particular, of pharmaceuticals and of foods, and a compacting (molding) composition thereof.

BACKGROUND ART

In the fields of pharmaceuticals, foods and other chemical engineering and the like, it has been a general practice conventionally to prepare a molded body containing an active ingredient using cellulose particles such as crystalline cellulose, cellulose powder and the like as an excipient, and for these cellulose particles, good compactibility, fluidity and disintegration property are required.

Patent Document 1 describes a porous cellulose aggregate (corresponding to Comparative Example 15-17) having a secondary aggregate structure formed by aggregation of primary cellulose particles, the aggregate having a pore volume within a particle of 0.265 $cm^3/g$ to 2.625 $cm^3/g$, containing type I crystals, and having an average particle size of more than 30 μm and 250 μm or less, a specific surface area of 1.3-20 $m^2/g$, a repose angle of 25° or more and less than 44° and properties to disintegrate in water, and a method for producing the aforementioned porous cellulose aggregate comprising a step of drying a dispersion containing two or more groups of primary cellulose particles having a different average particle size and a liquid medium wherein the cellulose dispersion particles have an average particle size of 1 to 110 μm. Since the aforementioned porous cellulose aggregate of the Patent Document requires two or more groups of primary cellulose particles having a different average particle size, different primary cellulose particles prepared by two processes such as grinding dried acid insoluble residue of commercially available pulp and the like have to be mixed as described in Example of the Patent Document. On the other hand the porous cellulose particles of the present invention can be obtained advantageously with a single process without going through a process of grinding or the like. The porous cellulose aggregates of the present invention can be obtained by a single process by making the primary cellulose particles to have a specified range of average width and average thickness and by making flexible, thereby promoting entanglement of primary cellulose particles without being limited by the major axis of the primary cellulose particles, in other words by giving self aggregation ability thereto, and are clearly different from that described in the Patent Document in terms of the production method. In addition, because the pore size of the secondary aggregate structure of the porous cellulose particles according to the Patent Document is smaller than that of the porous cellulose aggregates of the present invention, and the swelling degree is lower in water, the disintegration property is sometimes not sufficient for making tablets for a formulation that severely requires disintegration property in the case of drugs which is insoluble in water, and even in the case of soluble drugs, when a water repellent additives such as magnesium stearate and the like has to be added to avoid problems in tablet pressing such as sticking and the like. We have investigated in detail the particle structure which controls disintegration property, and as a result confirmed again that the cellulose particles having a high swelling property have a high disintegration property, and we realized that for conventional cellulose powder, if the swelling property is high, the compactibility is not sufficient, and conversely if the compactibility is high, the swelling property is low. That is, no cellulose powder having both a high compactibility and high swelling property has been known. We searched for a method to make the particles porous while keeping the pore diameter of porous cellulose particles as large as possible and have managed to solve the aforementioned problem. That is, we found that excess aggregation can be controlled, and the inside of the particles can be made porous while keeping the pore diameter large by using primary cellulose particles having a specified range of average width and average thickness and giving self-aggregation ability thereto. For the porous cellulose aggregates of Patent Document 1, it is described that when two or more groups of cellulose particles having different particle size are mixed, and the cellulose dispersion is dried, the dispersed cellulose particles having a small average particles size enter between the dispersed cellulose particle components having a large average particle size, and for this reason an excess aggregation of the dispersed cellulose particles having the larger average particle size is inhibited, and a large pore volume is created in the secondary aggregate structure. However, since tight aggregation is formed among two or more groups of cellulose having different average particle size, the pore diameter of the porous cellulose aggregates obtained by the method particularly disclosed in the Example was measured to be small, about 1.5 μm. Since the porous cellulose aggregate of the present invention uses the single primary cellulose particles, they are not aggregated as tightly as the porous cellulose aggregate of the Patent Document and they are different in having a minimum 3 μm pore diameter. For the size of pore diameter, the Patent Document describes that a clear peak can be recognized in the range of 0.1-10 μm and the median pore diameter, which is a peak top of the pore distribution and closely related to water permeability into the particles, is preferably 0.3 μm or larger, and that although a larger median pore diameter is better, it is at most 5 μm considering its distribution. It is described that with a larger median pore diameter, there is better disintegration property, but it is speculated that in practice it is difficult to obtain a large median pore diameter of 3 μm or larger by the production method according to the Patent Document. The porous cellulose aggregates of the present invention has an advantage that porous cellulose aggregates having a large median pore diameter of 3 μm or above, which can not be obtained by the production method of the Patent Document, can be prepared by a single step without requiring mixing of the different primary cellulose particles prepared through two steps.

Patent Document 2 describes porous cellulose particles (corresponding to Comparative 6 of the present application) having a crystal structure type I, having pores of diameter of 0.1 μm or above and a porous rate of 20% or above and containing 90% by weight or above of a fraction with 350 mesh and above, which is obtained by mixing cellulose particles with the third component such as a crystalline compound or the like that is insoluble or hard to be soluble in water but soluble in an organic solvent, by granulating and drying the mixture using water or a water soluble organic solvent and then extracting/removing the third component with an organic solvent. The porous cellulose particles described in this document is entirely different from the porous cellulose aggregates of the present invention in the particle structure, because the primary cellulose particles form such a homogeneous continuous film-like tight strong cellulose wall structure that the boundaries of the particles become unclear. Although the cellulose particle in Patent Document 2 is superior in its fluidity, the tight continuous cellulose wall is impermeable to water, so that the cellulose particle was not disintegrated in water, and sometimes the rapid release of an active ingredient was impeded. Further, the cellulose particle of Patent Document 2 is poor in its plastic deformation and has insufficient compactibility while the cellulose is compressed, and furthermore since an organic solvent and a third component, which is a crystalline compound soluble in the organic solvent, are used during the production process, not only the production cost is high but also the active ingredient can be inactivated. Thus it is insufficient to be used stably as an excipient.

Patent Document 3 describes porous micro-cellulose particles (corresponding to Comparative Example 7 of the present application) having a porous structure with crystal structure type I, a specific surface area of 20 $m^2/g$ of above and a pore volume of 0.3 $cm^3$ or above for pores with diameter 0.01 μm or larger, and having an average particle size of at most 100 μm, obtained by granulating and drying fine particle natural cellulose dispersed in an organic solvent using spray-dry method. These micro-cellulose particles also have the aforementioned cellulose wall structure and are entirely different from the porous cellulose aggregates of the present invention in the particle structure. Further, the pore volume itself of the cellulose particles of Patent Document 3 is large, but since the particle structure is different from that of the porous cellulose aggregates of the present invention, water permeation into the particles is difficult, and there is a problem of the inferior disintegration property. In addition, since an organic solvent is used for these porous cellulose aggregate particles during the production process, not only is the production cost high but also the active ingredient can be inactivated because the specific surface area is too large and the interaction between the active ingredient and water is promoted. Thus it is insufficient to be used stably as an excipient.

Patent Document 4 describes cellulose powder (corresponding to Comparative Example 8 of the present application) having an average degree of polymerization of 150-375, apparent specific volume of 1.84-8.92 $cm^3/g$, a particle size of 300 μm or less as cellulose powder having a good compactibility and disintegration property.

Patent Document 5 describes micro-crystalline cellulose aggregates (corresponding to Comparative Example 9 of the present application) having an average degree of polymerization of 60-375, apparent specific volume of 1.6-3.1 $cm^3/g$, apparent tapping specific volume of 1.4 $cm^3/g$ or above, a repose angle of 35-42°, and containing 2-80% by weight of component of 200 mesh or above. The cellulose powder obtained according to Examples of these Patent Documents has a small intraparticular pore volume according to the measurement result of pore distribution using mercury porosimetry and the pore structure is entirely different from that of the present invention which is formed intentionally. For that reason, these cellulose powders have a small specific surface area of 0.6-1.2 $cm^3$ and poor compactibility. These publications disclose the control of the compactibility, fluidity and disintegration property of cellulose particles by adjusting the apparent specific volume, but there were problems that in the range of relatively small apparent specific volume of 2.0-2.9 $cm^3/g$, the fluidity and disintegration property were good but the compactibility was unsatisfactory, while with larger apparent specific volume of 3.0-3.2 $cm^3/g$, the compactibility was good but the fluidity and disintegration property were poor.

Patent Document 6 describes β-1,4-glucan powder (corresponding to Comparative Example 1 of the present application) as cellulose powder having good compactibility having an average particle size of at most 30 μm and a specific surface area of 1.3 $m^2/g$. The β-1,4-glucan powder described in the document does not have the secondary aggregate structure, and individual primary particles exist singly. Although this glucan powder has good compactibility, it has problems that the disintegration property is poor and the fluidity is inferior due to the small average particle size.

Patent Document 7 describes a cellulose powder (corresponding to Comparative Example 10 of the present application) having an average degree of polymerization of 100-375, an acetic acid retention rate of 280% or above, Kawakita formula ($P*V0/(V0-V)=1/a*b+P/a$) wherein a is 0.85-0.90, b is 0.05-0.10, an apparent specific volume of 4.0-6.0 $cm^3/g$, substantially no particles of 355 μm or larger, and an average particle size of 30-120 μm as a cellulose powder having good compactibility and disintegration property obtained by hydrolyzing a cellulose-like substance. The cellulose powder obtained by the method of Example described in that document has also a small pore volume within a particle according to the measurement result of pore distribution using the mercury porosimetry and thus the pore structure is entirely different from the intentionally formed pore structure of the present invention. Although the cellulose powder of Patent Document 7 is described to have good compression compactibility and disintegration property, the best balanced Example that is disclosed specifically is measured to have a repose angle of over 55° and the fluidity is not satisfactory enough. There was a problem that in formulations, in which an active ingredient having poor fluidity was used in large proportion, the variation coefficient of tablet weight was larger thereby influencing uniformity of the drug content. Further, when compacting (molding) was performed under high pressure using the cellulose powder according to the document, a high hardness can be obtained but there was a problem of delayed disintegration because there is no intentionally formed intraparticular pore, and water permeability to inside of the particle was low.

Patent Document 8 describes a crystalline cellulose (corresponding to Comparative Example of 11 of the present application) as the cellulose powder having good compactibility, disintegration property and fluidity, which has an average degree of polymerization of 100-375, and in which the particles that pass through a 75 μm sieve and are retained on a 38 μm sieve occupy 70% or more of the total weight, and an average major axis and minor axis ratio of the particles is 2.0 or higher.

Patent Document 9 describes a cellulose powder (corresponding to Comparative Example of 2-4 of the present application) as the cellulose having good compactibility, disintegration property and fluidity, having an average degree of polymerization of 150-450, an average L/D (ratio of major axis/minor axis) of 2.0-4.5 for particles of 75 μm or less, an average particle size of 20-250 μm, an apparent specific volume of 4.0-7.0 $cm^3/g$, and a repose angle of 54° or less and a specific surface area of 0.5-4 $m^2/g$. Since the pore volume within a particle of the cellulose powders described in these publications, similar to the cases described above, measured by the mercury porosimetry is small, the cellulose have entirely different pore structure from the intentionally formed pore structure of the present invention. The cellulose powders described in these publications give a high hardness to a molded body by elongating the shape of particles, but because they have an elongated shape, the apparent specific volume becomes larger, and the higher the compactibility, the fluidity decreases. Among the cellulose powders in Examples described in these publications, the one having the best fluidity was measured to have a repose angle of 44°. For example, when continuous compression was performed at high speed in a formulation in which an active ingredient having poor fluidity was mixed in a large proportion, the variation coefficient of tablet weight was getting larger, thereby influencing uniformity of the drug content, and thus satisfactory result was not obtained in terms of fluidity. Further, when compacting (molding) was performed under high pressure using the cellulose powder according to these publications, high hardness can be achieved but there was a problem of delayed disintegration because there was no intentionally formed intraparticular pore, and water permeability to the inside of particle was low.

Patent Document 10 describes a cellulose powder (corresponding to Comparative Example 14 of the present application) having an average degree of polymerization of 150-450, an average particle size 30-250 μm, an apparent specific volume of over 7 cm$^3$/g and a holding capacity of polyethylene glycol with a molecular weight of 400 of 190% or more. The cellulose powder of this document does not hold a secondary aggregate structure, and primary cellulose particles exist substantially as a singlet. Also, the intraparticular pore volume measured by the mercury porositometry is small and the cellulose powder has an entirely different pore structure from the intentionally formed pore structure of the present invention. Further, when the apparent specific volume is large, the fluidity is greatly impaired, and the repose angle of the best cellulose powder in terms of fluidity according to this document was measured to be 50°. For example, when continuous compacting (molding) was performed at high speed in a formulation in which an active ingredient having poor fluidity was mixed in a large proportion, the variation coefficient of tablet weight was increased, thereby influencing uniformity of the drug content, and thus satisfactory result was not obtained in terms of fluidity. Further, when compacting (molding) was performed under high pressure using the cellulose powder according to the document, high hardness can be achieved but there was a problem of delayed disintegration because there was no intentionally formed intraparticular pores, and water permeability to the inside of particle was low.

In addition, the average particle size of the dispersed cellulose particles in the cellulose dispersion must be 50 μm or larger to increase the apparent specific volume, but the average particle size of the dispersed cellulose particles of the present invention is obtained at 10 μm or larger and less than 50 μm, which is quite different in terms of the production method.

In the range of 2.3-6.4 cm$^3$/g of the apparent specific volume for the cellulose powders described in these Patent Documents 6-9, and in the range of over 7 cm$^3$/g of the apparent specific volume for the cellulose powders described in Patent Document 10, sufficient compactibility was obtained in each case but there was a problem that the fluidity and disintegration property were deteriorated.

Patent Document 11 describes pharmacologically inert round shaped seed core containing 10-70% of a crystalline cellulose having an average degree of polymerization of 60-375 and 10-90% of a water soluble additive as cellulose particles having good fluidity. Further, Patent Document 12 describes a pharmacologically inert round shaped seed core (corresponding to Comparative Example 12 of the present application) containing 50% or more of a crystalline cellulose having a water absorbing capacity of 0.5-1.5 ml/g, roundness of 0.7 or higher, an apparent tapping specific volume of 0.65 g/ml or higher, a friability of 1% or less and an average degree of polymerization of 60-375, wherein distilled water is added to powder containing crystalline cellulose at 50% or more while mixing using a mixer granulator and kneaded to prepare the round shaped seed core. Patent Document 13 describes microcrystalline cellulose particles having a loose bulk density of at least 0.4 g/cm$^3$ (2.5 cm$^3$/g in apparent specific volume), spherical shape, an average particle size of 2-35 μm and a smooth surface, wherein the microcrystalline cellulose particles is prepared by mechanically reducing the particle size of hydrolyzed cellulose particles and by spray-drying. Patent Document 14 describes cellulose system particles (corresponding to Comparative Example 13 of the present application) containing 10% or more of the crystalline cellulose having an average degree of polymerization of 60-350, and having an apparent tapping specific volume of 0.60-0.95 g/ml, roundness of 0.7 or higher, a shape coefficient of 1.10-1.50, and an average particle size of 10-400 μm, wherein the crystalline cellulose is obtained by hydrolyzing a cellulose material to an average degree of polymerization of 60-350, then grinding the result mechanically to the average particle size of 15 μm, and then drying the dispersion containing thus obtained crystalline cellulose in a shape of liquid droplets.

The cellulose particles described in these documents do not form a secondary aggregate structure, and the celluloses obtained by the method of Examples described in Patent Documents have an apparent specific volume of 2.5 cm$^3$/g or lower, nearly spherical shape and good fluidity but are poor in compression compactibility, and under the commonly used compression pressure of 10-20 MPa, a molded body which has sufficient hardness for practical use can not be made.

As described above, for cellulose particles of conventional arts, compactibility, fluidity and disintegration property have been mutually contradictory characteristics, and it has been hoped to obtain cellulose particles having these characteristics in good balance.

On the other hand, since the cellulose particles described in Patent Documents 4-9, and 11-14 do not have intraparticular pores that are intentionally formed, and pore volume within a particle is small, almost no active ingredient can be held in the particles and therefore there have been problems of liquid components bleeding out in compression compacting (molding) and problems in tablet press operation. Also, the cellulose particles described in Patent Document 2 and 3 have intraparticular pores, but the pore diameter is small, and therefore it is difficult for water to permeate into the dense and continuous cellulose wall, which imposes problems that the cellulose particle does not disintegrate in water and quick release of an active ingredient is hindered. The cellulose particles described in Patent Document 10 has an apparent specific volume that is too big, and especially in high speed compression compacting (molding) they sometimes cannot be practically used because of the their fluidity and disintegration property.

Furthermore, since these cellulose particles do not have intraparticular pores that are intentionally formed, and the pore volume within a particle is small, almost no active ingredient can be held in the particles, and thus they have a shortcoming that in solid formulation of an active ingredient that is hard to be soluble in water, the formulation can not be practically used due to slow elution of the active ingredient, unless complicated processes are performed such as temporary granulation with water or an organic solvent, drying and the like. They also have a shortcoming that in solid formulation of an active ingredient that tends to sublimate, the active ingredient re-crystallizes during storage, ruining their commercial value.

The active ingredient in a solid formulation for oral administration is eluted from the formulation to the body fluid in the digestive tract, absorbed from the digestive tract, enters into the blood circulation and expresses the drug effect. Since the active ingredient that is hard to be soluble in water is poorly eluted, sometimes it is excreted out of the body before all the administered active ingredient is eluted and full effect is not expressed. The ratio of the total amount of active ingredient entering into the blood circulation to the administered amount of active ingredient is generally known as bioavailability, and to improve bioavailability and the rapid action of active ingredient, various methods have been investigated up until now for improving the elution of hardly-soluble active ingredients.

Patent Document 15 describes a method for grinding an active ingredient that is hard to be soluble in water and $\beta$-1,4-glucan powder together. This method needs a long time for grinding treatment until crystalline characteristics of $\beta$-1,4-glucan powder are lost, and also powerful shear must be applied continuously for a long time using a roll mixer, thus creating a problem of poor efficiency in the actual production process. Further, $\beta$-1,4-glucan powder that has lost the crystalline characteristics has a problem of poor compression compactibility.

For a solid formulation for oral administration prepared by the direct press method from a main drug that is hard to be soluble in water, Patent Document 16 describes a method for increasing the disintegration of the tablet and the rate of elution of the main drug by increasing the hardness of the tablet and decreasing the variation of the main drug content by adding $\beta$-1,4-glucan, a disintegrator and a surfactant. This document describes no intraparticular pores, and it is not known at all to improve water solubility of a drug by mixing an active ingredient that is hard to be soluble in water and a porous cellulose aggregate. Furthermore, since a surfactant has to be added to facilitate the elution of the active ingredient that is hard to be soluble in water, there is a problem that when this solid formulation was administered, the surfactant caused inflammation of the mucus membrane of the digestive tract.

Further, Patent Document 17 describes that when tablets are produced by the wet press method using a main drug that is hard to be soluble in water and $\beta$-1,4-glucan through the steps of powder mixing, kneading, granulation and drying, tablets having a high tablet hardness, a short disintegration time and a fast elution rate of the main drug can be produced by adding a water soluble polymer solution. Also, this document describes no porous cellulose particle having large intraparticular pores, and it is not known at all to improve water solubility of a drug by mixing an active ingredient that is hard to be soluble in water and a porous cellulose aggregate. Still further in such a method, many steps are essential for drying and there are problems of the cost related to the equipment, and that the energy cost for drying is high. Also, there are problems that this method cannot be applied to an active ingredient inactivated by heat and the like problems.

Patent Document 18 describes a method for improving the elution of a drug by mixing a hardly-soluble drug with porous structured cellulose particles having a particular specific surface area and a pore volume, which is obtained by granulating and drying fine particle like natural cellulose dispersed in an organic solvent by the spray dry method, and absorbing thereto by sublimation. Since the porous cellulose particles described in that document have a high specific surface area and a large pore volume within a particle, the improvement of elution is sure to be observed when the hardly-soluble active ingredient is absorbed by sublimation. However, Example of this Patent Document uses cellulose particles having excessively high specific surface area and the active ingredient absorbed on the surface by sublimation is amorphous and therefore there is a problem of storage stability because during the storage a part of the active ingredient is crystallized and the elution rate is changed, and in a tightly bound compacting composition such as a tablet, there is a shortcoming that the elution of the active ingredient is slow because its disintegration is impeded due to the poor disintegration property.

A sublimatable active ingredient has a problem of bleeding out of a solid formulation during storage, and to prevent this from happening, many of these solid formulations are film coated or sugar coated. However, even with such treatments, there are problems that the active ingredient bleeding out of the formulation through the film layer causes low uniformity of the active ingredient content in the formulation, the active ingredient attached to the surface of the formulation gives irritating smell when taking the formulation or re-crystallizing in a preserving container such as a vial greatly reduces the commercial value. When the coating treatment is not performed on the formulation, the sublimation-re-crystallization is more pronounced than when the coating treatment is performed.

As already described above, in Patent Document 18 cellulose particles having excessively high specific surface area was used, and since the active ingredient absorbed by sublimation on the surface was amorphous, there was a problem of poor storage stability of the active ingredient, and in a tightly bound compacting composition such as a tablet, there was a shortcoming that the elution of the active ingredient was slow because its disintegration was impeded due to the poor disintegration property.

Also, as a method for preventing the re-crystallization caused by sublimation of ibuprofen in solid formulation, Patent Document 19 describes a method for preserving ibuprofen containing solid formulation together with 1 or plurality of stabilizers selected from the group consisting of polyvinyl pyrrolidone, magnesium oxide and sodium bicarbonate in a closed container such as a vial. Using this method the deposition of crystals to the original closed container that has preserved the formulation and the irritating smell of the formulation are surely improved, but polyvinyl pyrrolidone, magnesium oxide, sodium carbonate and the like have to be placed in the container as separate formulations, making the process more complicated, and thus this is entirely different from a single formulation which is made sublimation-proof by adding to the formulation a porous cellulose such as the formulation of the present invention containing a sublimatable active ingredient.

In the past, a composition containing an active ingredient that was oily, liquid or semi solid at normal temperature had problems compared to a solid active ingredient that it is especially prone to tablet pressing problems due to the liquid component bleeding out from the formulation, spots of the liquid component are produced on the surface of the formulation, and in the case of granular formulation, inferior fluidity occurred. These problems not only markedly lower the quality of the product but also cause the low uniformity of the concentration and effect of the active ingredient, and thus improving these problems is a very important task.

In the production of tablets, Patent Document 20-31 describe a method for retaining an active ingredient that is liquid/semi solid at normal temperature to an absorption carrier as it is, or holding an active ingredient dissolved, emulsified or suspended in water, organic solvent, oil, aqueous polymer or surfactant to an absorption carrier, and then compression compacting dried powder or granules obtained after a drying step. However, by the methods of these Patent Documents, the active ingredient that is liquid or semisolid at normal temperature effuses out at the time of compression, causing tablet pressing troubles, and sometimes satisfactory compression molded body may not be obtained. Also, for cellulose particles these Patent Documents do not describe a pore volume within a particle, and it is not known that when the active ingredient that is liquid or semisolid at room temperature is compressed, the addition of the porous cellulose particles of the present invention having a large pore volume within a particle prevents bleeding out by the porous cellulose aggregate holding the active ingredient that is liquid or semisolid inside of the particles and makes preparation of solid formulations such as powder, granules, tablets and the like easier. Still further, in the method described in Patent Document 20-31 many steps are essential for drying and there are problems that the cost related to the equipment, and the energy cost for drying is high.

Patent Document 1: International Patent Application No. 2005/073286 Pamphlet
Patent Document 2: JP-A-1-272643
Patent Document 3: JP-A-2-84401
Patent Document 4: JP-B-40-26274 (CA 699100 A)
Patent Document 5: JP-A-53-127553 (U.S. Pat. No. 4,159,345 A)
Patent Document 6: JP-A-63-267731
Patent Document 7: JP-A-6-316535 (U.S. Pat. No. 5,574,150)
Patent Document 8: JP-A-11-152233
Patent Document 9: International Patent Application No. 02/02643 Pamphlet (US20040053887 A1)
Patent Document 10: International Patent Application No. 2004/106416 Pamphlet (EP1634908)
Patent Document 11: JP-A-4-283520
Patent Document 12: JP-A-7-173050 (U.S. Pat. No. 5,505,983), U.S. Pat. No. 5,384,130)
Patent Document 13: JP-A-7-507692 (U.S. Pat. No. 5,976,600 A)
Patent Document 14: International Patent Application No. 02/36168 Pamphlet (US20040043964 A1)
Patent Document 15: JP-B-53-22138 (U.S. Pat. No. 4,036,990 A)
Patent Document 16: JP-A-53-044617
Patent Document 17: JP-A-54-052718
Patent Document 18: JP-A-03-264537
Patent Document 19: JP-A-08-193027
Patent Document 20: JP-A-56-7713
Patent Document 21: JP-A-60-25919
Patent Document 22: JP-A-61-207341
Patent Document 23: JP-A-11-193229 (EP972513 B1)
Patent Document 24: JP-A-11-35487
Patent Document 25: JP-A-2000-16934
Patent Document 26: JP-A-2000-247869
Patent Document 27: JP-A-2001-181195
Patent Document 28: JP-A-2001-316248
Patent Document 29: JP-A-2002-534455 (U.S. Pat. No. 6,630,150)
Patent Document 30: JP-A-2003-161
Patent Document 31: JP-A-2003-55219

DISCLOSURE OF THE INVENTION

Problem to be Solved by the Invention

The problem of the present invention is to provide an excipient having a good compactibility, fluidity and disintegration property used for producing a molded body containing various active ingredients by making cellulose particles into a porous cellulose aggregate having a specific pore volume.

Means for Solving the Problem

The present inventors, to solve the aforementioned problem, controlled the particle structure of a cellulose aggregate, expressed a secondary aggregate structure, increased an intraparticular pore volume of the cellulose aggregate and controlled the powder properties of the cellulose aggregate to a specific range to complete the present invention.

That is, the present invention is as follows.

(1) A porous cellulose aggregate having a secondary aggregate structure formed by aggregation of primary cellulose particles, a pore volume within a particle of 0.265 cm$^3$/g-2.625 cm$^3$/g, containing type I crystals, and having an average particle size of more than 30 µm and 250 µm or less, a specific surface area of 0.1 m$^2$/g or more and less than 20 m$^2$/g, a repose angle of 25° or more and less than 44°, a swelling degree of 5% or more, and properties to disintegrate in water.

(2) The porous cellulose aggregate according to (1), in which a cylinder-like molded body having a hardness of 70-160 N and a repose angle of over 36° and less than 44° is obtained by weighing 0.5 g of the aforementioned porous cellulose aggregate and placing it in a die, compressing it with a round flat punch with a diameter of 1.1 cm until a pressure of 10 MPa is attained, and holding at the target pressure for 10 seconds.

(3) The porous cellulose aggregate according to (1), in which the cylinder-like molded body having a hardness of 60-100 N and a repose angle of 25° or larger and 36° or smaller is obtained by weighing 0.5 g of the aforementioned porous cellulose aggregate and placing in a die, compressing with a round flat punch with a diameter of 1.1 cm until a pressure of 10 MPa is attained, and holding at the target pressure for 10 seconds.

(4) The porous cellulose aggregate according to any one of (1)-(3) that can be obtained by a production method including: a step of obtaining a dispersion (hereinafter may also be designated as a cellulose dispersion) containing a natural cellulose material in which primary cellulose particles have an average particle size of 10 µm or larger and less than 50 µm, average width of 2-30 µm and average thickness of 0.5-5 µm, and a step of drying thus obtained cellulose dispersion.

(5) The porous cellulose aggregate according to (4), in which the aforementioned cellulose dispersion contains 10% by weight or less of particles that are not sedimented at a centrifugal condition of centrifugal force of 4900 m/s$^2$.

(6) A method for producing the porous cellulose aggregate according to any one of (1)-(3) including: a step of obtaining a dispersion (hereinafter may also be designated as a cellulose dispersion) containing a natural cellulose material in which primary cellulose particles have an average particle size of 10 µm or larger and less than 50 µm, average width of 2-30 µm and average thickness of 0.5-5 µm, and a step of drying thus obtained cellulose dispersion.

(7) The method according to (6), in which the aforementioned cellulose dispersion contains 10% by weight or less of particles that is not sedimented at a centrifugal condition of centrifugal force of 4900 m/s$^2$.

(8) The method according to (6), in which shearing and stirring are performed during a step of subjecting the aforementioned natural cellulose substance to a mechanical treatment such as crushing, grinding or the like or a chemical treatment such as hydrolysis or the like, or a combination of both treatments, or stirring is performed during a step after these treatments.

(9) The method according to (6), in which shearing and stirring are performed during a step of subjecting the aforementioned natural cellulose substance to a mechanical treatment such as crushing, grinding or the like and then during the step of hydrolysis.

(10) The method according to (6), in which the aforementioned natural cellulose substance is subjected to stirring during the step of hydrolysis, or during the step thereafter.

(11) The method according to (8), in which the aforementioned cellulose dispersion contains 10% by weight or less of particles that are not sedimented at a centrifugal condition of centrifugal force of 4900 m/s$^2$.

(12) The method according to (9), in which the aforementioned cellulose dispersion contains 10% by weight or less of particles that are not sedimented at a centrifugal condition of centrifugal force of 4900 m/s$^2$.

(13) The method according to (10), in which the aforementioned cellulose dispersion contains 10% by weight or less of particles that are not sedimented at a centrifugal condition of centrifugal force of 4900 m/s$^2$.

(14) The porous cellulose aggregate according to (4), in which the aforementioned natural cellulose substance is a wood pulp having a level-off polymerization degree of 130-250, a whiteness of 90-99%, $S_{10}$ of 5-20% and $S_{18}$ of 1-10%.

(15) The porous cellulose aggregate according to (5), in which the aforementioned natural cellulose substance is a wood pulp having a level-off polymerization degree of 130-250, a whiteness of 90-99%, $S_{10}$ of 5-20% and $S_{18}$ of 1-10%.

(16) The method for producing the porous cellulose aggregate according to (6), in which the aforementioned natural cellulose substance is a wood pulp having a level-off polymerization degree of 130-250, a whiteness of 90-99%, $S_{10}$ of 5-20% and $S_{18}$ of 1-10%.

(17) The method for producing the porous cellulose aggregate according to (7), in which the aforementioned natural cellulose substance is a wood pulp having a level-off polymerization degree of 130-250, a whiteness of 90-99%, $S_{10}$ of 5-20% and $S_{18}$ of 1-10%.

(18) The method for producing the porous cellulose aggregate according to (8), in which the aforementioned natural cellulose substance is a wood pulp having a level-off polymerization degree of 130-250, a whiteness of 90-99%, $S_{10}$ of 5-20% and $S_{18}$ of 1-10%.

(19) The method for producing the porous cellulose aggregate according to (9), in which the aforementioned natural cellulose substance is a wood pulp having a level-off polymerization degree of 130-250, a whiteness of 90-99%, $S_{10}$ of 5-20% and $S_{18}$ of 1-10%.

(20) The method for producing the porous cellulose aggregate according to (10), in which the aforementioned natural cellulose substance is a wood pulp having a level-off polymerization degree of 130-250, a whiteness of 90-99%, $S_{10}$ of 5-20% and $S_{18}$ of 1-10%.

(21) The method for producing the porous cellulose aggregate according to (11), in which the aforementioned natural cellulose substance is a wood pulp having a level-off polymerization degree of 130-250, a whiteness of 90-99%, $S_{10}$ of 5-20% and $S_{18}$ of 1-10%.

(22) The method for producing the porous cellulose aggregate according to (12), in which the aforementioned natural cellulose substance is a wood pulp having a level-off polymerization degree of 130-250, a whiteness of 90-99%, $S_{10}$ of 5-20% and $S_{18}$ of 1-10%.

(23) The method for producing the porous cellulose aggregate according to (13), in which the aforementioned natural cellulose substance is a wood pulp having a level-off polymerization degree of 130-250, a whiteness of 90-99%, $S_{10}$ of 5-20% and $S_{18}$ of 1-10%.

(24) A compacting (molding) composition containing one or more groups of active ingredients and the porous cellulose aggregate according to any one of (1)-(3).

(25) A compacting (molding) composition characterized by containing one or more groups of active ingredients and the porous cellulose aggregate according to (4).

(26) A compacting (molding) composition characterized by containing one or more groups of active ingredients and the porous cellulose aggregate according to (5).

(27) A compacting (molding) composition characterized by containing one or more groups of active ingredients and the porous cellulose aggregate that can be obtained by the method according to (6).

(28) A compacting (molding) composition characterized by containing one or more groups of active ingredients and the porous cellulose aggregate that can be obtained by the method according to (7).

(29) A compacting (molding) composition characterized by containing one or more groups of active ingredients and the porous cellulose aggregate that can be obtained by the method according to any one of (8)-(10).

(30) A compacting (molding) composition characterized by containing one or more groups of active ingredients and the porous cellulose aggregate that can be obtained by the method according to (11).

(31) A compacting (molding) composition characterized by containing one or more groups of active ingredients and the porous cellulose aggregate that can be obtained by the method according to (12).

(32) A compacting (molding) composition characterized by containing one or more groups of active ingredients and the porous cellulose aggregate that can be obtained by the method according to (13).

(33) The compacting (molding) composition according to (24) that is a tablet.

(34) The compacting (molding) composition according to any one of (25)-(28) that is a tablet.

(35) The compacting (molding) composition according to (29) that is a tablet.

(36) The compacting (molding) composition according to any one of (30)-(32) that is a tablet.

Advantages of the Invention

Since the porous cellulose aggregate of the present invention is superior in compactibility, fluidity and disintegration property, in using the porous cellulose aggregate of the present invention as an excipient in production of a molded body containing various active ingredients, a molded body having a good homogeneous miscibility with an active ingredient, no variation of weight, a good uniformity in active ingredient content, a sufficient hardness, no tablet press problems, low friability loss and a good disintegration property can be provided by a simple method.

Since the porous cellulose aggregate of the present invention greatly enhances elution tablet pressing and disintegration property of the active ingredient in a solid formulation containing an active ingredient which is hard to be soluble in water, it is especially useful as an excipient for the solid formulation. Further, since the porous cellulose aggregate of the present invention prevents the effusion of a liquid or semi-solid active ingredient and improves disintegration property in a solid formulation containing the liquid or semi-solid active ingredient, it is especially useful as an excipient for the solid formulation. In addition, in mixing of the active ingredient and components other than the active ingredient or in a solid formulation using thereof, when an active ingredient exists in a minute amount, and in particular when the average particle size of the active ingredient is small and the attachment aggregation characteristic is high, the porous cellulose aggregate of the present invention can contribute to a mixing rate of an active ingredient and to a reduction of the variation of concentration, and improves tablet pressing and disintegration property, and thus it is especially useful as an excipient for the solid formulation. Still further, the porous cellulose aggregate of the present invention can prevent recrystallization by a sublimation of a sublimatable active ingredient in a solid formulation of the sublimatable active ingredient and prevent a reduction of the market value, and thus it is especially useful as an excipient for the solid formulation.

BEST MODE FOR CARRYING OUT THE INVENTION

Figure 1:
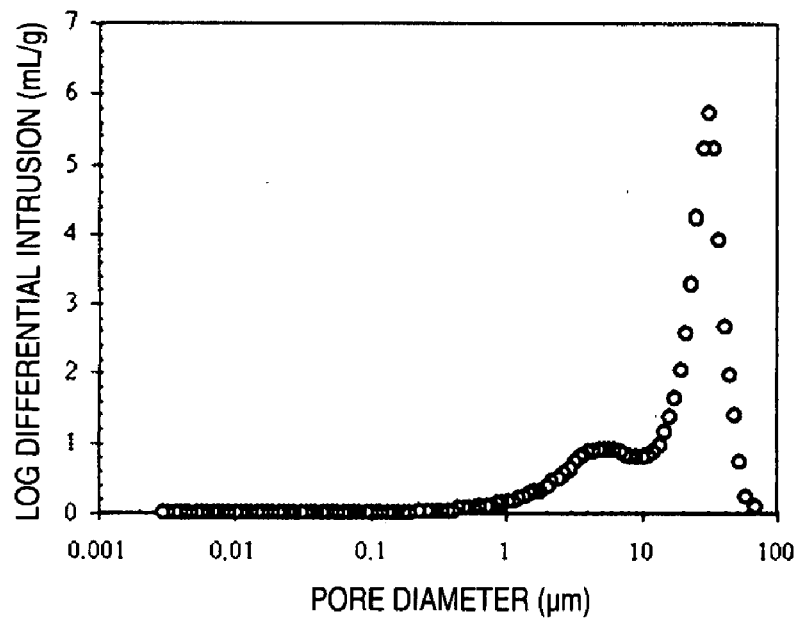
FIG. 1 is the pore size distribution of the porous cellulose aggregate (Example 1) of the present invention measured by mercury porosimetry.

The present invention will be described particularly centered around the preferred mode as follows.

The porous cellulose aggregate of the present invention must have a secondary aggregate structure composed of aggregated primary particles. This is the secondary aggregate structure having clear boundaries of the primary particles when the surface of the particles is observed at a magnification of ×250 or ×1500 by a scanning electron microscope (SEM). The secondary aggregate structure formed by the aggregation of the primary particles is closely related to disintegration property, and the structure without this particular structure is not preferable because the disintegration property is deteriorated. When the boundaries of the primary particles are not clear, for example having the dense and continuous cellulose septa, it is not preferable because the particles do not disintegrate in water and the disintegration property of a molded body becomes also poor due to the densely continued and tightly bound primary cellulose particles.

Further, the secondary aggregate structure formed by the aggregation of the primary particles is also closely related to not only disintegration property but also elution of an active ingredient. Water permeability to the porous cellulose particles having the secondary aggregate structure formed by the aggregation of the primary particles is fast, and disintegration of the primary particles are accelerated, and when an active ingredient is retained, the elution of the active ingredient which is hard to be soluble in water is effectively improved because the contact area between the active ingredient and water is increased.

In addition, this secondary aggregate structure is homogeneously distributed whether in the inside or on the surface of the particles, and is preferred because, when the secondary aggregate structure is mixed with an active ingredient, the active ingredient can be retained between gaps of the primary cellulose particles and in particular, effusion of the liquid component can be prevented.

Still further, this secondary aggregate structure is preferred because it allows retention of the active ingredient not only on the surface but also inside of the particles, and therefore it contributes to the improvement of the mixing rate of the active ingredient and mixing uniformity, and can greatly reduce the variation of the concentration.

In the porous cellulose aggregate of the present invention the intraparticular pore volume must be 0.265 $cm^3$/g-2.625 $cm^3$/g. Porous particles having a large intraparticular pore volume are superior in plastic deformability, and since the particles tend to collapse on compression, they are superior in compactibility. The porous cellulose aggregate of the present invention is derived originally from cellulose in which the pore volume of the aggregated particles is intentionally enlarged, and thus the plastic deformability is increased by changing the structure of the particles themselves. For that reason the particles express high compression compactibility irrespective of the apparent specific volume of the particles. When the intraparticular pore volume is less than 0.265 $cm^3$/g, the primary cellulose particles have only the intraparticular pores that the primary cellulose particles originally have or that are formed naturally on aggregating cellulose, not intentionally formed, and thus they are poor in plastic deformability. To improve the compactibility, the apparent specific volume of the particles must be larger, resulting in poor fluidity. The porous cellulose aggregate of the present invention can keep a good compactibility with a relatively small apparent specific volume, and as a result the aggregate having also a superior fluidity can be obtained.

When the intraparticular pore volume is 0.265 $cm^3$ or larger, sufficient pore volume is present in the particles, and an active ingredient, which is once incorporated in the pores on the surface of the particles during the mixing process and compression process, is not released easily, and thus these particles are preferred because sufficient amount of the liquid component can be retained in the intraparticular pores, and the effusion can be prevented. When a solid active ingredient is used, the finely ground active ingredient can be retained homogeneously and in large amount to improve water dispersion and elution, and the recrystallization of sublimatable active ingredient is prevented, especially the recrystallization during storage is prevented, and thus these particles are preferred because they can contribute to the stabilization and prevention of degeneration of the commercial value, and further they are preferred because they can contribute to the improvement of a mixing rate and mixing uniformity of the active ingredient and can reduce the variation of the concentration greatly.

When an active ingredient which is hard to be soluble in water is used by dissolving temporally, suspending or emulsifying, they are preferred because they are superior in retaining a liquid component. A drug concentration variation coefficient that is an index of the variation of the concentration of an active ingredient is preferably not over 3.0% during the mixing period, more preferably 2.0% or less, and especially preferably 1.5% or less. Especially when an active ingredient that has an average particle size of 10 μm or less and has extremely high aggregatability is mixed with cellulose particles having the intraparticular pore volume of 0.265 $cm^3/g$ or higher such as the porous cellulose aggregate of the present invention, it is preferred because the active ingredient is retained not only on the surface of the particles but also inside of the particles and thus the drug concentration variable coefficient can be 2.0% or less.

When the intraparticular pore volume is less than 0.265 $cm^3/g$, the effect described above can not be obtained because the dispersion uniformity and retention capacity of a solid or liquid active ingredient are impaired, causing variation of the concentration of the active ingredient, aggregation of solid formulation, poor compression compactibility, recrystallization of sublimative active ingredients during storage and lowering of the stability and commercial value, and therefore it is not preferred.

The larger the intraparticular pore volume is, the better, but the pore volume that a particle can have is limited and is at most 2.625 $cm^3/g$.

Furthermore, if the pore volume exceeds 2.625 $cm^3/g$, it is not preferred because the apparent specific volume is increased and the fluidity is decreased.

As described above, the larger the intraparticular pore volume, the more it is preferred because the compactibility is higher due to the particle having plastic deformability, the active ingredient is incorporated inside, improving the elution, the ground active ingredient is retained in a large quantity, recrystallization of the sublimative component can be prevented, the mixing rate of the active ingredient is increased, the mixing uniformity is improved, the liquid component can be retained and the like, but when the intraparticular pore volume is too large, the apparent specific volume tends to be increased and the fluidity is decreased and therefore the preferred range of the intraparticular pore volume where the compactibility and fluidity are in good balance is 0.265 $cm^3/g$-1.500 $cm^3/g$, and especially preferred range is 0.265 $cm^3/g$-1.000 $cm^3/g$.

The distribution of pore diameter of the porous cellulose aggregate of the present invention is measured, for example, by mercury porosimetry. It is preferred that a clear peak is identified especially in the range of 0.1-10 μm. Further, the median pore diameter that is a peak top of the pore distribution is closely related to water permeability into the particle, and is preferably 0.3 μm or larger. Water permeability becomes larger when the median pore diameter is 0.3 μm or larger, and the disintegration property is improved further. The larger the median pore diameter the more preferable, but it is at most in the range of 10-15 μm.

In the production method according to Patent Document 1, two or more groups of primary cellulose particles having different average particle size were mixed and dried, and thus the packing among the particles was too good and it was difficult to obtain the pore diameter substantially of 3 μm or larger. The present invention is especially superior in the balance of the compactibility and disintegration property, and the preferred median pore diameter is 3-15 μm and more preferred is 3-10 μm.

The crystalline structure of the porous cellulose aggregate of the present invention must be the type I. The crystalline structure of cellulose, type I, II, III, IV and the like are known, and among them type I and type II are called as "natural cellulose" and "regenerated cellulose", respectively and are used in general, but type III and IV are obtained in laboratory scale only and not generally used in industrial scale. Natural cellulose has been consumed as a plant fiber foodstuff from ancient times and is widely used at present as a dispersion stabilizer for liquid foodstuffs and an excipient for pharmaceutical products. On the other hand, regenerated cellulose is a product of the altered crystalline structure which is regenerated by removing solvents and the cellulose solution of a chemical such as carbon disulfide, sodium hydroxide or the like, and some of them are used as a compacting agent for foodstuffs in a wet processing. The regenerated cellulose of type II crystalline structure is not preferred, because with altered crystalline structure from natural cellulose of type I crystalline structure, the particles become stiff, have decreased plastic deformability on compression and cannot give a sufficient hardness to the molded bodies.

In the porous cellulose aggregate of the present invention, the average particle size must be over 30 μm and 250 μm or less. When the average particle size is 30 μm or less, cellulose particles aggregate each other, the active ingredient is not diffused homogeneously in mixing with the active ingredient, the variation of the active ingredient tends to be greater in the molded body obtained, and the variation of the weight of the molded body in the continuous production also tends to be greater. Further, when the average particle size is over 250 μm, separation and segregation tend to occur in continuous compression of a powder formulation mixed with an active ingredient having poor fluidity.

The specific surface area of the porous cellulose aggregate of the present invention must be 0.1 $m^2/g$ or larger and less than 20 $m^2/g$. At the specific surface area less than 0.1 $m^2/g$, the compression compactibility is lower, and it is difficult to give a molded body high hardness and low friability. Further, when the specific surface area is over 20 $m^2/g$, it is not preferable to mix an active ingredient that tends to be inactivated by cellulose, because the contact area between cellulose and the active ingredient is excessively too large, and the active ingredient tends to lose activity.

The repose angle of the porous cellulose aggregate of the present invention must be 25° or larger and less than 44°. Normally, an active ingredient is prepared so that when administered, it diffuses in gastric juice and intestinal juice media and enhances drug effect rapidly, and for that reason it is often grounded or is fine powder from the beginning. Since it is fine powder, the fluidity is poor, and at the repose angle of 44° or larger, it is not preferred for the fluidity of the mixed powder when a large amount of an active ingredient having poor fluidity is mixed. Especially, there is tendency of the variation of the weight of the molded bodies at high speed tablet pressing at a speed of several ten thousands-several hundred thousands tablets/hour. The fluidity is better with the smaller repose angle and the repose angle of 25°-42° is especially good. More preferable is a repose angle of 25°-40°. The repose angle of less than 25° is not preferable for separation and segregation of the active ingredient.

The porous cellulose aggregate of the present invention must have a swelling rate of 5% or larger, preferably of 6-50%, especially preferably of 7-30%. The swelling degree can be measured as follows. From the volume ($V_1$) of about 10 g of a powder slowly poured into a cylindrical container having a volume of 100 cm$^3$, and the volume ($V_2$) after standing for 8 hours after adding about 50 cm$^3$ of pure water to the powder layer and mixing so that the powder is completely wet, using following formula the swelling degree is obtained.

Swelling degree(%)=($V_2$-$V_1$)/$V_1$×100

Swelling degree is a gap between the primary cellulose particles created when the primary cellulose particles are aggregated by drying, and the larger is the value, the easier to disintegrate due to elevated water permeability into the particles. In the conventional cellulose powder, the one having a high compactibility has to reduce the swelling degree resulting in sometimes insufficient disintegration property, and for the other having a high fluidity, although the swelling degree is high and the disintegration property is good, it is difficult to have a high level of compactibility. Among the conventional cellulose powder, the one having the best balance for compactibility and disintegration property is the porous cellulose aggregate of Patent Document 1. There is no description of the swelling degree in that document, but the measurement of the porous cellulose aggregate according to Example described in that Patent Document revealed that the higher the compactibility, the lower the value of the swelling degree, and it was 4% at most. So far it has not been achieved to increase compactibility while maintaining disintegration property by keeping swelling degree at high level, and the present invention has achieved this for the first time.

The apparent specific volume of the porous cellulose aggregate of the present invention is preferably 2.0-6.0 cm$^3$/g. The porous cellulose aggregate of the present invention has hardness, fluidity and disintegration property in a good balance in almost whole part of the apparent specific volume compared to the conventional one because of the porous structure. To obtain a high compression compactibility, the apparent specific volume is preferably 2.0 cm$^3$/g or larger, and to obtain a higher fluidity the apparent specific volume is preferable 6.0 cm$^3$/g or less. Especially preferred apparent specific volume is 2.5-5.0 cm$^3$/g.

For the porous cellulose aggregate of the present invention, cylindrical molded bodies, obtained by weighing 0.5 g of the cellulose powder, placing it in a die (KIKUSUI SEISAKUSHO LTD, Material SUS2, 3 were used), compressing with a circular flat punch with a diameter of 1.1 cm (KIKUSUI SEISAKUSHO LTD, Material SUS2, 3 were used) until the pressure of 10 MPa and 20 MPa was attained (AIKOH ENGINEERING CO., LTD. PCM-1A was used. The compression rate was 1 cm/minute), and holding at the target pressure for 10 seconds, have preferably the hardness of 60 N or higher and 165 N or higher, respectively. If the hardness of 10 MPa is less than 60 N and the hardness of 20 MPa is less than 165 N under each condition, the molded bodies containing a large amount of an active ingredient produced at the rate of several ten thousands—several hundred thousands tablets/hour have a low hardness, tablet pressing problem such as friability, capping tend to occur. The tablet hardness shown here is higher the better, but the hardness of 10 MPa and 20 MPa products are 160 N and 450 N, respectively, at most.

When the aforementioned cylindrical molded body obtained by compressing to a pressure of 10 MPa has hardness of 70-160 N, or the one obtained by compressing to 20 MPa has hardness of 170-410 N and a repose angle is over 36° and less than 44°, the porous cellulose aggregate of the present invention is especially superior because at a high drug content of about 30% by weight or more, addition of a small amount of 1-30% by weight of the porous cellulose aggregate of the present invention gives physical property required for a formulation such as sufficient compactibility, friability, disintegration property, content uniformity and the like. When a cylindrical molded body, obtained by weighing 0.5 g of a drug having a tablet pressing problems such as sticking, capping and the like, placing it in a die (KIKUSUI SEISAKUSHO LTD, Material SUS2, 3 were used), compressing with a circular flat punch with a diameter of 1.1 cm (KIKUSUI SEISAKUSHO LTD, Material SUS2, 3 were used) until the pressure of 50 MPa was attained (AIKOH ENGINEERING CO., LTD. PCM-1A was used. The compression rate was 1 cm/minute), and holding at the target pressure for 10 seconds, have preferably the hardness of 50 N or lower, preferably 40 N or lower, more preferably 20 N or lower, or when both of the characteristics are present, the porous cellulose aggregate of the present invention is especially effective. For conventional cellulose powder, even if the tablet pressing problems such as sticking and capping can be controlled at a high drug content of about 30% by weight, the fluidity was not sufficient, and the practical application was not possible due to the tablet weight CV, content CV and the like. The present invention has markedly improved the fluidity of the conventional cellulose powder in the usage described above, and is superior in expressing both compactibility and fluidity at high level, despite of the fact that compactibility and fluidity have been contradictory characteristics until now. Further, when the aforementioned cylindrical molded body obtained by compressing to 10 MPa has hardness of 60-100 N, or the one obtained by compressing to 20 MPa has hardness of 165-410 N and a repose angle is 25-36°, the porous cellulose aggregate of the present invention is especially preferred because the high drug content of 30% by weight or above has become possible for the first time in a formulation that can contain an excipient at about 30% by weight or more. For the conventional cellulose, lowering the repose angle causes lowering of the compactibility, and thus even if the cellulose powder content is about 30% by weight or more, in trying to increase drug content, the cellulose powder having good fluidity shows insufficient compactibility and the cellulose powder having good compactibility shows insufficient fluidity resulting in difficulty in formulating, but the present invention has markedly improved the fluidity of the conventional cellulose powder in the usage described above, and is superior in expressing both compactibility and fluidity at high level, despite of the fact that compactibility and fluidity have been contradictory characteristics until now. For the porous cellulose aggregate of the present invention, the disintegration time of the cylindrical molded body obtained under the condition of compressing to a pressure of 20 MPa and keeping the target pressure for 10 seconds by the aforementioned method is preferably for 75 seconds or shorter for the sake of disintegration property. Especially preferable if it is 50 seconds or shorter. This disintegration time is shorter the better. Normally, an active ingredient is prepared so that when administered, it diffuses in gastric juice and intestinal juice media and enhances drug effect rapidly, but when the disintegration time of the molded body is getting longer, and the drug is eluted from the molded body slower and not absorbed at the digestive tract quickly, and the rapid drug effect tends to be decreased.

Since compression compactibility and disintegration property are contradictory characteristics and the porous cellulose aggregate of the present invention raised these characteristics to a level not achieved before, preferably the hardness of the cylindrical molded body obtained by compressing to 10 MPa is 60-160 N, or the hardness of the cylindrical molded body obtained by compressing to 20 MPa is 165-410 N and the disintegration time is 75 seconds or shorter, and especially preferably the hardness of the cylindrical molded body obtained by compressing to 10 MPa is 60-160 N, or the hardness of the cylindrical molded body obtained by compressing to 20 MPa is 165-410 N and the disintegration time is 50 seconds or shorter. Since the porous cellulose aggregate of the present invention can be made with a larger median pore diameter compared to the porous cellulose aggregate of the Patent Document 1, it has a higher swelling degree, and when compared at the same hardness, it has an advantage of having a shorter disintegration time.

A formulated powder is obtained by placing 55 weight parts of acetaminophen (API Corporation, powder type), 0.25 weight parts of light anhydrous silicic acid (NIPPON AEROSIL CO., LTD., Commercial name: Aerosil 200), 27 weight parts of cellulose powder, 2 weight parts of crospovidone (BASF, Commercial name: Collidone CL) and 15 weight parts of granular lactose (Lactose New Zealand, Commercial Name: Super-Tab) in a 100 L scale V Type Mixer (Dalton Co., Ltd.) and mixing for 30 minutes, and then adding 0.5 weight parts of magnesium stearate (TAIHEI CHEMICAL INDUSTRIAL CO., LTD., Plant origin) and mixing for further 5 minutes. Thus obtained formulated powder is subjected to tablet pressing using a rotary tablet press (KIKUSUI SEISAKUSHO LTD, Commercial name: LIBRA-II, 36 lines, Rotary table φ410 mm) and a punch with 8 mm diameter and 12 R, at a turn table speed of 50 rpm, at a compression force of 7.5 kN. For the porous cellulose aggregate of the present invention it is preferable that thus obtained 200 mg molded body has a hardness of 50 N or higher and a friability of less than 1% and no tablet pressing problem.

An excipient having high compactibility is required to give hardness and to reduce friability to a formulation containing a large quantity of a drug having poor compactibility, and at the same time an excipient having fluidity is required to reduce the variation of weight when a high speed and continuous compacting is performed. Such a formulation containing a large amount of a drug having low compactibility and the production of the molded body at such a high speed can only be realized by mixing the excipient having good compactibility and good fluidity such as the present invention. When the hardness of the molded body is less than 50 N and the friability is 1% or larger, it is not preferred because abrasion, dust generation, cracking and chipping occur during transportation. Occurrence of tablet pressing problems is not preferred because inferior products are produced. The hardness here is higher the better but is at most 100 N, and the friability is lower the better.

For the porous cellulose aggregate of the present invention the tablet hardness of the compacting composition is preferably 50-100 N (tablet pressing pressure range: 1-10 kN) and the variation of tablet weight (CV value) is preferably 2.0 or less when the repose angle of the final whole formulated powder which composes the compacting composition of the present invention is 25°-45° by adding 30-90% by weight of cellulose particles to 0.001-50% by weight of a formulated powder having poor fluidity consisting of an active ingredient and components other than cellulose particles and having a repose angle of 45°-55°, and tablets are pressed at the high speed of 50,000 tablets or more per hour. Preferably the whole formulated powder has a repose angle of 45° or less, the tablet hardness of the compacting composition is 50-100 N and the variation of the tablet weight (CV value) is 1.5% or less, and especially preferably the whole formulated powder has a repose angle of 42° or less, the tablet hardness of the compacting composition is 50-100 N and the variation of the tablet weight (CV value) is 1.0% or less (Example 17-19 and Comparative Example 80-91).

In direct tablet pressing and the like, when the fluidity of the active ingredient in the composition and components other than the porous cellulose aggregate of the present invention is bad (repose angle of 45°-55°) and/or the compression compactibility of such components are poor, it is one of the characteristics that a remarkable effect can be obtained by mixing the porous cellulose aggregate of the present invention in a large quantity which could not be obtained by conventional cellulose particles and cellulose powder, because the porous cellulose aggregate of the present invention has compactibility, fluidity and disintegration property in a good balance. That is, in conventional cellulose powder and cellulose particles, the compactibility increases as the added amount of cellulose is increased but the fluidity and disintegration property are getting poorer due to the fluidity being closer to that of cellulose powder and cellulose particles themselves, and consequently there were problems that the high speed tablet pressing at a practical production speed was difficult and that the disintegration of thus obtained tablets was delayed. Against such problems, the porous cellulose aggregate of the present invention has an advantage of the fluidity being improved rather than getting worse when the porous cellulose aggregate of the present invention is mixed in a large quantity, because the porous cellulose aggregate of the present invention has a superior balance in the compactibility and fluidity, disintegration property at such a high level which is not attainable by the conventional cellulose powder and cellulose particles. "Mixing in a large quantity" in the present invention means that the composition contains 30-90% of the porous cellulose aggregate of the present invention. Preferably the content is 30-80% and especially preferably 30-70%.

Following is the description of the method for producing the cellulose powder of the present invention.

To produce the porous cellulose aggregate of the present invention, for example, a dispersion containing a natural cellulose material (hereinafter also designated as cellulose dispersion) needs to be obtained in which the average particle size of the primary cellulose particles is 10 μm or larger and less than 50 μm, the average width is 2-30 μm, and the average thickness is 0.5-5 μm. It is preferable because entanglement of the primary cellulose particles to each other can be promoted during the drying process by making the primary cellulose particles in such a shape. In the past, it was difficult to keep the shape of aggregated particles spherical because the longer the major axis of the primary cellulose particles is, the more difficult for entanglement of particles to occur. However, the present invention has focused on the shape of the primary cellulose particles and proven for the first time that the entanglement of the particles can be promoted by controlling it in a specific range. By promoting the entanglement of the primary cellulose particles each other, it became possible for the first time to make the aggregated particles in a spherical form in an easily controllable manner and to enhance plastic deformability of the particles thus giving compactibility more easily by creating gaps inside of the aggregated particles. In the past, to control the shape of aggregated particles spherical, the major axis of the primary cellulose particles need to be shortened. However, during the process of treating the primary cellulose particles by a mechanical treatment or hydrolysis, or a combination of both, the shorter the major axis of the primary cellulose particles becomes, the more of the fine fragments of the primary cellulose particles are generated, creating the problem that these fine fragments occupy the gap between the aggregated particles and a sufficient mold deformity can not be obtained and the compactibility is decreased. Thus, it was necessary to granulate particles without shortening the major axis of the primary cellulose particles, but such particles are difficult to aggregate and to improve sphericity. Since the generation of the fine fragments of the primary cellulose particles described above in large quantity causes filling of the gaps between the aggregated particles, it is preferable to prepare a cellulose dispersion that contains 10% by weight or less particles that are not sedimented under a centrifuge condition with a centrifugal force of 4900 m/s$^2$. The porous cellulose aggregate of the present invention can be obtained by the method for production including a step of drying that cellulose dispersion.

The natural cellulose substance in the present invention may be derived from plants or animals and includes fibrous substances derived from natural products containing cellulose, for example, wood, bamboo, straw, cotton, ramie, bagasse, kenaf, beet, ascidian and bacterial cellulose, and may have a crystalline structure of type I cellulose. Among the above natural cellulose substances, one group may be used as a material or a mixture of two or more groups can be used. It is preferable to be used in the form of purified pulp but the purification of the pulp is not particularly restricted, and any of the dissolved pulp, kraft pulp, NBKP pulp and the like may be used. The pulp derived from wood is preferable because of the high purity of α-cellulose, easiness to obtain, the supply being stable and the like.

It is preferably a wood pulp in which a level off polymerization degree measured by the copper ethylenediamine solution method is 130-250, and whiteness 90-99%, $S_{10}$ is 5-20% and $S_{18}$ is 1-10%. The level off polymerization degree of less than 130 is not preferable because the compactibility is hard to be expressed. The polymerization degree of over 250 is not preferable because the average width and average thickness of the primary cellulose particles are hard to control in a specified range. The whiteness of less than 90 is not preferable because the external appearance of the porous cellulose aggregate is poor. The whiteness is higher the better but is at most about 99%. $S_{10}$ and $S_{18}$ of outside the range described above are not preferable in the compactibility and yield. Here, in the natural cellulose substance, the material such as pulp may be hydrolyzed or not hydrolyzed. If hydrolyzed in particular, it may be acid hydrolysis, alkali hydrolysis, thermal hydrolysis, steam explosion or the like, and may be any one of the method or a combination of two or more methods.

In the method described above, a medium that is used for dispersing a solid containing the natural cellulose substance is preferably water but is not particularly restricted as long as it can be used industrially, for example, a mixture of water and an organic solvent may be used. The organic solvent includes, for example: alcohols such as methanol, ethanol, isopropyl alcohol, butyl alcohol, 2-methylbutyl alcohol and benzyl alcohol; hydrocarbons such as pentane, hexane, heptane and cyclohexane; ketones such as acetone and ethylmethyl ketone. In particular, the organic solvent that can be used for pharmaceutical use is preferred and includes those classified as solvents in "Pharmaceutical additives" (published by Yakuji Nippo Limited.). Water and organic solvents are freely used singly or in combination of two or more, and after dispersing the cellulose in one kind of medium, the medium is removed and the cellulose may be dispersed in a different medium.

The porous cellulose aggregate of the present invention needs to be produced by preparing a cellulose dispersion, in which the primary cellulose particles have an average particle size of 10 μm or above and less than 50 μm, an average width of 2-30 μm, an average thickness of 0.5-5 μm, and which contains 5-40% by weight of the solid fraction, by subjecting the natural cellulose substance to treatments that are not particularly restricted as long as they are publicly known, for example, mechanical treatment such as milling and grinding, or chemical treatment such as hydrolysis or an appropriate treatment of a combination of both, and then by drying the dispersion.

The primary cellulose particles in the present invention mean particles having the size in the range of 1-500 μm in which the fibers are split and newly formed, in the case of fibers composing the natural cellulose substance, or in the cases where the natural cellulose substance is subjected to mechanical treatments such as milling and grinding or the natural cellulose substance is subjected to chemical treatment such as hydrolysis. A method for making the average particle size of the primary cellulose particles less than 50 μm is achieved, for example, by a mechanical treatment such as milling and grinding, or a publicly known separation treatment such as cyclone, centrifugation and sieving or an appropriate combination of both by controlling appropriately conditions generally known to influence the treatment such as the amount to be treated, shearing force (rotating rate, shape and size of rotating wings and the like can influence), centrifugal force and the size of the sieve mesh, or for example, by a chemical treatment such as acid hydrolysis by changing appropriately conditions such as acid concentration and temperature, or in addition to these by changing appropriately conditions that are already known to influence the mechanical treatment and separation treatment described above.

Performing hydrolysis at higher acid or alkali concentration and reaction temperature, in general, the polymerization degree of cellulose tends to be lower and the average dispersed particle size of cellulose in the dispersion tends to be smaller. Also stirring the solution with more force, the average dispersed particle size of cellulose tends to be smaller. Therefore, by controlling the stirring force in the steps of hydrolysis and/or dispersion of the natural cellulose substance, the polymerization degree of the material cellulose can be controlled in the desired range. Since the stirring force is dependent on a width, height, volume of the stirring layer, a kind of wing, a wind diameter, the stirring rotation rate and the like, it is difficult to define in a specific range, but it is preferable that the product of the wing diameter (m) and the stirring rotation rate (rpm) is in the range of 5-200, more preferably 10-150, especially preferably 10-120.

A method for making the primary cellulose particles have an average width of 2-30 μm, an average thickness 0.5-5 μm is not particularly restricted as long as the method, for example, splits the primary cellulose particles to a longitudinal direction, and includes a method that subjects wood pulp to a treatment such as a high pressure homogenizer treatment and optionally to a mechanical treatment such as grinding and a fraction treatment or an appropriate combination of both. In the high pressure homogenizer treatment a pressure may be appropriately controlled in the range of 10-200 MPa but it may also be dependent on the amount to be treated. Also, a pulp may be selected and used in which the primary cellulose particles have an average width of 2-30 μm and an average thickness of 0.5-5 μm. The cellulose dispersion is preferably prepared containing particles that are not precipitated by a centrifugal of condition centrifugal force of 4900 m/s$^2$ at 10% by weight or less, and such methods includes, for example, in the case of acid hydrolysis, a method for changing the hydrolysis conditions appropriately so that the hydrolysis is difficult to proceed, a method for removing fine particle components that are hard to precipitate from the residue or the dispersion by the separation treatment or the like, or a combination of both methods.

In the hydrolysis of a natural cellulose substance there is a tendency that the higher the acid concentration and the higher the temperature, the more fine particle components that are hard to precipitate are generated, but since the extent of hydrolysis is different depending on the degree of polymerization of the natural cellulose substance, origin of the material, the extraction method for the cellulose substance such as method for producing pulp and the like, it is difficult to define the hydrolysis conditions in a universal way. However, an appropriate hydrolysis condition can be readily determined by measuring the weight of particles which are not precipitated at a centrifugal condition of centrifugal force of 4900 m/s$^2$ under which the % by weight of the particles is 10% by weight or less.

The centrifugal condition of centrifugal force of 4900 m/s$^2$ in the present invention means to determine the rotating rate for each commercially available centrifuge considering the rotating radius (using the maximum radius) of the centrifuge using the calculation method for a centrifugal force defined by the following formula, and under the condition of such rotating rate to perform a centrifugation at the range of the temperature of 15-25° C. for 10 minutes. As the commercially available centrifuge, an inverter-multi purpose high speed refrigerated centrifuge (Type 6930, KUBOTA Corporation, Rapid was used as a mode for acceleration and deceleration) and a RA-400 angle rotor (volume: 50 cm$^3$, material: polypropylene co-polymer, tube angle: 35°, the maximum radius: 10.5 cm, the minimum radius: 5.8 cm, rotation rate: 4100 rpm) are preferably used.

$$\text{Centrifugal force(m/s}^2\text{)}=11.18\times(\text{rotation rate(rpm)}/1000)^2\times\text{rotation radius(cm)}\times 9.8(\text{m/s}^2)$$

To prepare a cellulose dispersion, in which the average particle size of the primary cellulose particles is 10 μm or above and less than 50 μm, an average width is 2-30 μm and an average thickness is 0.5-5 μm (preferably, in addition to these, particles that are not precipitated at the centrifugal condition of centrifugal force of 4900 m/s$^2$ are 10% by weight or less), contributes to form gaps inside the aggregate due to the entanglement each other between the neighboring primary cellulose particles when aggregates of the primary cellulose particles are formed, because the primary cellulose particles having a specific average width and average thickness are flexible when the cellulose dispersion is dried, and further preferably contributes for the gaps formed in the aggregates, without being embedded by the particles, to continue forming porous secondary aggregate structure having a large intraparticular pore volume after drying because among the primary cellulose particles in the cellulose dispersion, 10% by weight or less of the particles are not precipitated at the centrifugal condition of centrifugal force of 4900 M/s$^2$.

When the average particle size of the primary cellulose particles become 50 μm or larger, the secondary aggregate structure is hard to form even if the shape of the primary cellulose particles is in the specific range, and the primary particles are dried individually and this is not preferable in the aspect of the intraparticular pore volume. Further the apparent specific volume becomes too large and this is not preferable in the aspect of the fluidity.

When the average particle size of the primary cellulose particles is 10 μm or less, the inter-particular bonding force is too strong when the particles form the secondary aggregate structure and this is not preferable in the aspect of disintegration property. When the average width of the primary cellulose particles exceeds 30 μm, the primary cellulose particles become difficult to bend, and the entanglement between neighboring primary cellulose particles is decreased, and this is not preferred in the aspect of the intraparticular pore volume. When the average width of the primary cellulose particles is less than 2 μm, the particles aggregate densely and the intraarticular pores are not formed. This is not preferred because the compactibility and disintegration property are worsened. When the average thickness of the primary cellulose particles is over 5 μm, the primary cellulose particles become difficult to bend, and the entanglement between neighboring primary cellulose particles is decreased, and this is not preferred in the aspect of the intraparticular pore volume. The lower limit of the average thickness of the primary cellulose particles is the lower, the easier it is for the particles to entangle, and this is preferable in the aspect of the intraparticular pore volume, but this is at most about 0.5 μm. When the width of the primary cellulose particles is less than 2 μm and the thickness is less than 0.5 μm, such fine particles are bound tightly, and the intraparticular pore volume becomes small and thus this is not preferred because of poor compactibility and disintegration property.

The primary cellulose particles are preferably used which has a particle shape having the ratio of the average values of the major axis and minor axis (L/D) of 2.0 or above. The larger is the L/D, the more effective it is in inhibiting excessive particle aggregate in drying, and this contributes to give a larger pore volume in the particles.

The cellulose dispersion of the present invention is not particularly restricted and may be produced by any one of the methods selected from i) a method for producing the cellulose dispersion using the primary cellulose particles by treating one or plurality of natural cellulose substances, ii) a method for producing the cellulose dispersion by dividing the cellulose dispersion of the aforementioned i), treating separately and then mixing, iii) a method for producing the cellulose dispersion by fractionating the cellulose dispersion of the aforementioned i) or ii), treating them separately and then mixing again or iv) a method for producing the cellulose dispersion by mixing two or more groups of the primary cellulose particles prepared separately, and from the economical point of view i) is especially preferable. The treatment method used here may be a wet method or a dry method, or respective products obtained by the wet method may be mixed before drying, or respective products obtained by the dry method may be mixed before drying or products obtained by the wet method and dry method may be combined. The treatment method may be a publicly known method and the like, and not particularly restricted, including, for example, a mechanical treatment such as milling and grinding, and a separation treatment such as centrifugal separation using a cyclone or a centrifuge and sieving using a thieve. The method may be used singly or in combination of both methods.

The grinding method may be a grinding method using the stirring blade of the one-way rotating, multi-shaft rotary, reciprocating/reversing, vertically moving, rotating+vertically moving, or duct type such as a portable mixer, a spatial mixer, a side mixer, or the like, a jet-type stirring/grinding method such as a line mixer, a grinding method using a high-shear homogenizer, a high-pressure homogenizer, an ultrasonic homogenizer, or the like; or a grinding method using a rotating axis extrusion kneader. The milling method to be used may be any one of: a screen milling method such as a screen mill and hammer mill; a rotating blade shear screen milling method such as a flush mill; a jet milling method such as a jet mill; a ball milling method such as a ball mill, vibration ball milling; a screw type stirring milling method; and the like.

The cellulose dispersion particle mixture obtained by the aforementioned procedure is preferably made into a dispersion of a concentration of 5-40% by weight before drying. If the concentration is less than 5% by weight, the average particle size of the cellulose particles to be obtained decreases and the self-fluidity tends to be impaired. Also, if this concentration is over 40% by weight, the apparent specific volume of the cellulose particles becomes smaller and the compression compactibility tends to be impaired. The preferable concentration is 10-40% by weight and the more preferable concentration is 15-40% by weight.

The drying method is not particularly restricted and any method such as freeze drying, spray drying, drum drying, shelf drying, air stream drying and vacuum drying may be used, and a single method or a combination of two or more methods may be used. The spray method in performing spray drying may be any of the method selected from the disc spray, pressurized nozzle, pressurized two fluid nozzle and pressurized four fluid nozzle, and a single method or a combination of two or more methods may be used. From the economical point of view, the spray drying is preferable.

On performing the aforementioned spray drying, a minute amount of a water soluble macromolecule or surfactant may be added to the dispersion to reduce the surface tension, and a foaming agent or a gas may be added to the dispersion to accelerate the vaporization rate of the medium.

The water soluble macromolecule includes water soluble macromolecules described in "Pharmaceutical additives" (published by Yakuji Nippo Limited.) such as hydroxypropyl cellulose, hydroxypropyl methylcellulose, polyacrylic acid, carboxyvinyl polymer, polyethylene glycol, polyvinyl alcohol, polyvinyl pyrrolidone, methylcellulose, gum Arabic and starch glue, and one kind may be used alone or a combination of two kinds or more may be used.

The surfactant includes surfactants classified as such in "Pharmaceutical additives" (published by Yakuji Nippo Limited.), for example, phospholipids, glycerin fatty acid ester, polyethylene glycol fatty acid ester, sorbitan fatty acid ester, polyoxyethylene hardened caster oil, polyoxyethylenecetyl ether, polyoxyethylene stearyl ether, polyoxyethylenenonylphenyl ether, polyoxyethylenepolyoxypropylene glycol, polyoxyethylenesorbitan monolaurate, polysorbate, sorbitan monooleate, glyceride monostearate, monooxyethylenesorbitan monoparmitate, monooxyethylenesorbitan monostearate, polyoxyethylenesorbitan monooleate, sorbitan monopalmitate, sodium laurylsulfate, and these are used alone or a combination of two kinds or more may be used freely.

The foaming agent includes foaming agents described in "Pharmaceutical additives" (published by Yakuji Nippo Limited.), for example, tartaric acid, sodium bicarbonate, potato starch, anhydrous citric acid, medicinal soap, sodium laurylsulfate, lauric diethanolamide, macrogoallaurate, and one kind may be used alone or a combination of two kinds or more may be used. Also, other than the pharmaceutical additives, bicarbonate such as sodium bicarbonate and ammonium bicarbonate that generate gas by pyrolysis, and carbonates such as sodium carbonate and ammonium carbonate that generate gas by reacting with acids may be used. However, when carbonates described above are to be used, an acid must be used together. The acid includes: organic acids such as citric acid, acetic acid, ascorbic acid, adipic acid; protonic acids such as hydrochloric acid, sulfuric acid, phosphoric acid and nitric acid; Lewis acids such as boron fluoride, and the one used for pharmaceuticals/foods is preferred but others have the similar effect. In place of the foaming agent, gases such as nitrogen, carbon dioxide, liquefied petroleum gas and dimethyl ether may impregnate the dispersion.

These water soluble macromolecules, surfactants and gas generating substances may be added before drying and the timing of addition is not particularly restricted.

The compacting composition in the present invention may contain one kind or more of the active ingredients and the porous cellulose aggregate of the present invention, and the amount is not particularly restricted, but normal range of the usage is 0.001-99% for the active ingredient and 1-99% for the cellulose powder of the present invention. Further, it can be processed by publicly known methods such as mixing, stirring, granulating, regulating particle size and pressing tablet. When the active ingredient is less than 0.001%, the effective dosage for treatment cannot be obtained, and at over 99%, the porous cellulose aggregate of the present invention is less than 1% and the molded body having practical hardness, friability and disintegration property is difficult to obtain. The compacting composition of the present invention can freely contain not only an active ingredient and cellulose particles but also optionally an excipient, disintegrator, binder, fluidizer, lubricant, tasting agent, flavoring agent, coloring agent, sweetener.

Examples of the compacting composition of the present invention for pharmaceutical use include tablets, powder, fine granules, granules, extracts and pills. The present invention includes the compacting compositions used for not only pharmaceuticals but also foods such as sweets, health foods, taste improvers, dietary fiber supplements and cosmetic solid foundations, bathing agents, veterinary drugs, diagnostic agents, agricultural chemicals, fertilizers, ceramic catalysts.

The active ingredient in the present invention means pharmaceutical drug components, agricultural chemical components, fertilizer components, animal feeds components, food components, cosmetic components, dyes, flavoring agents, metals, ceramics, catalysts and surfactants, and may take any form such as solid (powder, crystalline and the like), oil, liquid or semi solid. Also a coating may be applied to control elution, reduce bitter taste and the like. The active ingredients may be used alone or in combination of a plurality of them. The active ingredient may be used by dissolving, suspending or emulsifying in a medium.

For example, a pharmaceutical drug component that is administered orally such as an antipyretic analgesic antiphlogistic, hypnotic, antisleepiness drug, antidizziness drug, pediatric analgesic, stomachic, antacid, digestive drug, cardiotonic, antiarrhythmic drug, antihypertensive, vasodilator, diuretic, antiulcer drug, intestinal regulator, antiosteoporosis drug, antitussive expectorant, antiasthmatic drug, antibacterial drug, anti-pollakiuria drug, analeptic and vitamin can be the active ingredient. The drug component can be used alone or in combination of two kinds or more freely.

The pharmaceutical active ingredient of the present invention includes pharmaceutical drug components described in "Pharmacopeia of Japan", "Rule for Unofficial Drugs", "USP", "NF", "EP", such as aspirin, aspirin aluminum, acetaminophen, ethenzamide, salicylosalicylic acid, salicylamide, lactyl phenetidine, isothibenzyl hydrochloride, diphenylpyraline hydrochloride, diphenhydramine hydrochloride, difeterol hydrochloride, triprolidine hydrochloride, tripelennamine hydrochloride, thonzylamine hydrochloride, fenethazine hydrochloride, methdilazine hydrochloride, diphenhydramine salicylate, carbinoxamine diphenyldisulfonate, alimemazine tartarate, diphenehydramine tannate, diphenylpyraline theoclate, mebhydrolin napadisilate, promethazinemethylene disalicylate, carbinoxamine maleate, dl-chlorpheniramine maleate, dl-chlorpheniramine maleate, difeterol phosphate, alloclamide hydrochloride, cloperastine hydrochloride, petoxyverine citrate (carbetapentane citrate), tipepidine citrate, sodium dibunate, dextromethorphan hydrobromide, dextromethorphan phenolphthalinate, tipepidine hibenzate, cloperastine fendizoate, codeine phosphate, dihydrocodeine phosphate, noscapine hydrochloride, noscapine, dl-methylephedrine hydrochloride, dl-methylephedrine saccharin salt, guaiacol potassium sulfonate, guaifenesin, caffeine sodium benzoate, caffeine, anhydrous caffeine, vitamin B1 and derivatives and salts thereof, vitamin B2 and derivatives and salts thereof, vitamin C and derivatives and salts thereof, hesperidine and derivatives and salts thereof, vitamin B6 and derivatives and salts thereof, nicotinamide, calcium pantothenate, aminoacetic acid, magnesium silicate, synthetic aluminum silicate, synthetic hydrotalcite, magnesium oxide, dihydroxy aluminum aminoacetate (aluminum glycinate), aluminum hydroxide gel (as dried aluminum hydroxide gel), dried aluminum hydroxide gel, dried mixed gel of aluminum hydroxide/magnesium carbonate, co-precipitates of aluminum hydroxide/sodium bicarbonate, co-precipitates of aluminum hydroxide/calcium carbonate/magnesium carbonate, co-precipitates of magnesium hydroxide/aluminum potassium sulfate, magnesium carbonate, magnesium aluminometa silicate, ranitidine hydrochloride, cimetidine, famotidine, naproxen, dichlophenac sodium, piroxicam, azulene, indomethacin, ketoprofen, ibuprofen, difenidol hydrochloride, diphenylpyraline hydrochloride, diphenhydramine hydrochloride, promethazine hydrochloride, meclizine hydrochloride, dimenhydrinate, diphenhydramine tannate, phenetazine tannate, diphenylpyraline theoclate, diphenhydramine fumarate, promethazinemethylene disalicylate, spocolamine hydrobromide, oxyphencyclimine hydrochloride, dicyclomine hydrochloride, methixene hydrochloride, atropine methylbromide, anisotropine methylbromide, spocolamine methylbromide, methyl bromide-1-hyoscyamine, benactizium methylbromide, belladonna extract, isopropamide iodide, diphenylpiperidinomethyldioxolan iodide, papaverine hydrochloride, aminobenzoic acid, cesium oxalate, ethyl piperidylacetylaminobenzoate, aminophylline, diprophylline, theophylline, sodium bicarbonate, fursultiamine, isosorbide nitrate, ephedrine, cephalexin, ampicillin, sulfixazole, sucralfate, allylisopropylacetylurea, bromovalerylurea or the like, and ephedra herb, nandia fruit, cherry bark, polygala root, glycyrrhiza, platycodon root, plantago seed, plantago herb, senega, fritillaria, fennel, phellodendron bark, coptis rhizome, zedoary, german camomile, cinnamon bark, gentiana, oriental bezoar, animal bile, ladybells, ginger, atractylodes lancea rhizome, citrus unshiu peel, atractylodes rhizome, earthworm, panax rhizome, ginseng, kanokoso, moutan bark, zanthoxylum fruit, and extracts thereof, and insulin, vasopressin, interferon, urokinase, serratiopeptidase and somatostatin. One kind selected from the above group may be used alone or in a combination of two or more.

The active ingredient hard to be soluble in water in the present invention means, for example, a pharmaceutical active ingredient, one gram of which requires 30 ml or more water to dissolve according to the 14$^{th}$ edition Japanese Pharmacopeia. If it is hard to be soluble in water, the effect can be obtained by compounding as an active ingredient to the composition of the present invention regardless of the extent of its sublimatablity or surface polarity.

The solid active ingredient hard to be soluble in water includes pharmaceutical drug components described in "Pharmacopeia of Japan", "Rule for Unofficial Drugs", "USP", "NF", "EP", such as: antipyretic analgesics, drugs for nervous system, sedative hypnotic drugs, muscle relaxant, antihypertensive drugs, anti-histamine drugs, such as acetaminophen, ibuprofen, benzoic acid, ethenzamide, caffeine, camphor, quinine, calcium gluconate, dimethyl caprol, sulfamin, theophylline, theopromine, riboflavin, mephenesin, phenobarbital, aminophyllin, thioacetazone, quercetin, rutin, salicylic acid, sodium theophyllinate, pyrapital, quinine HCl, irgapirin, digitoxin, griseofulvin and phenacetin; antibiotics such as acetylspiramycin, ampicillin, erythromycin, xatamycin, chloramphenicol, triacetyloleandomycin, nystatin and colistin sulfate; steroid hormones such as methyltestesterone, methyl-androsterone-diol, progesterone, estradiol benzoate, ethinyl estradiol, deoxycorticosterone acetate, cortisone acetate, hydrocortisone, hydrocortisone acetate and prednisolone; non-steroid progestogen such as dienestrol, hexastrol, diethylstillbesterol, diethylstillbesterol propionate, chlorotrianisene; and other lipid soluble vitamins, and one kind selected from the above group may be used alone, or a combination of two kinds or more may be used freely.

The oily or liquid active ingredient hard to be soluble in water used in the present invention includes pharmaceutical drug components described in "Pharmacopeia of Japan", "Rule for Unofficial Drugs", "USP", "NF", "EP", for example: vitamins such as teprenone, indomethacin-farnesyl, menatetrenone, phytonadione, vitamin A oil, fenipentol, vitamin D and vitamin E; highly unsaturated fatty acids such as DHA (docosahexaenoic acid), EPA (Eicosapentaenoic acid) and cod liver oil; coenzyme Qs; lipid soluble flavoring agents such as orange oil, lemon oil and peppermint oil. Vitamin E has various isomers and derivatives, but is not particularly restricted as long as they are liquid at normal temperature. For example, dl-α-tocopherol, dl-α-tocopherol acetate, d-α-tocopherol and d-α-tocopherol acetate are included, and one kind selected from the above group may be used alone or in a combination of two or more kinds may be used freely.

The semisolid active ingredient hard to be soluble in water include for example: Chinese medicines or herbal extracts such as earthworm, glycyrrhiza, cinnamon bark, peony root, moutan bark, Japanese valerian, zanthoxylum fruit, ginter, citrus unshiu peel, ephedra herb, nandia fruit, cherry bark, polygala root, platycodon root, plantago seed, plantago herb, red spider lily, senega, fritillaria, fennel, phellodendron bark, coptis rhizome, zedoary, german camomile, gentiana, oriental bezoar, animal bile, ladybells, ginger, atractylodes lancea rhizome, clove, chinhi, atractylodes rhizome, panax rhizome, ginseng, kakkonto, keishito, kososan, saikeishito, shosaikoto, shoseiryuto, bakumondoto, hangekobokuto and Maoto; oyster extract, propolis and propolis extract and coenzyme Qs, and one kind selected from the above group may be used alone or in a combination of two or more kinds may be used freely. The solid formulation composition of the present invention may further contain other physiologically active components in addition to the water insoluble active ingredients described above.

The finely ground active ingredient used in the present invention means the one finely ground to 1-40 μm or below for targeting to improve the dispersibility of the solid active ingredient hard to be soluble in water, the mixing uniformity of an active ingredient with pharmaceutical effect even in a small amount and the like. The smaller is the average particle size, the greater is the effect of the present invention. More preferable average particle size of the active ingredient is 1-20 μm and still more preferable diameter is 1-10 μm.

The sublimatable active ingredient of the present invention is not particularly restricted as long as it is sublimatable, and may be solid, liquid or semi solid at normal temperature.

The sublimatable active ingredient includes sublimatable pharmaceutical drug components described in "Pharmacopeia of Japan", "Rule for Unofficial Drugs", "USP", "NF", "EP", for example, benzoic acid, ethenzamide, caffeine, camphor, salicylic acid, phenacetin and ibuprofen. One kind selected from the above group may be used alone or combination of two or more may be used freely. The solid formulation composition of the present invention may further contain other physiologically active components in addition to the sublimative active ingredients described above.

The liquid active ingredient at normal temperature used in the present invention includes pharmaceutical drug components described in "Pharmacopeia of Japan", "Rule for Unofficial Drugs", "USP", "NF", "EP", for example: vitamins such as teprenone, indomethacin-farnesyl, menatetrenone, phytonadione, vitamin A oil, fenipentol, vitamin D and vitamin E; highly unsaturated fatty acids such as DHA (docosahexaenoic acid), EPA (Eicosapentaenoic acid) and cod liver oil; coenzyme Qs; lipid soluble flavoring agents such as orange oil, lemon oil and peppermint oil. Vitamin E has various isomers and derivatives, but is not particularly restricted as long as they are liquid at normal temperature. For example, dl-α-tocopherol, dl-α-tocopherol acetate, d-α-tocopherol and d-α-tocopherol acetate are included, and one kind selected from the above group may be used alone or a combination of two or more kinds may be used freely.

The semisolid active ingredient at normal temperature used in the present invention include for example: Chinese medicines or herbal extracts such as earthworm, glycyrrhiza, cinnamon bark, peony root, moutan bark, Japanese valerian, zanthoxylum fruit, ginter, citrus unshiu peel, ephedra herb, nandia fruit, cherry bark, polygala root, platycodon root, plantago seed, plantago herb, red spider lily, senega, fritillaria, fennel, phellodendron bark, coptis rhizome, zedoary, german camomile, gentiana, oriental bezoar, animal bile, ladybells, ginger, atractylodes lancea rhizome, clove, chinhi, atractylodes rhizome, panax rhizome, ginseng, kakkonto, keishito, kososan, saikeishito, shosaikoto, shoseiryuto, bakumondoto, hangekobokuto and Maoto; oyster extract, propolis and propolis extract and coenzyme Qs, and one kind selected from the above group may be used alone or a combination of two or more kinds may be used freely.

The excipient includes excipients classified as such in "Pharmaceutical additives" (published by Yakuji Nippo Limited.) such as, starch acrylate, L-aspartic acid, aminoethylsulfonic acid, aminoacetic acid, molasses (powder), gum Arabic, gum Arabic powder, alginic acid, sodium alginate, gelatinized starch, pumice particles, inositol, ethylcellulose, ethylene-vinylacetate copolymer, sodium chloride, olive oil, kaolin, cacao butter, casein, fructose, pumice particles, carmellose, carmellose sodium, hydrated silicone dioxide, dried yeast, dried aluminum hydroxide gel, dried sodium sulfate, dried magnesium sulfate, agar, agar powder, xylitol, citric acid, sodium citrate, disodium citrate, glycerin, calcium glycerophosphate, sodium gluconate, L-glutamine, clay, clay 3, clay particles, croscarmellose sodium, crospovidone, magnesium aluminosilicate, calcium silicate, magnesium silicate, light anhydrous silicate, light liquid paraffin, cinnamon powder, crystalline cellulose, crystalline cellulose carmellose sodium, crystalline cellulose (particles), genmaikoji, synthetic aluminum silicate, synthetic hydrotalcite, sesame oil, wheat flour, wheat starch, wheat germ flour, rice flour, rice starch, potassium acetate, calcium acetate, cellulose acetate phthalate, safflower oil, bleached beeswax, zinc oxide, titanium oxide, magnesium oxide, β-cyclodextrin, dihydroxyaluminum aminoacetate, 2,6-di-butyl-4-methylphenol, dimethylpolysiloxane, tartaric acid, potassium hydrogen tartrate, burnt gypsum, sucrose fatty acid ester, magnesium-aluminum hydroxide, aluminum hydroxide gel, co-precipitates of aluminum hydroxide/sodium bicarbonate, magnesium hydroxide, squalane, stearyl alcohol, stearic acid, calcium stearate, polyoxyl stearate, magnesium stearate, hardened soybean oil, purified gelatin, purified shelac, purified white sugar, purified granule sugar, cetostearyl alcohol, polyethylene glycol 1000 mono cetyl ether, gelatin, sorbitan fatty acid ester, D-sorbitol, tricalcium phosphate, soybean oil, unsaponified soybean product, soybean lecithin, defatted powdered milk, talc, ammonium carbonate, calcium carbonate, magnesium carbonate, neutral anhydrous sodium sulfate, low substitution hydroxypropyl cellulose, dextran, dextrin, natural aluminum silicate, corn starch, tragacanth powder, silicon dioxide, calcium lactate, lactose, granular lactose, Perfiller 101, white shellac, white vaseline, white clay, white sugar, white sugar/starch granule, powder of green leaf extract of rye, dried powder of green juice of bud leaf of rye, honey, paraffin, potato starch, half digested starch, human serum albumin, hydroxypropylstarch, hydroxypropylcellulose, hydroxypropylcellulose, hydroxypropylmethylcellulose phthalate, hydroxypropylmethylcellulose phthalate, phytic acid, glucose, glucose hydrate, partially gelatinized starch, pullulan, propylene glycol, reduced maltose molasses powder, powdered cellulose, pectin, bentonite, sodium polyacrylate, polyoxyethylenealkyl ether, polyoxyethylene hardened caster oil, polyoxyethylene (105) polyoxypropylene (5) glycol, polyoxyethylene (160) polyoxypropylene (30) glycol, sodium polystyrenesulfonate, polysorbate 80, polyvinyl acetal diethylamino acetate, polyvinyl pyrrolidone, polyethyleneglycol, maltitol, maltose, D-mannitol, molasses, isopropyl myristate, anhydrous lactose, anhydrous calcium hydrogen phosphate, granular anhydrous calcium hydrogen phosphate, magnesium aluminometa silicate, methylcellulose, cotton seed powder, cotton seed oil, wood wax, aluminum monostearate, glycerin monostearate, sorbitan monostearate, medical charcoal, peanut oil, aluminum sulfate, calcium sulfate, granular corn starch, liquid paraffin, dl-malic acid, calcium monohydrogen phosphate, calcium hydrogen phosphate, granular calcium hydrogen phosphate, sodium hydrogen phosphate, potassium dihydrogen phosphate, calcium dihydrogen phosphate and sodium dihydrogen phosphate, and one kind selected from the above group may be used alone or a combination of two or more kinds may be used freely.

The disintegrator includes integrators classified as such in "Pharmaceutical additives" (published by Yakuji Nippo Limited.) for example: celluloses such as, croscarmellose sodium, carmellose, carmellose calcium, carmellose sodium and low substitution hydroxypropylcellulose; starches such as carboxymethylstarch sodium, hydroxypropylstarch, rice starch, wheat starch, corn starch, potato starch and partially gelatinized starch; and synthetic polymers such as crospovidone and crospovidone co-polymer. One kind selected from the above group may be used alone or a combination of two or more kinds may be used freely.

The binder includes binders classified as such in "Pharmaceutical additives" (published by Yakuji Nippo Limited.) for example: sugars such as white sugar, glucose, lactose and fructose; sugar alcohols such as mannitol, xylitol, maltitol, erythritol and sorbitol; water soluble polysaccharides such as gelatin, pullulan, carrageenan, locust bean gum, agar, glucomannan, xanthan gum, tamarindo gum, pectin, sodium alginate and gum Arabic; celluloses such as crystalline cellulose, powdered cellulose, hydroxypropylcellulose and methylcellulose; starches such as gelatinized starch and starch glue; synthetic polymers such as polyvinyl pyrrolidone, carboxyvinyl polymer and polyvinyl alcohol; and inorganic compounds such as calcium hydrogen phosphate, calcium carbonate, synthetic hydrotalcite and magnesium aluminosilicate. One kind selected from the above group may be used alone or a combination of two or more kinds may be used freely.

The fluidizing agent includes fluidizing agents classified as such in "Pharmaceutical additives" (published by Yakuji Nippo Limited.) for example silicon compounds such as hydrated silicon dioxide and light anhydrous silicate. One kind selected from the above group may be used alone or a combination of two or more kinds may be used freely.

The lubricant includes lubricants classified as such in "Pharmaceutical additives" (published by Yakuji Nippo Limited.) for example magnesium stearate, calcium stearate, stearic acid, sucrose fatty acid ester and talc. One kind selected from the above group may be used alone or a combination of two or more kinds may be used freely.

The tasting agent includes tasting agents classified as such in "Pharmaceutical additives" (published by Yakuji Nippo Limited.) for example glutamic acid, fumaric acid, succinic acid, citric acid, sodium citrate, tartaric acid, malic acid, ascorbic acid, sodium chloride and l-menthol. One kind selected from the above group may be used alone or a combination of two or more kinds may be used freely.

The flavoring agent includes flavoring agents classified as such in "Pharmaceutical additives" (published by Yakuji Nippo Limited.) for example oils such as orange, vanilla, strawberry, yogurt, menthol, fennel oil, cinnamon oil, picea oil and peppermint oil, green tea powder. One kind selected from the above group may be used alone or a combination of two or more kinds may be used freely.

The dye includes dyes classified as such in "Pharmaceutical additives" (published by Yakuji Nippo Limited.), for example, food dyes such as food dye red No. 3, Food dye yellow No. 5, food dye blue No. 1, copper chlorophyn sodium, titanium oxide and riboflavin. One kind selected from the above group may be used alone or a combination of two or more kinds may be used freely.

The sweetener includes sweeteners classified as such in "Pharmaceutical additives" (published by Yakuji Nippo Limited.) for example aspartame, saccharin, dipotassium glycyrrhizinate, stebia, maltose, maltitol, morasses and powder of *Hydrangea macrophylla* var. *thunbergii*. One kind selected from the above group may be used alone or a combination of two or more kinds may be used freely.

Following is the description of the method for production of the tablets, the main components of which are one or plurality of active ingredients and the porous cellulose aggregates of the present invention, but this is an example and the effect of the invention is not limited by the following method. The method can be used including a step of mixing an active ingredient and the porous cellulose aggregates of the present invention and then a step of compression compacting. During these steps additives other than the active ingredient can be mixed optionally, and one or more kind of the components for example selected from the group shown above such as excipients, disintegrators, binders, fluidizers, lubricants, tasting agents, flavors, dyes, sweeteners and solubilizers may be added.

The order of the addition of the respective components is not particularly restricted, and any of the method may be used, i) by which the active ingredient, the porous cellulose aggregates of the present invention and optionally other additives are mixed altogether and subjected to compression compacting or ii) by which the active ingredient, and the additives such as the fluidizer and/or lubricant are pre-mixed and then mixed with the porous cellulose aggregates of the present invention and, optionally, with other additives, and subsequently the mixture is subjected to compression compacting. The lubricant may be added to the powder mixture for compression compacting obtained in i) or ii), mixing is continued and then the mixture may be subjected to compression compacting.

When an active ingredient hard to be soluble in water is especially used, the following production method can be used. The production methods, for example, may be any of, the methods: i) by which the active ingredient is ground or used as it is, mixed with the porous cellulose aggregates of the present invention and optionally with the other additives, and then the mixture is subjected to compression compacting, or ii) by which, after dissolving or dispersing the active ingredient in water and/or an organic solvent and/or a solubilizer, the solution or dispersion is absorbed to the porous cellulose aggregate of the present invention and/or optionally to the other additives, and mixed with the porous cellulose aggregate and/or optionally with the other additives, and after distilling off water and/or the organic solvent optionally, the mixture is subjected to compression compacting.

Among i), in particular, it is preferable from the view point of compactibility and fluidity that after mixing an active ingredient with additives such as a fluidizer in advance, the active ingredient is mixed with the porous cellulose aggregates of the present invention and optionally with other components and subjected to compression compacting. The crystalline form of the active ingredient before compression compacting may be the same or different from that before the formulation, it is preferable to be the same from the view point of the stability. When using a water insoluble active ingredient, it is effective to use a water soluble polymer or surfactant in combination especially as a solubilizer to disperse the active ingredient into the medium. Here, the other additive means an additive other than the porous cellulose aggregates of the present invention, including, for example, the aforementioned excipients, disintegrators, binders, fluidizers, lubricants, tasting agents, flavors, sweeteners and solubilizers. These additives may be used alone or in a combination of two or more kinds.

In the cases of ii) in particular, since the active ingredient that is hard to be soluble or insoluble in water goes through a step of solubilization or dispersion once, an improving effect for the elution of the active ingredient can be expected. When a liquid dispersion medium such as polyethylene glycol is used in combination as a dispersion medium for a pharmaceutical active ingredient, the dispersed becomes liquid or semi-solid even if the active ingredient is originally a crystalline powder, and thus tablet formulation therefrom is impossible unless a substance such as the porous cellulose aggregate of the present invention having superior compression compactibility and fluidity is used. Further, when polyethylene glycol or the like is used as a dispersing agent for a pharmaceutical active ingredient, it is said that the active ingredient absorbed in the body takes a structure covered by polyethylene glycol in the blood stream, and thus it is expected that the effect of the active ingredient that is easily metabolized in the liver lasts longer.

A method for adding each component is not particularly restricted if it is commonly practiced method, and either the continuous addition or one time addition may be performed using a small suction transport device, air transport device, bucket conveyer, pressure transport device, vacuum conveyer, quantitative vibration feeder, spray, funnel and the like.

When the active ingredient is a solution, suspension or emulsion, it is preferable to adopt a method of spraying that to the porous cellulose aggregates of the present invention or to the other additive because it reduces the variation of the concentration of the active ingredient in the final products. The spray method may be any methods for spraying the solution/dispersion of the active ingredient using a pressure nozzle, 2-fluid nozzle, 4-fluid nozzle, rotating disc, ultrasonic nozzle or the like, or methods for instilling the solution/dispersion of the active ingredient from a tube like nozzle. When the solution/dispersion of the active ingredient is added, the active ingredient may be layered on the surface of the porous cellulose aggregate particles by layering or coating treatment, may be held inside of the porous cellulose aggregate particles, or the solution/dispersion of the active ingredient may be used as a binding agent for granulating the porous cellulose aggregate particles or a mixture of the porous cellulose and the other additives in a matrix-like structure. The layering and coating treatment may be performed by a wet method or a dry method.

A method for mixing is not particularly restricted if it is a commonly practiced method, and it may use a vessel rotation type mixer such as a V type, W type, double corn type, or container tack type mixer, a stirring mixer such as a high-speed agitation type, universal agitation type, ribbon type, pug type, or nautor type mixer, a super mixer, a drum type mixer, or a fluidized bed type mixer. In addition, a vessel shaking type mixer such as a shaker may be also used.

A method for the compression compacting of the composition is not particularly restricted if it is a commonly practiced method; a method which includes using a die and a punch for making the composition into a desired form by means of the compression compacting or a method which includes preliminarily making the composition into sheet form by means of the compression compacting, and cutting into a desired form may be used. A compression compacting machine may use, for example, a roller type press such as a hydrostatic press, a briquetting roller type press, or a smoothing roller type press, or a compressor such as a single-punch tableting machine or a rotary tableting machine.

A method for dissolving or dispersing an active ingredient in a medium is not particularly restricted if it is carried out by the usual dissolution or dispersion method; a stirring/mixing method such as a portable mixer, a spatial mixer, a side mixer, or the like using the stirring blade of the one-way rotating, multi-shaft rotary, reciprocating/reversing, vertically moving, rotating+vertically moving, or duct type, a jet-type stirring/mixing method such as a line mixer, a gas-blowing stirring/mixing method, a mixing method using a high-shear homogenizer, a high-pressure homogenizer, an ultrasonic homogenizer, or the like, or a mixing method of vessel shaking type using a shaker, or the like may be used.

A solvent used in the production method described above is not particularly restricted if it is used for pharmaceuticals and includes solvents classified as such in "Pharmaceutical additives" (published by Yakuji Nippo Limited.), for example, alcohols such as methanol, ethanol, isopropyl alcohol, butyl alcohol, 2-methylbutyl alcohol and benzyl alcohol, hydrocarbons such as pentane, hexane, heptane and cyclohexane, ketones such as acetone and ethylmethylketone, and one kind selected from the above group may be used alone or a combination of two or more kinds may be used freely, or after dispersing with one kind of solvent, the solvent may be removed and another solvent may be used for dispersion.

A water soluble polymer as a solubilizer includes water soluble polymers described in "Pharmaceutical additives" (published by Yakuji Nippo Limited.), for example, hydroxypropylcellulose, hydroxypropylmethylcellulose, polyacrylic acid, carboxyvinylpolymer, polyethylene glycol, polyvinyl alcohol, polyvinyl pyrrolidone, methylcellulose, ethylcellulose, gum Arabic and starch glue, and these may be used alone or in a combination of two or more freely.

Fat and oils as a solubilizer include fat and oils described in "Pharmaceutical additives" (published by Yakuji Nippo Limited.), for example, monoglyceride stearate, triglyceride stearate, sucrose stearate ester, paraffins such as liquid paraffin, carnauba wax, hardened oils such as hardened castor oil, castor oil, stearic acid, stearyl alcohol and polyethyleneglycol; these may be used alone or in a combination of two or more kinds freely.

A surfactant as a solubilizer may be, for example, those classified as a surfactant in "Pharmaceutical additives" (published by Yakuji Nippo Limited.), including phospholipid, glycerin fatty acid ester, polyethylene glycol fatty acid ester, sorbitan fatty acid ester, polyoxyethylene hardened castor oil, polyoxyethylene cetyl ether, polyoxyethylene stearyl ether, polyoxyethylene nonylphenyl ether, polyoxyethylene polyoxypropylene glycol, polyoxyethylene sorbitan monolaurate, polysorbate, sorbitan monooleate, glyceride monostearate, monooxyethylene sorbitan monopalmitate, monooxyethylene sorbitan monostearate, polyoxyethylene sorbitan monooleate, sorbitan monopalmitate, and sodium lauryl sulfate; these may be used alone or in a combination of two or more kinds.

As used herein, "tablet" refers to a molded body obtained by compression compacting that includes the porous cellulose aggregates of the present invention, one or more active ingredients, and optionally other additives. A composition for a tablet, formulated with the porous cellulose aggregates of the present invention has practical hardness obtained by a simple and easy method such as direct tablet pressing without going through a complex process; however, any preparation method including a dry granule compression method, a wet granule compression method, wet granulation compression (extragranular addition of microcrystalline cellulose), or a method for preparing a multicore tablet using, as inner core, a tablet preliminarily subjected to compression compacting a method for preparing a multi-layer tablet by stacking molded bodies preliminarily subjected to compression compacting and compressing them again may be also used.

Since the porous cellulose aggregates of the present invention is superior in various physical properties required for an excipient such as compression compactibility, self fluidity and disintegration property, it is effectively used for: tablets containing many kinds and a large quantity of drugs, which tend to cause tablet pressing troubles such as lowering of tablet hardness, fractures on the surface of the tablet, chipping, peeling off from inside and cracking, for example, the tablets for over-the-counter drugs and tablets containing extract powder such as Chinese herb medicine; small tablets; non-cylinder type odd shaped tablets having a part where compression pressure is difficult to be applied homogeneously such as a constricted edge; tablets containing drugs like enzymes/proteins that are easily inactivated by tabletting pressure or friction with the excipient; and tablets containing coated granules. In addition, since the cellulose powder of the present invention is superior in compression compactibility and disintegration property, tablets having a practical friability can be obtained at a relatively low compression pressure. For that reason, gaps (watering capillary) can be maintained in the tablet, it is effectively used for tablets that disintegrate quickly in the oral cavity.

Further, for multi-layer and multi-core tablets in which several components of the composition are compression molded in one or multi-steps, the porous cellulose aggregates of the present invention is effective, in addition to preventing the general tablet pressing troubles described above, in preventing peeling between the layers and cracks. Having a secondary aggregate structure that is formed by the aggregation of the primary particles, the porous cellulose aggregates of the present invention has a good cleavability of the particle itself, and when used in a scored tablet, it is easy to cleave the tablet evenly. Still further, having a well developed porous structure, the porous cellulose aggregates of the present invention has a good retention of drugs in a fine particulate condition, in a suspension liquid and in solubilized solution, and thus the tablets utilizing these have also a good retention of drugs in a fine particulate condition, in a suspension liquid and in solubilized solution. Therefore it is effectively used for preventing the peeling off and strengthening of layering the coating layer and sugar coat layer of layering and coating tablets which are treated with components in suspended liquid or solution, and also sugar coated tablets on which components such as sugar and calcium carbonate are layered.

Next, the usage of a composition containing one kind or more of the active ingredients and the porous cellulose aggregate particles will be described. The compositions that are obtained by the method described above containing solid, liquid and semisolid active ingredients and the porous cellulose aggregate particles may be used as a solid formulation in powder or granular conditions, or as coated powder or granular solid formulation by treating the powder or granular composition with a coating agent. The powder or granular composition with or without coating may be used by filling in a capsule or may be used as a tablet type solid formulation by treating by the compression compacting procedure. Still further capsules or tablets may be used after coating.

Here, a coating agent for applying a coating includes coating agents described in "Pharmaceutical additives" (published by Yakuji Nippo Limited.), for example, a dispersion of ethyl acrylate/methyl methacrylate copolymer, acetyl glycerin fatty acid ester, aminoalkyl methacrylate copolymer, gum Arabic powder, ethylcellulose, aqueous dispersion of ethylcellulose, octyl-decyl triglyceride, olive oil, kaolin, coca butter, kagoso, castor wax, caramel, carnauba wax, carboxyvinyl polymer, carboxymethylethylcellulose, carboxymethylstarch sodium, calcium carmellose, sodium carmellose, hydrated silicon dioxide, dried aluminum hydroxide gel, dried milky white lac, dried methacrylate copolymer, Kanbai powder (rice granules), fish scale powder, gold foil, silver foil, triethyl citrate, glycerin, glycerin fatty acid ester, magnesium silicate, light anhydrous silicic acid, light anhydrous silicic acid containing hydroxypropylcellulose, light liquid paraffin, whale wax, crystalline cellulose, hardened oil, synthetic aluminum silicate, synthetic wax, high glucose molasses, hard wax, succinylated gelatin, wheat flour, wheat starch, rice starch, cellulose acetate, vinyl acetate resin, cellulose acetate phthalate, bleached beeswax, titanium oxide, magnesium oxide, dimethylaminoethylmethacrylate/methylmetharylate copolymer, dimethylpolysiloxane, dimethylpolysiloxane/silicon dioxide mixture, silicon oxide mixture, burnt gypsum, sucrose fatty acid ester, jinko powder, aluminum hydroxide gel, hydrogenated rosin glycerin ester, stearyl alcohol, stearic acid, aluminum stearate, calcium stearate, polyoxyl stearate, magnesium stearate, purified gelatin, purified shellac, purified white sugar, zeine, sorbitan sesquioleate, cetanol, gypsum, gelatin, shellac, sorbitan fatty acid ester, D-sorbitol, D-sorbitol solution, tricalcium phosphate, talc, calcium carbonate, magnesium carbonate, simple syrup, burnt silver foil, precipitated calcium carbonate, low substituted hydroxypropylcellulose, turpentine resin, starch (soluble), corn syrup, corn oil, triacetin, calcium lactate, white shellac, white sugar, honey, hard fat, paraffin, pearl powder, potato starch, hydroxypropylcellulose, hydroxypropylcellulose, hydroxypropylcellulose acetate succinate, hydroxypropylcellulose/titanium oxide/polyethylene glycol mixture, hydroxypropylmethylcellulose phthalate, piperonyl butoxide, castor oil, diethyl phthalate, dibutyl phthalate, butylphthalylbutyl glycolate, glucose, partially gelatinized starch, fumaric acid/stearic acid/polyvinyl acetal diethylamino acetate/hydroxypropylcellulose mixture, pullulan, propylene glycose, powder sugar, bentonite, povidone, polyoxyethylene, hardened caster oil, polyoxyethylene (105) polyoxypropylene (5) glycol, polyoxyethylene (160) polyoxypropylene (30) glycol, polyoxyethylenesorbitan monostearate, polyvinyl acetal diethylaminoacetate, polyvinyl alcohol (partially saponified), polyethylene glycol, terminal hydroxyl group substituted methylpolysiloxane silicone resin copolymer, D-mannitol, molasses, beeswax, myristyl alcohol, anhydrous silicic acid hydrate, anhydrous phthalic acid, anhydrous calcium hydrogen phosphate, methacrylate copolymer, magnesium aluminometa silicate, methylcellulose, 2-methyl-5-vinylpyridinemethylacrylate/methacrylic acid copolymer, wood wax, glycerin monostearate, sorbitan monostearate, sorbitan monolaurylate, montanic acid ester wax, medical charcoal, lauromacrogol, calcium sulfate, liquid coumarone resin, liquid paraffin, dl-malic acid, calcium monohydrogen phosphate, calcium hydrogen phosphate, sodium hydrogen phosphate, calcium dihydrogen phosphate and rosin and these may be used alone or a combination of two kinds or more may be used freely.

Since the porous cellulose aggregates of the present invention have a well developed porous structure, and the particle itself has a superior retention capability, the particles that retain a drug in the pores may be used as it is as fine particles, as granules after granulation, or these may be compression molded. These fine particles, granules and tablets may be further coated thereon. The method of retention is not particularly restricted if it is a publicly known method, and may include i) a method which includes mixing with a drug in a fine particle condition and retaining in the pores, ii) a method which includes mixing the porous cellulose aggregates with a drug in a powder condition under a high shearing and forcefully retaining them in the pores, iii) a method which includes mixing the porous cellulose aggregates with a drug preliminary dissolved or dispersed, retaining them in the pores and then optionally drying for retention, iv) a method which includes mixing the porous cellulose aggregates with a sublimatable drug, and sublimating and absorbing in the pores by heating and/or reducing pressure, v) a method include mixing and fusing the porous cellulose aggregates with a drug before or during heating and retaining fused materials in the pores, and any of the above methods may be used alone or a combination of two kinds or more may be used.

Since the porous cellulose aggregates of the present invention have a well developed porous structure and have a suitable water holding capacity and oil holding capacity, they can be used not only as an excipient but also as an core particle for layering and coating, and in this usage they have an effect for preventing aggregation among the particles during the process of layering and coating. The layering and coating may be a dry method or a wet method.

Further, when an active ingredient is a solution, suspension or emulsion, a method like a dipping method, which uses the porous cellulose aggregate particles or a mixture of the porous cellulose aggregate particles and other additives as a carrier, may be used which includes immersing in the solution, suspension or emulsion of the active ingredient and retaining the active ingredient. Although it depends on the conditions such as the kind of the active ingredient and the concentration, even in the liquid immersion method such as the dipping method, the uniformity of the active ingredient can be maintained and it is superior compared to the spray method described above from the view point of the simplicity of the process.

Still further, when the active ingredient is in a solution, suspension or emulsion, a method may be adopted in which the porous cellulose aggregate particles or a mixture of the porous cellulose aggregate particles and the other additives is immersed as a carrier in the solution, suspension or emulsion of the active ingredient, and then the dispersion is spray dried to make a complex.

In the porous cellulose aggregate particles or a mixture of the porous cellulose aggregate particles and the other additives before or after the addition of an active ingredient solution/dispersion, the respective unit particles may be dispersed individually or may take a form of aggregated granules.

When the production process includes granulation, the method for granulation includes a dry granulation, wet granulation, heating granulation, spray granulation and microcapsulation. More specifically, among the wet granulation methods, fluidized bed granulation, stirring granulation, extrusion granulation, disintegration granulation and tumbling granulation are effective. In the fluidized bed granulation method, the granulation is performed in a fluidized bed granulation device by spraying the binder solution to fluidized powder. In the stirring granulation method, mixing, kneading and granulation of the powder are performed in a closed structure at the same time by rotating a stirring blade in a mixing trough while the binding solution is added. In the extrusion granulation, granulation is performed by forcefully extruding a wet lump that is kneaded by adding a binder solution through a screen of a suitable size by means of the screw method or basket method. In disintegration granulation, granulation is performed by shearing and disintegrating a wet lump that is kneaded by adding a binder solution by a rotating blade of a granulator, and spring granules out of a surrounding screen by centrifugal force. In tumbling granulation, spherical granules are tumbled by centrifugal force of a rotating rotor, and at the same time a binder solution is sprayed from a spray gun to grow the particles having a homogeneous particle size like snow balls.

Any of the methods for drying granules such as a hot air heating type (shelf drying, vacuum drying and fluidized bed drying), conduction heat type (flat pan type, shelf box type, drum type) or freeze drying type may be used. In the hot air heating type, a material is directly in contact with hot air, and at the same time evaporated water is removed. In the conduction heat type, the material is heated indirectly through a conduction wall. In freeze drying type, the material is frozen at −10 to −40° C. and then water is removed by sublimation by heating under a high vacuum ($1.3 \times 10^{-5}$-$2.6 \times 10^{-4}$ MPa).

The methods for compression compacting include, i) a method in which a mixture of an active ingredient and the porous cellulose aggregate particles, or a mixture of one or more groups of active ingredients and the porous cellulose aggregate particles, and optionally other additives is compression molded by a normal method (direct tablet pressing method), ii) a method in which after mixing an active ingredient and the porous cellulose aggregate particles, and optionally other additives, the mixture was granulated and the granules are compression molded by a normal method (wet/dry type granule compression method), or iii) a method in which an active ingredient and porous cellulose aggregate particles, and optionally other additives are mixed, granulated and further the porous cellulose aggregate particles, and optionally other additives are added and compression molded by a normal method (compression compacting after wet/dry type granulation).

A method for adding one or more of active ingredients, the porous cellulose aggregates, other additives or granules is not particularly restricted if it is commonly practiced method, and either the continuous addition or one time addition may be performed using a small suction transport device, air transport device, bucket conveyer, pressure transport device, vacuum conveyer, quantitative vibration feeder, spray, funnel and the like.

Other than using as tablets after compression compacting, the composition for tablets of the present invention may be used as a granular formulation or powder formulation to improve especially the fluidity, anti-blocking and anti-coagulation characteristics because the composition for tablet of the present invention is superior in retention of solid and liquid components. Any of the methods for producing granular formulation and powder formulation, for example, a dry granulation, wet granulation, heat granulation, spray drying and microcapsulation may be used.

EXAMPLES

The present invention will be described based on Examples. However, the embodiment of the present invention is not limited by this description of Examples. In addition, the methods for measurement and evaluation of each physical property in Examples and Comparative Examples are as follows.

(1) Average Width (μm) of Primary Cellulose Particles

Primary cellulose particles consisting of a natural cellulose substance was optionally dried, placed on a sample platform covered with a carbon tape, vacuum coated with platinum/palladium (thickness of vapor deposited film is 20 nm or less), and observed using JSM-5510V (Commercial Name) made by JASCO Corporation, at an acceleration voltage of 6 kV at a magnification of ×250. The average of three representative primary cellulose particles was calculated.

(2) Average Thickness (μm) of Primary Cellulose Particles

Primary cellulose particles consisting of a natural cellulose substance was optionally dried, placed on a sample platform covered with a carbon tape, vacuum coated with gold, and then a cross section of a primary cellulose particle was excised by Ga ion beam using a converging ion beam manufacturing apparatus (Hitachi, Ltd. FB-2100 (Commercial Name)) and observed at an acceleration voltage of 6 kV at a magnification of ×1500. The average of three representative primary cellulose particles was calculated.

(3) Amount (% by Weight) of Particles that are not Precipitated Under Centrifugal Condition of Centrifugal Force of 4900 m/s$^2$ A cellulose dispersion before drying was accurately weighed (A(g)) in a centrifuge tube (50 ml capacity) and adjusted to about 1% cellulose concentration by adding pure water. The cellulose dispersion before drying was weighed so that the weight after the adjustment was about 30 g. The centrifuge tube containing the cellulose dispersion of about 1% concentration was placed in an inverter-multi purpose high speed refrigerated centrifuge (Type 6930, KUBOTA Corporation, Rapid was used as a mode for acceleration and deceleration) and a RA-400 angle rotor (volume: 50 cm$^3$, material: polypropylene co-polymer, tube angle: 35°, the maximum radius: 10.5 cm, the minimum radius: 5.8 cm, rotation rate: 4100 rpm) and centrifuged at a centrifugal force of 4900 m/s$^2$, in the temperature range of 15-25° C. for 10 minutes. After the centrifugation, the supernatant was transferred to a weighing vial, dried at 110° C. for 5 hours, and the weight of the solid cellulose after drying was measured (B(g)). In addition, the cellulose dispersion was weighed separately in the range of 2-5 g, dried at 110° C. for 5 hours and the weight of the solid after drying was measured (C(%)).

The amount of particles that are not precipitated under centrifugal condition of centrifugal force of 4900 m/s², D (% by weight), was calculated from the following formula.

$$D(\% \text{ by weight}) = \{B(g)/[A(g) \times (C(\%)/100)]\} \times 100$$

(4) Average Particle Size (μm) of Cellulose Dispersion

The average particle size was expressed as a cumulative volume 50% particle by measuring the cellulose dispersed in water using a laser diffraction particle size distribution analyzer (HORIBA, LA-910 (Commercial Name)) after ultrasonic treatment of one minute, at refractive index of 1.20. However, this measurement does not necessarily correlate to the particle size distribution of dried particles obtained by the Ro-tap method described below because of entirely different principle of measurement. The average particle size measured by the laser diffraction is obtained from the volume frequency that is dependent on the major axis of the fibrous particle, while the average particle size obtained by the Ro-tap method is dependent on the minor axis of the fibrous particle because the fractionation is performed by shaking the obtained powder on a sieve. Therefore, the laser diffraction method that depends on the major axis of the fibrous particle sometimes produces larger figures than that of the Ro-tap method that depends on the minor axis of the fibrous particle.

(5) Crystalline Form

An X ray diffraction analysis was conducted by an X ray diffract meter and the crystalline form was determined from the X ray pattern.

(6) Average Particle Size (μm) of Dried Particles.

The average particle size of powder sample was measured using a Ro-tap sieve shake (Taira Kosakusho Ltd., Sieve Shaker A type (Commercial Name)), and JIS standard sieve (Z8801-1987) by sieving 10 g of the sample for 10 minutes and expressed as the accumulated weight 50% particle size.

(7) Specific Surface Area (m²/g)

The measurement was made by the BET method using a TriSTAR (Micrometrics Co., Commercial Name) and nitrogen as an absorbing gas. About one gram of each sample was placed in a cell and measured. Each sample powder used for the measurement had been dried at 110° C. for 3 hours under reduced pressure.

(8) Intraparticular Pore Volume (cm³/g) and Median Pore Diameter (μm)

Pore size distribution was obtained by the mercury porosimetry using an autopore type 9520 (Commercial Name, made by Shimadzu Corporation). Each sample powder used for the measurement had been dried at room temperature for 15 hours under reduced pressure. From the pore size distribution obtained by the measurement at the initial pressure of 20 kPa, "the clear peak area" in the range of pore diameter of 0.1-μm was calculated as the intraparticular pore volume. Further the peak top of "the clear peak" observed in the range of pore diameter of 0.1-15 μm was regarded as the median pore diameter from the obtained pore size distribution and the value was recorded.

(9) Apparent Specific Volume (cm³/g)

The powder sample was poured into a 100 cm³ measuring cylinder using a quantitative feeder or the like in 2-3 minutes and the top layer of the powder sample was made flat using a soft brush and the volume was read. The apparent specific volume was obtained by dividing this volume with the weight of the powder sample. The weight of the powder sample was suitably set so that the volume was 70-100 cm³.

(10) Observation of the Particle Surface and Pores by SEM

Each cellulose sample was placed on a sample platform covered with a carbon tape and vacuum coated with platinum/palladium (thickness of vapor deposited film is 20 nm or less), and observed using JSM-5510V (Commercial Name) made by JASCO Corporation, at an acceleration voltage of 6 kV at a magnification of ×250-×1500. A sample was regarded ○ when it has a secondary aggregated particle structure consisting of continuously aggregated primary particles, in which the boundary between the primary particles were clear and the confirmable median pore diameter was 0.1 μm or above. A sample having a structure other than that was regarded X.

(11) Disintegration of Cellulose Particles in Water

Each cellulose sample of 0.1 g was placed in a glass test tube, mixed with 10 g of pure water and treated with ultrasonic for 1 minute. Observations were made using a microscope (Made by Keyence Corporation, VH-7000 (Commercial name)) with or with out our ultrasonic treatment, and the presence or absence of particle disintegration was monitored. The sample in which disintegration was observed was ○ and not observed was x.

(12) Reactivity to a Drug

Aspirin (Japanese Pharmacopeia crystalline aspirin was treated with a small grinder φ0.5 mm, with 1 pass treatment) and each cellulose sample was mixed at 5/5 (total 0.5 g) in dry conditions and then placed in a glass sample vial and mixed. The vial was stored in an oven (Made by Tabai Espec Corp. Perfect Oven (Commercial Name)) with the cap tightly closed (at 60° C.) for two weeks and then the decomposition rate was measured. Ferric (III) sodium sulfate 12 hydrate 8 g was placed in a 100 ml measuring flask, mixed with pure water to bring the volume up to 100 ml to make a coloring test solution. 0.25 g of stored aspirin (total 0.5 g of the blended powder) was introduced to a 50 ml measuring flask, mixed with ethanol to bring the volume up to 50 ml and the mixture was shaken for 5 minutes. Thus obtained ethanol solution was filtered, the filtrate was transferred to a 100 ml measuring flask and ethanol was added to bring the volume up to 100 ml. One milliliter of this ethanol solution and 1 ml of the coloring test solution described above were introduced to a 50 ml measuring flask, mixed with pure water to bring the volume up to 50 ml and the absorption was measured at the wavelength of 532 nm using a UV absorption meter (made by JASCO Corporation). The decomposition rate was calculated from the following formula.

$$\text{Decomposition rate}(\%) = (1 - (\text{absorption after the storage/absorption before the storage})) \times 100$$

The sample showing a decomposition rate over 15%, which is the decomposition rate of aspirin alone was judged to be reactive.

(13) Repose Angle (°)

Using a Sugihara type repose angle measuring device (slit size: depth 10 mm×width 50 mm×height 140 mm, a protractor was placed at the position of 50 mm width), the dynamic self-fluidity was measured when cellulose powder was dropped to the slit at 3 g/minute using a quantitative feeder. The angle between the bottom of the device and the top layer of the cellulose powder is the repose angle.

(14) Swelling Degree

The swelling degree was obtained from the volume ($V_1$) of about 10 g of powder which was slowly poured into a cylindrical container having 100 cm³ capacity and the volume ($V_2$) of the same powder when about 50 cm³ of pure water was added to the powder and the result is mixed so that the powder was thoroughly wetted and then left standing for 8 hours, by the following formula.

$$\text{Swelling degree}(\%)=(V_2-V_1)/V_1 \times 100$$

(14) Compression Compacting of a Cellulose Sample Alone 0.5 g of each cellulose powder was weighed, placed in a die (KIKUSUI SEISAKUSHO LTD, Material SUS2, 3 were used), compressed with a circular flat punch with a diameter of 1.1 cm (KIKUSUI SEISAKUSHO LTD, Material SUS2, 3 were used) until the pressure of 10 MPa and 20 MPa was attained (AIKOH ENGINEERING CO., LTD. PCM-1A was used. The compression rate was 1 cm/minute), and held at the target pressure for 10 seconds, and then a cylindrical molded body was taken out.

(15) Rotary Tablet Pressing of the Formulated Powder 55 weight parts of acetaminophen (API Corporation, powder type), 0.25 weight parts of light anhydrous silicic acid (Nippon NIPPON AEROSIL CO., LTD., Commercial name: Aerosil 200), 27 weight parts of cellulose particles of powder obtained in Examples and Comparative Examples, two weight parts of crospovidone (BASF, Commercial name: Collidone CL) and 15 weight parts of granular lactose (Lactose New Zealand, Commercial Name: Super-Tab) were placed in a 100 L scale V Type Mixer (Dalton Co., Ltd.) and mixed for 30 minutes, and then 0.5 weight parts of magnesium stearate (TAIHEI CHEMICAL INDUSTRIAL CO., LTD., Plant origin) was added and mixed for further 5 minutes to obtain the formulated powder. Here the total amount of input powders was 25 kg. Thus obtained formulated powder was subjected to tablet pressing using a rotary tablet press (KIKUSUI SEISAKUSHO LTD, Commercial name: LIBRA-II, 36 lines, Rotary table ϕ410 mm) and the formulated powder was supplied by a stirring feeder. Tablet pressing was performed using a punch with 8 mm diameter and 12 R, at a turn table speed of 50 rpm, at a compression force of 7.5 kN to obtain tablets weighing 200 mg each.

(16) Variation of Tablet Mass (%)

Twenty tablets obtained by the rotary tablet pressing were weighed, and the average weight and the standard deviation of the weight were calculated, and the variation of the mass was evaluated from the variation coefficient defined by the formula (standard deviation/average weight)×100. The smaller is the variation coefficient, the smaller is the variation.

(17) Tablet Hardness (N)

Using a Schleuniger hardness tester (Freund Corporation 6D type (Commercial Name)), a cylindrical molded body or a tablet was subjected to a load from the direction of the diameter until destroyed and the load at this time was measured. The hardness was expressed as an average of 10 samples.

(18) Disintegration Time (Second)

The disintegration test was conducted according to the tablet disintegration test method, in the general test method of the 14$^{th}$ edition of the Japanese Pharmacopeia. For a cylindrical molded body or a tablet the disintegration time was obtained in pure water at 37° C. using a disintegration tester (Toyama Sangyo Co., Ltd., NT-40HS type (Commercial Name), in the case of cellulose alone: with disc; in the case of the formulation: without disc). The disintegration time was expressed as the average of 6 samples.

(19) Tablet Friability (% by Weight)

Twenty tablets were weighed (Wa), placed in a friability tester (Japan Machinery Company, PTF-3RA type (Commercial Name)), rotated at 25 rpm for 4 minutes, and then fine powder attached to the tablets was removed. The weight (Wb) of the tablets was measured again and the friability was calculated from the following formula.

$$\text{Friability}=100 \times (Wa-Wb)/Wa$$

(20) Incidence of Tablet Pressing Problems (%)

One hundred tablets obtained by a rotary tablet press were randomly selected and subjected to visual inspection. The number of tablets with splitting (lamination), breaking off (chipping) and peeling off (capping) was counted, and the total number of these tablets was divided by the number of the inspected tablets to obtain the %.

(21) Level-Off Polymerization Degree of Wood Pulp

Ten grams of wood pulp was shredded, hydrolyzed under the condition of 2.5 N hydrochloric acid, at a boiling temperature for 15 minutes and then purified. The dried powder thus obtained was subjected to measurement according to the viscosity method (copper ethylenediamine method) described in the crystalline cellulose confirmation test (13) of the 13$^{th}$ edition of the Japanese Pharmacopeia to obtain the polymerization degree.

(22) Whiteness of Wood Pulp

This value is measured according to ISO (filter R457). The measurement was made by a color difference meter using a blue filter regarding the perfect white as 100%. The degree of whiteness was defined as a reflection rate at a transmission central wavelength of 457 μm.

(22) $S_{10}$, $S_{18}$ of Wood Pulp

A value measured according to Tappi T253m-60. $S_{10}$:

100 cm$^3$ of 10% NaOH was placed in a glass container, cooled to 20° C. for 30 minutes, and 1.6 g of shredded pulp (dry weight is G) was added and immersed well in alkali. The mixture was then stirred at 2300-2800 rpm to dissolve the pulp completely. After cooling the glass container with water, 10 cm$^3$ of 0.4 N potassium dichromate and 30 cm$^3$ of concentrated sulfuric acid were added to 10 cm$^3$ of the filtered solution, and then 100 cm$^3$ of pure water was added and the mixture cooled in water for 30 minutes. After adding 10 cm$^3$ of 10% KI and standing, the mixture was titrated with 0.1 N sodium thiosulfate. The volume of sodium thiosulfate at the endpoint was A (cm$^3$). For 10 cm$^3$ of 10% NaOH before adding pulp, the titration described above was performed. The volume of sodium thiosulfate at the endpoint was B (cm$^3$). $S_{10}$ is calculated from the following formula.

$$S_{10}(\%)=(B-A) \times 0.685/G$$

$$G=\text{weight of pulp} \times (100-\text{water content of pulp})/100$$

The water content of pulp is calculated by drying the pulp at 125° C. for 1.5 hours.

$S_{18}$:

Was measured according to the same method as $S_{10}$ except that 18% NaOH was used.

Example 1

Two kg of shredded commercially available pulp (natural cellulose dissolved pulp derived from wood, average polymerization degree: 1030, average fiber width of the primary cellulose particles: about 39 μm, average thickness: about 8 μm) was immersed in water and, under the condition of containing about 70% water, passed through a cutter mill (URSCHEL LABORATORIES, INC. "Comitrol" (Commercial Name), Model 1700, Microhead/blade gap: 2.029 mm, Immpeler rotation rate: 9000 rpm) and mixed with pure water to prepare a cellulose dispersion of about 2% concentration, which was treated twice with a high pressure homogenizer (MFIC Corp. Commercial Name "Microfluidizer" M-140K type, Process pressure: 200 MPa) and then centrifuged at a centrifugal force of 19600 m/s² to obtain the precipitates after discarding the supernatant. The precipitates were dried at 40° C. for 16 hours, and about 2 kg of the dried precipitates and 30 L of 4 N hydrochloric acid solution were placed in a low speed stirrer (Ikebukuro Horo Kogyo Co., Ltd., 50LGL Reactor (Commercial Name)). Hydrolysis was performed at 40° C. for 48 hours while stirring to obtain an acid insoluble residue. After sufficient washing with pure water, the acid insoluble residue thus obtained was filtered, introduced to a 90 L polyethylene bucket, mixed with pure water to bring the concentration of the total solid fraction to 20% by weight and neutralized with ammonia water while stirring with a 3-1 motor (pH after neutralization was 7.5-8.0). The average fiber width of the primary cellulose particles in this cellulose dispersion containing 20% by weight of the solid fraction was about 19 μm, average thickness was about 3 μm and average particle size was 38 μm. This cellulose dispersion was spray dried (dispersion supply rate: 6 kg/hr, inlet temperature: 180-220° C., outlet temperature: 50-70° C.) to obtain the cellulose particle A that is the cellulose aggregate. The physical properties of the cellulose particle A are shown in Table 1.

Figure 6:
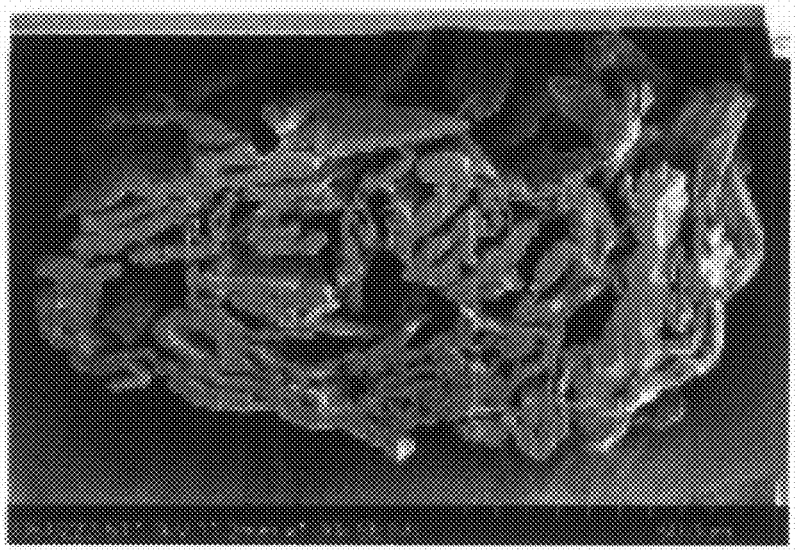
FIG. 6 is a particle cross section photograph of the porous cellulose aggregate of the present invention (Example 1) by an electron microscope.

FIG. 1 shows the results of the measurement of the pore size distribution of the cellulose particle A by the mercury porosimetry, and FIG. 6 shows an electron micrograph of the cross section of the cellulose particle A. As shown in FIG. 1, in the cellulose particle A, a "clear peak" that was derived from the intraparticular pores was confirmed in the range of 0.1-15 μm. This is about the same size as the pore size shown in the electron micrograph by SEM. In addition, the peak shown in the range of 10-50 μm in FIG. 1 is derived from the gap between particles. As shown in FIG. 6, the development of the intraparticular pores having the pore diameter that corresponded to the "clear peak" shown in FIG. 1 was also observed.

Example 2

By subjecting broadleaf trees to a known pulping treatment and bleaching treatment, a pulp was obtained having an average fiber width of the primary cellulose particle of about 19 μm, average thickness of about 3 μm, level off polymerization degree of 140-220, water content of 5-10%, whiteness of 92-97%, viscosity of 5-40 cps, $S_{10}$ 5-15%, $S_{18}$ 1-8%, copper value of 0.5-1.5 and dichloromethane extracts of 0.03 ppm or less. Two kilograms of this pulp and 30 L of 4 N hydrochloric acid solution were placed in a low speed stirrer (Ikebukuro Horo Kogyo Co., Ltd., 50LGL Reactor (Commercial Name)). Hydrolysis was performed at 40° C. for 48 hours while stirring to obtain an acid insoluble residue. After sufficient washing with pure water, the acid insoluble residue thus obtained was filtered, introduced to a 90 L polyethylene bucket, mixed with pure water to bring the concentration of the total solid fraction to 15% by weight and neutralized with ammonia water while stirring with a 3-1 motor (pH after neutralization was 7.5-8.0). The average fiber width of the primary cellulose particles in this cellulose dispersion containing 15% by weight of the solid fraction was about 22 μm, average thickness was about 2.5 μm and average particle size was 38 μm. This cellulose dispersion was spray dried (dispersion supply rate: 6 kg/hr, inlet temperature: 180-220° C., outlet temperature: 50-70° C.) to obtain the cellulose particle B that is the cellulose aggregate. The physical properties of the cellulose particle B are shown in Table 1.

Example 3

By subjecting broadleaf trees to a known pulping treatment and bleaching treatment, a pulp was obtained having an average fiber width of the primary cellulose particle of about 19 μm, average thickness of about 3 μm, level off polymerization degree of 140-220, water content of 5-10%, whiteness of 92-97%, viscosity of 5-40 cps, $S_{10}$ 5-15%, $S_{18}$ 1-8%, copper value of 0.5-1.5 and dichloromethane extracts of 0.03 ppm or less. Two kilograms of this pulp and 30 L of 5 N hydrochloric acid solution were placed in a low speed stirrer (Ikebukuro Horo Kogyo Co., Ltd., 50LGL Reactor (Commercial Name)). Hydrolysis was performed at 40° C. for 20 hours while stirring to obtain an acid insoluble residue. After sufficient washing with pure water, the acid insoluble residue thus obtained was filtered, introduced to a 90 L polyethylene bucket, mixed with pure water to bring the concentration of the total solid fraction to 15% by weight and neutralized with ammonia water while stirring with a 3-1 motor (pH after neutralization was 7.5-8.0). The average fiber width of the primary cellulose particles in this cellulose dispersion containing 18% by weight of the solid fraction was about 22 μm, average thickness was about 2.5 μm and average particle size was 35 μm. This cellulose dispersion was spray dried (dispersion supply rate: 6 kg/hr, inlet temperature: 180-220° C., outlet temperature: 50-70° C.) to obtain the cellulose particle C that is the cellulose aggregate. The physical properties of the cellulose particle C are shown in Table 1.

Example 4

Two kilograms of shredded commercially available pulp (natural cellulose dissolved pulp derived from wood, average polymerization degree: 1030, average fiber width of the primary cellulose particles: about 39 μm, average thickness: about 8 μm) was immersed in water and, under the condition of containing about 70% water, passed through a cutter mill (URSCHEL LABORATORIES, INC. "Comitrol" (Commercial Name), Model 1700, Microcuthead/blade gap: 2.029 mm, Immpeler rotation rate: 9000 rpm) and mixed with pure water to prepare a cellulose dispersion of about 2% concentration, which was treated 4 times with a high pressure homogenizer (MFIC Corp. Commercial Name "Microfluidizer" M-140K type, Process pressure: 200 MPa) and then centrifuged at a centrifugal force of 19600 m/s² to obtain the precipitates after discarding the supernatant. The precipitates were dried at 40° C. for 16 hours, and about 2 kg of the dried precipitates and 30 L of 5 N hydrochloric acid solution were placed in a low speed stirrer (Ikebukuro Horo Kogyo Co., Ltd., 50LGL Reactor (Commercial Name)). Hydrolysis was performed at 40° C. for 20 hours while stirring to obtain an acid insoluble residue. After sufficient washing with pure water, the acid insoluble residue thus obtained was filtered, introduced to a 90 L polyethylene bucket, mixed with pure water to bring the concentration of the total solid fraction to 20% by weight and neutralized with ammonia water while stirring with a 3-1 motor (pH after neutralization was 7.5-8.0). The average fiber width of the primary cellulose particles in this cellulose dispersion containing 20% by weight of the solid fraction was about 15 μm, average thickness was about 1.5 μm and average particle size was 31 μm. This cellulose dispersion was spray dried (dispersion supply rate: 6 kg/hr, inlet temperature: 180-220° C., outlet temperature: 50-70° C.) to obtain the cellulose particle D that is the cellulose aggregate. The physical properties of the cellulose particle D are shown in Table 1.

Example 5

Two kilograms of shredded commercially available pulp (natural cellulose dissolved pulp derived from wood, average polymerization degree: 1030, average fiber width of the primary cellulose particles: about 39 μm, average thickness: about 8 μm) was immersed in water and, under the condition of containing about 70% water, passed through a cutter mill (URSCHEL LABORATORIES, INC. "Comitrol" (Commercial Name), Model 1700, Microcuthead/blade gap: 2.029 mm, Immpeler rotation rate: 9000 rpm) and mixed with pure water to prepare a cellulose dispersion of about 2% concentration, which was treated 6 times with a high pressure homogenizer (MFIC Corp. Commercial Name "Microfluidizer" M-140K type, Process pressure: 200 MPa) and then centrifuged at a centrifugal force of 19600 m/s$^2$ to obtain the precipitates after discarding the supernatant. The precipitates were dried at 40° C. for 16 hours, and about 2 kg of the dried precipitates and 30 L of 4 N hydrochloric acid solution were placed in a low speed stirrer (Ikebukuro Horo Kogyo Co., Ltd., 50LGL Reactor (Commercial Name)). Hydrolysis was performed at 40° C. for 48 hours while stirring to obtain an acid insoluble residue. After sufficient washing with pure water, the acid insoluble residue thus obtained was filtered, introduced to a 90 L polyethylene bucket, mixed with pure water to bring the concentration of the total solid fraction to 15% by weight and neutralized with ammonia water while stirring with a 3-1 motor (pH after neutralization was 7.5-8.0). The average fiber width of the primary cellulose particles in this cellulose dispersion containing 15% by weight of the solid fraction was about 8 μm, average thickness was about 0.6 μm and average particle size was 18 μm. This cellulose dispersion was spray dried (dispersion supply rate: 6 kg/hr, inlet temperature: 180-220° C., outlet temperature: 50-70° C.) to obtain the cellulose particle E that is the cellulose aggregate. The physical properties of the cellulose particle E are shown in Table 1.

Comparative Example 1

Two kilograms of shredded commercially available pulp (natural cellulose dissolved pulp derived from wood, average polymerization degree: 1030, average fiber width of the primary cellulose particles: about 39 μm, average thickness: about 8 μm) and 30 L of 0.14 N hydrochloric acid solution were placed in a low speed stirrer (Ikebukuro Horo Kogyo Co., Ltd., 50LGL Reactor (Commercial Name)). Hydrolysis was performed at 121° C. for 1 hour while stirring to obtain an acid insoluble residue. After sufficient washing with pure water, the acid insoluble residue thus obtained was filtered, introduced to a 90 L polyethylene bucket, mixed with pure water to bring the concentration of the total solid fraction to 17% by weight and neutralized with ammonia water while stirring with a 3-1 motor (pH after neutralization was 7.5-8.0). The average fiber width of the primary cellulose particles in this cellulose dispersion containing 17% by weight of the solid fraction was about 39 μm, average thickness was about 8 μm and average particle size was 36 μm. This cellulose dispersion was spray dried (dispersion supply rate: 6 kg/hr, inlet temperature: 180-220° C., outlet temperature: 50-70° C.) to obtain the cellulose aggregates. These cellulose aggregates were milled using a jet mill (SEISHIN ENTERPRISE CO., LTD., Single Track Jet Mill STJ-200 (Commercial Name)) to obtain cellulose powder F (corresponding to Example 1 of Patent Document 6). The physical properties of the cellulose particle F thus obtained are shown in Table 1.

Results of the SEM observation of cellulose powder B indicated that the particles did not have intraparticular pores, the primary particles existed alone without having the secondary aggregate structure and that no disintegration of the particles in water was observed.

Comparative Example 2

The similar operations were performed as Comparative Example 1 except that the hydrolysis condition was 3N hydrochloric acid solution, at 40° C., for 40 hours and drying at the concentration of the solid 8% to obtain cellulose powder G (corresponding to Example 5 of Patent document 9). The physical properties of the cellulose powder G thus obtained are shown in Table 1. The average fiber width of the primary cellulose particles in the cellulose dispersion before drying was 39 μm, the average thickness was 8 μm and the average particle size was 47 μm.

Comparative Example 3

The similar operations were performed as Comparative Example 1 except that the hydrolysis condition was 3 N hydrochloric acid solution, at 40° C., for 20 hours and drying at the concentration of the solid fraction of 6% to obtain cellulose powder H (corresponding to Example 7 of Patent Document 9). The physical properties of the cellulose powder H thus obtained are shown in Table 1. The average fiber width of the primary cellulose particles in the cellulose dispersion before drying was 39 μm, the average thickness was 8 μm and the average particle size was 49 μm.

Figure 2:
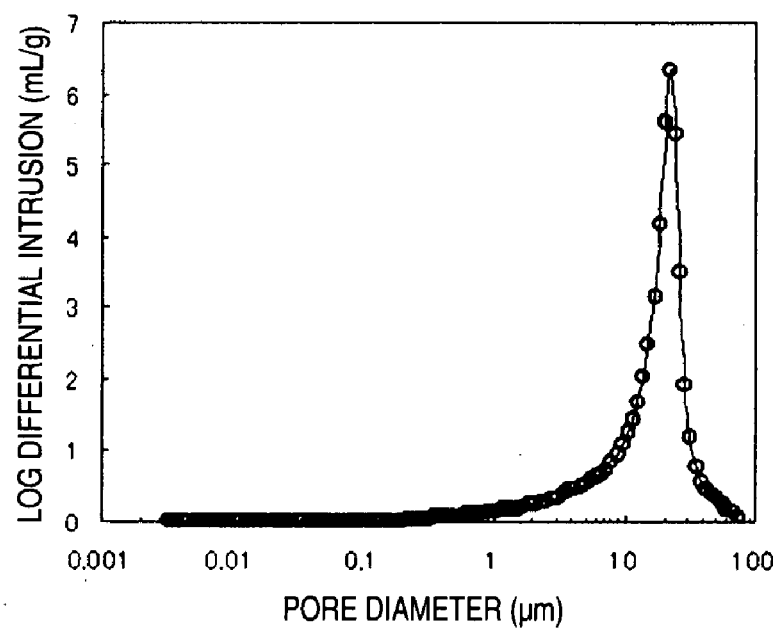
FIG. 2 is the pore size distribution of cellulose powder H (Comparative Example 3) measured by mercury porosimetry.

Further, FIG. 2 shows a pore size distribution pattern of the cellulose powder H measured by the mercury porosimtry. For the cellulose powder H no "clear peak" like the one seen in the porous cellulose aggregates of Example 1 was confirmed. Such pores having no "clear peak" are intrinsic to the original primary cellulose particles. Still further, considering the distribution of the particle size of the powder, the peak seen in the range of 10-50 μm was derived from the gap between particles.

Comparative Example 4

The similar operations were performed as Comparative Example 1 except that the hydrolysis condition was 4 N hydrochloric acid solution, at 40° C., for 48 hours and drying at the concentration of the solid fraction of 16% to obtain cellulose powder I (corresponding to Example 4 of Patent Document 9). The physical properties of the cellulose powder I thus obtained are shown in Table 1. The average fiber width of the primary cellulose particles in the cellulose dispersion before drying was 39 μm, the average thickness was 8 μm and the average particle size was 44 μm.

Comparative Example 5

FMC Co., Ltd., product "Abicel" PH-200 was assigned to be the cellulose powder J. The physical properties of the cellulose powder J are shown in Table 1.

Comparative Example 6

The cellulose aggregates obtained in Comparative Example 1 and acetaminophen, Japanese Pharmacopeia (MERCK HOEI CO., LTD.) milled using a bantam mill (Made by Hosokawa Tekkosho, screen size: 2 mm) were introduced to a high speed stirring granulator (made by GOKYO SEISAKUSHO CO., LTD., NSK250 (Commercial Name)) in a composition of cellulose 50% by weight and acetaminophen 50% by weight, total 500 g of the powder mixture, mixed well by rotating a stirring blade at 500 rpm for 1 minute, further mixed for 2 minutes while adding 245-255 g of 50% by weight ethanol solution to obtain spherical granules. The granules thus obtained were dried at 50° C. for 12 hours, and then after 12 mesh or larger fractions were discarded as coarse large particles, acetaminophen was extracted with acetone for 20 hours using a Soxhlet extraction apparatus. This was again dried at 50° C. for 12 hours to obtain the cellulose powder K (corresponding to Example 2 of Patent Document 2). The physical properties of the cellulose powder K thus obtained are shown in Table 1.

Figure 3:
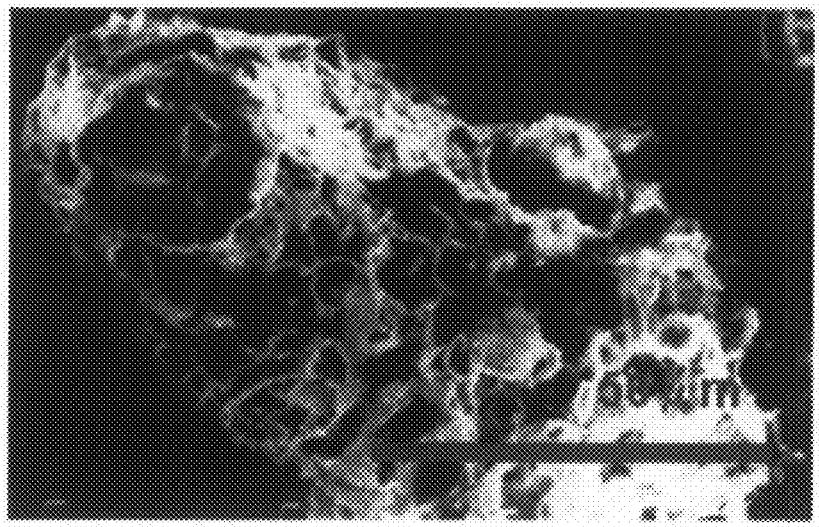
FIG. 3 is an electron micrograph of cellulose particle K (Comparative Example 6) at a magnification of ×250.
Figure 5:
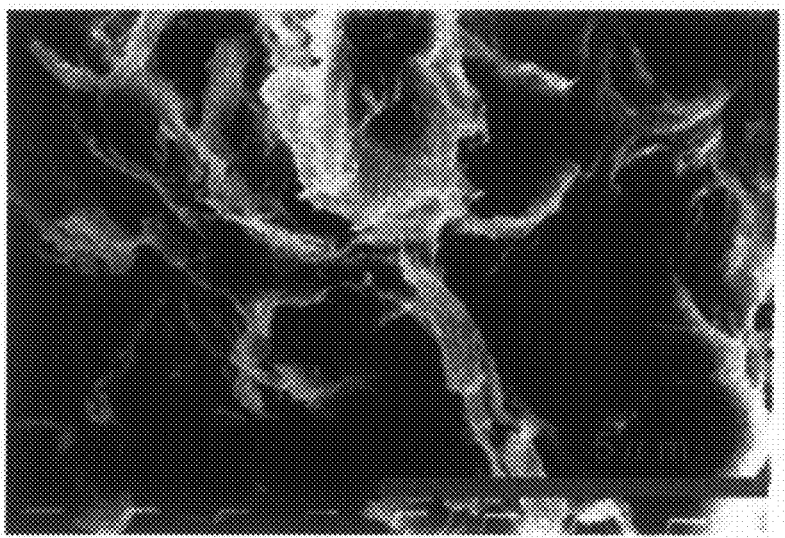
FIG. 5 is an electron micrograph of cellulose particle K (Comparative Example 6) at a magnification of ×1500. From this photo it is seen that the septa are film like and the boundaries of the primary particles are unclear.

FIG. 3 shows an electron micrograph of the cellulose particle K at a magnification of ×250 and FIG. 5 shows an electron micrograph at a magnification of ×1500.

In the cellulose powder K, a "clear peak" was confirmed in the range of 0.1-10 μm of the pore size distribution from the results of the measurement of the pore size distribution by the mercury porosimetry. However, the electron microgram (FIGS. 3 and 5) by SEM confirmed that the particle structure was not the "secondary aggregate structure of the aggregation of the primary particles" but the "dense homogeneously continuous film like septum structure". From FIGS. 3 and 5, it is seen that the primary cellulose particles became microfine particles which bound tightly each other in drying process forming the "dense homogeneously continuous film like septum structure" resulting in that boundaries between the primary particles became unclear. In addition, the particles did not disintegrate in water. Furthermore, the cylindrical molded body (compression pressure 10 MPa) obtained from the cellulose particle K was very much fragile and friable.

Comparative Example 7

A commercially available dissolved pulp was shredded and hydrolyzed in 7% hydrochloric acid solution at 105° C. for 20 minutes, and a wet cake was obtained by neutralizing, washing, filtering and dehydrating thus obtained acid insoluble residue. The wet cake (water content: 50% by weight) was dispersed in isopropyl alcohol and subjected to two cycles of filtration, dehydration and re-dispersion, and further subjected to the dispersion treatment three times using a Manton-Goring homogenizer (made by NIHONSEIKI KAISHA LTD. Type 15M (Commercial Name)) at a treatment pressure of 400 kg/cm² to obtain a cellulose dispersion having the solid fraction concentration of 9.8% by weight, water content of 2.5 weigh %, isopropyl alcohol of 87.7% by weight. The average particle size of the primary cellulose particles of the cellulose dispersion having the solid fraction concentration of 9.8% by weight was 1 μm. This cellulose dispersion was spray dried using a nitrogen circulating type spray dryer. The sample thus obtained was sieved through a JIS standard sieve to cut off the coarse fraction of 250 μm or above to obtain the cellulose powder L (corresponding to Example 2 of Patent Document 3). The physical properties of the cellulose powder L thus obtained are shown in Table 1.

In the cellulose particle L, a "clear peak" was confirmed at 0.1 μm or below from the results of the measurement of the pore size distribution by the mercury porosimetry. Also, the electron microgram by SEM confirmed that the particle structure was not the "secondary aggregate structure of the aggregation of the primary particles" but the "dense homogeneously continuous film like septum structure". The boundaries between the primary particles were unclear in the septa. The particles did not disintegrate in water, and the aspirin decomposition rate was higher than that of the drug alone.

Comparative Example 8

Two kilograms of shredded commercially available pulp (natural cellulose dissolved pulp derived from wood, average polymerization degree: 1030, average fiber width of the primary cellulose particles: about 39 μm, average thickness: about 8 μm) and 30 L of 0.14 N hydrochloric acid solution were placed in a low speed stirrer (Ikebukuro Horo Kogyo Co., Ltd., 50LGL Reactor (Commercial Name)). Hydrolysis was performed at 121° C. for 1 hour while stirring to obtain an acid insoluble residue. After sufficient washing with pure water, the acid insoluble residue thus obtained was filtered, introduced to a 90 L polyethylene bucket, mixed with pure water to bring the concentration of the total solid fraction to 17% by weight and neutralized with ammonia water while stirring with a 3-1 motor (pH after neutralization was 7.5-8.0). The average fiber width of the primary cellulose particles in this cellulose dispersion containing 17% by weight of the solid fraction was about 39 μm, average thickness was about 8 μm and average particle size was 36 μm. This cellulose dispersion was spray dried (dispersion supply rate: 6 kg/hr, inlet temperature: 180-220° C., outlet temperature: 50-70° C.) to obtain the cellulose powder M (corresponding to Example of Patent Document 4).

The physical properties of the cellulose powder M are shown in Table 1. Also an electron micrograph of the cellulose powder M at a magnification ×250 is shown in FIG. 4.

Figure 4:
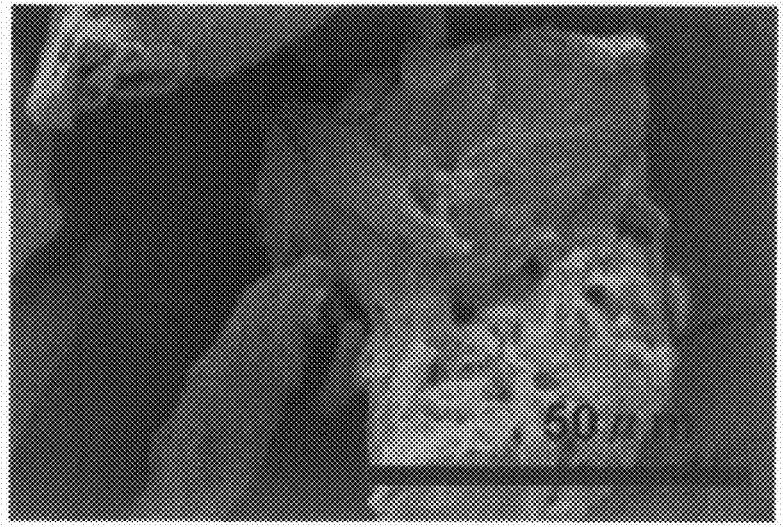
FIG. 4 is an electron micrograph of cellulose powder M (Comparative Example 8) at a magnification of ×250.

From FIG. 4, it is seen that the particle structure of the cellulose powder M is the "secondary aggregate structure of the aggregation of the primary particles". However, since this is the product of drying the dispersion of the cellulose particles having a single average particle size, the intracellular pore volume is small, and no clear peak was observed in the range of 0.1-10 μm in the pore size distribution from the results of the measurement of the pore size distribution by the mercury porosimetry.

Figure 7:
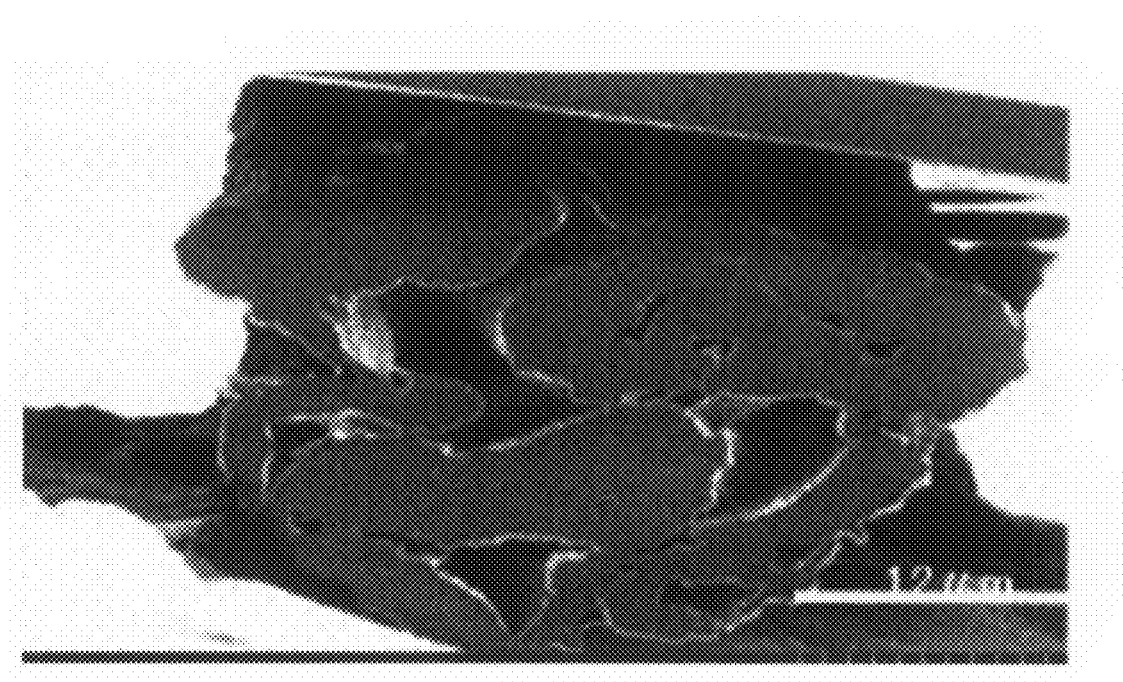
FIG. 7 is a particle cross section photograph of cellulose powder M (Comparative Example 8)) by an electron microscope.

Further, FIG. 7 is a cross section view of the particle of the cellulose powder M by an electron microscope, and a tightly bound structure can be confirmed that was formed by the stiff binding of the cellulose particles. The intraparticular pores were sparse and not well developed and the pore volume measured by the mercury porosimetry is also small.

Comparative Example 9

Two kilograms of a commercially available kraft pulp was shredded and hydrolyzed in 0.7% by weight hydrochloric acid aqueous solution at 125° C. for 150 minutes, and the acid insoluble residue thus obtained was filtered and neutralized. The wet flock thus obtained was sufficiently pulverized in a kneader, mixed with an equal volume of ethanol, pressed and filtered and air dried.

The average fiber width of the primary cellulose particle in cellulose water/ethanol dispersion before drying was 31 μm, the average thickness was 8 μm and average particle size was 28 μm. After air drying, it was milled by a normal hammer mill, and the coarse fraction was removed by sieving through a 40 mesh sieve to obtain the cellulose powder N (corresponding to Example 1 of Patent Document 5). The various physical properties of the cellulose powder N thus obtained are shown in Table 1.

Comparative Example 10

A commercially available dissolved pulp was shredded and hydrolized in 10% by weight hydrochloric acid aqueous solution at 105° C. for 30 minutes. The obtained acid insoluble residue was filtered, washed, and neutralized to obtain a dispersion with a solid fraction concentration of 17% by weight. The primary cellulose particles in the cellulose dispersion had an average fiber width of 39 μm, an average thickness of 8 μm, and an average particle size of 33 μm. The obtained cellulose dispersion was dried with a drum drier (product name KDD-1 from Kusunoki Kikai Seisakusho Co., Ltd. at a steam pressure of 0.35 MPa, a drum temperature of 136° C., a drum speed of 2 rpm, and reservoir dispersion temperature of 100° C.). This was then crushed with a hammer mill and bulk particles were removed with a sieve having a mesh size of 425 μm, providing a Cellulose Powder O (corresponds to Example 1 in Patent Document 7). Various properties of the obtained Cellulose Powder O are shown in Table 1.

Comparative Example 11

An airjet sieve was used on the Cellulose Powder K obtained from Comparative Example 10 and large particles were removed with a 75 μm sieve and fine particles were removed with a 38 μm sieve. This provided the Cellulose Powder P (corresponds to the Example of Patent Document 8). Various physical properties of the obtained Cellulose Powder P are shown in Table 1.

Comparative Example 12

A high-speed stirrer and granulator (model FS-10 (Commercial Name) from Fukae Industries Co., Ltd.) was used with 1.5 kg of Cellulose Powder M obtained from Comparative Example 8 and 1.5 kg of distilled water was added. Kneading was performed for 5 minutes. The Marumerizer Q-230 (Commercial Name, Fuji Paudal Co., Ltd.) was used on 1.0 kg of the wet powder to form spheres by rolling for 10 minutes at 500 rpm. At the same time, 200 g of distilled water was added at a rate of 20 g/min. Then, the powder was left out overnight at 40° C. to dry, after which a 16 mesh (1 mm mesh size) was used to obtain spherical particles Q (corresponds to Example 1 of Patent Document 12). The various physical properties of the obtained spherical particles are shown in Table 1.

The cellulose spherical particles Q are extremely heavy and provide superior fluidity, but there was almost no specific surface area or intraparticular pore volume. A molded body could not be formed under standard compression pressures of 10, 20 MPa.

Comparative Example 13

As in Example 1, a commercially available kraft pulp was shredded and hydrolized in a 10% by weight of hydrochloric acid aqueous solution at 105° C. for 30 minutes. The obtained acid insoluble residue was filtered to obtain a crystal cellulose cake with a solid concentration of 40% (the degree of polymerization of the cake was 153). The cake was ground for 1 hour with an all-purpose mixer/stirrer (model number 5DM-03-R (Commercial Name) from San-Ei Seisakusho, Ltd.). Water was added to the ground cake and a homogenizing mixer (model number TK Homomixer Mark II from Tokushu kika Kogyo) was used to form a 12.5% by weight of solid content cellulose dispersion with adjustments made for particle size, pH, and IC. The primary cellulose particles in the resulting cellulose dispersion had an average particle size of 7 μm. The dispersion was spray dried using a turntable of approximately 8 cm at a rotation speed of 5000 rpm, a flow rate of 6 L/hr, an intake temperature of 170° C., and an outlet temperature of 85° C. Large particles were removed with a sieve having a mesh size of 177 μm to obtain a cellulose powder R. The various physical properties of the obtained cellulose particle R (corresponds to Example 1 of Patent Document 14) are shown in Table 1.

The cellulose particles R are also heavy and have superior fluidity but specific surface area and intraparticular pore volume are low. While a molded body could be formed under standard compression pressures of 10, 20 MPa, the molded body was fragile, with friability taking place upon release. The molded body could be easily destroyed by hand.

Comparative Example 14

A low-speed stirrer (30LGL reactor from Ikebukuro Horo Kogyo Co., Ltd., approximately 30 cm blade diameter) was used with 2 kg of shredded commercially available pulp (with a degree of polymerization of 790) and 30 L of 4 N aqueous hydrochloric acid. Hydrolization was performed for 48 hours at 40° C. while stirring at a stirring speed of 5 rpm, resulting in acid insoluble residue with an average polymerization degree of 270. The obtained acid insoluble residue was filtered to a solid concentration of 40% using a suction funnel. The filtered residue was then washed with pure water and neutralized with ammonia water. This was placed in a 90 L polyethylene bucket. Pure water was added and the result was stirred at a stirring speed of 5 rpm using a 3-1 motor (type 1200G from Heidon, 8 M/M, average blade diameter 5 cm). This provided a cellulose dispersion with a solid concentration of 22%. The primary cellulose particles in the cellulose dispersion had an average fiber width of 39 μm, an average thickness of 8 μm, and an average particle size of 54 μm. This was spray dried (dispersion supply rate: 6 L/hr, inlet temperature: 180-220° C., outlet temperature: 50-70° C.), resulting in a cellulose powder S. The various physical properties of the obtained cellulose particles S (corresponds to Example 2 of Patent Document 10) are shown in Table 1. While the cellulose particles S provided a high degree of hardness in the molded body at 10, 20 MPa, the apparent specific volume was too high, resulting in inferior fluidity (repose angle) and disintegration property.

Comparative Example 15

A low-speed stirrer (30LGL reactor (Commercial Name) from Ikebukuro Horo Kogyo Co., Ltd.) was used with 2 kg of shredded commercial by available pulp (a natural cellulose dissolved pulp derived from wood) and 30 L of 4 N aqueous hydrochloric acid. Hydrolization was performed for 48 hours at 40° C. while stirring, resulting in acid insoluble residue. After thoroughly washing the obtained acid insoluble residue in pure water, the residue was filtered, resulting in a wet flock (the average particle size of the dispersed cellulose particles in the acid insoluble residue was 55 μm.) Of the obtained wet flock, 60% by weight was further washed thoroughly with pure water, neutralized, refiltered, and air dried to produce a dried flock. This dried flock was shredded with a home mixer and then further crushed with a jet mill (single-track jet mill STJ-200 from SEISHIN ENTERPRISE CO., LTD.) to obtain a crushed product (the cellulose particle size was 3 μm. The obtained crushed product and the wet acid insoluble residue described above were placed in a 90 L polyethylene bucket at a composition of 60 parts by weight to 40 parts by weight (dry base). Pure water was added for a total solid fraction concentration of 25% by weight. While stirring with a 3-1 motor, the mixture was neutralized with ammonia water (the pH after neutralization was 7.5-8.0). This was then spray dried (dispersion supply rate: 6 kg/hr, inlet temperature: 180-220° C., outlet temperature: 50-70° C.), resulting in a cellulose powder T (corresponds to Example 2 of Patent Document 1). The various physical properties of the cellulose powder T are shown in Table 1.

Comparative Example 16

A low-speed stirrer (30LGL reactor (Commercial Name) from Ikebukuro Horo Kogyo Co., Ltd.) was used with 2 kg of shredded commercially available pulp (a natural cellulose dissolved pulp derived from wood) and 30 L of 3 N aqueous hydrochloric acid. Hydrolization was performed for 24 hours at 40° C. while stirring, resulting in acid insoluble residue. After thoroughly washing the obtained acid insoluble residue with pure water, the residue was filtered, resulting in a wet flock (the average particle size of the dispersed cellulose particles in the acid insoluble residue was 55 µm. Of the obtained wet flock, 10% by weight was further washed thoroughly with pure water, neutralized, refiltered, and air dried to produce a dried flock. This dried flock was shredded with a home mixer and then further crushed with a jet mill (single-track jet mill STJ-200 from SEISHIN ENTERPRISE CO., LTD.) to obtain a crushed product (the cellulose particle size was 3 µm.) The obtained crushed product and the wet acid insoluble residue described above were placed in a 90 L polyethylene bucket at a composition of 10 parts by weight to 90 parts by weight (dry base). Pure water was added for a total solid fraction concentration of 35% by weight. While stirring with a 3-1 motor, the mixture was neutralized with ammonia water (the pH after neutralization was 7.5-8.0). This was then spray dried (dispersion supply rate: 6 kg/hr, inlet temperature: 180-220° C., outlet temperature: 50-70° C.), resulting in a cellulose powder U (corresponds to Example 5 of Patent Document 1). The various physical properties of the cellulose powder U are shown in Table 1.

Comparative Example 17

A low-speed stirrer (30LGL reactor (Commercial Name) from Ikebukuro Horo Kogyo Co., Ltd.) was used with 2 kg of shredded commercially available pulp (a natural cellulose kraft pulp derived from cotton linter) and 30 L of 0.14 N aqueous hydrochloric acid. Hydrolization was performed for 1 hour at 121° C. while stirring, resulting in acid insoluble residue. After thoroughly washing the obtained acid insoluble residue with pure water, the residue was filtered, resulting in a wet flock (the average particle size of the dispersed cellulose particles in the acid insoluble residue was 36 µm. Of the obtained wet flock, 90% by weight was further washed thoroughly with pure water, and then friability with a planetary mixer (the dispersed cellulose particles in the friated wet flock had an average particle size of 1 µm. The friated wet flock and the unfriated wet flock were placed in a 90 L polyethylene bucket at a composition of 90 parts by weight to 10 parts by weight (dry base). Pure water was added for a total solid fraction concentration of 30% by weight. While stirring with a 3-1 motor, the mixture was neutralized with ammonia water (the pH after neutralization was 7.5-8.0). This was then spray dried (dispersion supply rate: 6 kg/hr, inlet temperature: 180-220° C., outlet temperature: 50-70° C.), resulting in a cellulose powder V (corresponds to Example 7 of Patent Document 1). The various physical properties of the cellulose powder V are shown in Table 1-1 and Table 1-2.

Among conventional cellulose powders, only Comparative Examples 15-17 corresponding to the Examples of Patent Document 1 meet the ranges of the porous cellulose aggregates of the present application: the repose angle range; the hardness range of a cylindrical molded body molded at 10 MPa; and the hardness range of a cylindrical molded body molded at 20 MPa the disintegration time range of a cylindrical molded body molded at 20 Mpa. The advantage of the porous cellulose aggregates of the present application is that the disintegration time is shorter for similar hardnesses (Example 5 and Comparative Example 15, Example 2 and Comparative Example 16, and Example 3 and Comparative Example 17), thus allowing cylindrical molded bodies to be disintegrated in roughly half the time. This is due to the fact that, with the porous cellulose aggregates from Patent Document 1, even the larger central pore diameters were approximately 1.5 µm, while the central pore diameters of the porous cellulose aggregates of the present application are at least approximately 3.0 µm. Thus, the larger central pore diameters provide a faster water permeation rate.

TABLE 1-1

| | | Cellulose powder | Physical properties of primary cellulose particle | | Physical properties of cellulose dispersion | | Physical properties of powder | | | | | Particle structure by SEM (secondary aggregation) |
|---|---|---|---|---|---|---|---|---|---|---|---|---|
| | | | Fiber width (µm) | Fiber thickness (µm) | Average particle size (µm) | Amount of fine particles (%) | Crystal form | Specific surface area (m²/g) | Drug reactivity | Media pore diameter (µm) | Intraparticular pore volume (cm³/g) | |
| Example | 1 | A | 19 | 3 | 38 | 6 | I | 0.8 | No | 4.5 | 0.41 | ○ |
| | 2 | B | 22 | 2.5 | 38 | 5 | I | 1.5 | No | 6.0 | 1.00 | ○ |
| | 3 | C | 22 | 2.5 | 35 | 9 | I | 1.4 | No | 11.0 | 0.55 | ○ |
| | 4 | D | 15 | 1.5 | 31 | 8 | I | 5.0 | No | 8.0 | 0.70 | ○ |
| | 5 | E | 8 | 0.6 | 18 | 2 | I | 12.0 | No | 3.0 | 1.50 | ○ |
| Comparative Example | 1 | F | 39 | 8 | Slurry not formed | Slurry not formed | I | 1.4 | No | Not clear | 0.264 | X |
| | 2 | G | 39 | 8 | 47 | 13 | I | 1.5 | No | Not clear | 0.245 | ○ |
| | 3 | H | 39 | 8 | 49 | 11 | I | 1.7 | No | Not clear | 0.24 | ○ |
| | 4 | I | 39 | 8 | 44 | 14 | I | 1 | No | Not clear | 0.245 | ○ |
| | 5 | J | 39 | 8 | 37 | 15 | I | 1.1 | No | Not clear | 0.203 | ○ |
| | 6 | K | 39 | 8 | Slurry not formed | Slurry not formed | I | 5 | No | 2 | 0.5067 | X |
| | 7 | L | 0.4 | 0.3 | 1 | 70 | I | 24.1 | Yes | Less than 0.1 | 0.89 | X (Median pore |

TABLE 1-1-continued

| | Cellulose powder | Physical properties of primary cellulose particle | | Physical properties of cellulose dispersion | | | Physical properties of powder | | | | Particle structure by SEM (secondary aggregation) |
|---|---|---|---|---|---|---|---|---|---|---|---|
| | | Fiber width (μm) | Fiber thickness (μm) | Average particle size (μm) | Amount of fine particles (%) | Crystal form | Specific surface area (m²/g) | Drug reactivity | Media pore diameter (μm) | Intraparticular pore volume (cm³/g) | |
| | | | | | | | | | | | diameter Less than 0.1 μm) |
| 8 | M | 39 | 8 | 36 | 15 | I | 1 | No | Not clear | 0.258 | ○ |
| 9 | N | 31 | 8 | 28 | 20 | I | 0.6 | No | Not clear | 0.23 | ○ |
| 10 | O | 39 | 8 | 33 | 17 | I | 1.9 | No | Not clear | 0.24 | ○ |
| 11 | P | 39 | 8 | Slurry not formed | Slurry not formed | I | 2.4 | No | Not clear | 0.235 | ○ |
| 12 | Q | 39 | 8 | Slurry not formed | Slurry not formed | I | 0.05 | No | Not clear | 0.048 | X |
| 13 | R | 39 | 8 | 7 | 40 | I | 0.3 | No | Not clear | 0.098 | X |
| 14 | S | 39 | 8 | 54 | 9 | I | 1.2 | No | Not clear | 0.239 | X |
| 15 | T | 39 | 8 | 25 | 30 | I | 12.5 | No | 1.5 | 0.82 | ○ |
| 16 | U | 39 | 8 | 44 | 15 | I | 3.5 | No | 1 | 0.65 | ○ |
| 17 | V | 0.8 | 0.3 | 5 | 60 | I | 2.2 | No | 0.7 | 0.265 | ○ |

TABLE 1-2

| | | Cellulose powder | Physical properties of powder | | | | Physical properties of cylindrical molded body | | |
|---|---|---|---|---|---|---|---|---|---|
| | | | Property to disintegrate in water | Swelling degree (%) | Average particle size (μm) | Apparent specific volume (cm³/g) | Repose angle (° C.) | 10 MPa Hardness (N) | 20 MPa Hardness (N) | 20 MPa Disintegration (Second) |
| Example | 1 | A | Disintegration | 28.0 | 51 | 4.2 | 39 | 89 | 230 | 16 |
| | 2 | B | Disintegration | 10.0 | 230 | 5.1 | 40 | 95 | 260 | 10 |
| | 3 | C | Disintegration | 38.0 | 90 | 3.5 | 34 | 65 | 170 | 5 |
| | 4 | D | Disintegration | 48.0 | 31 | 3.0 | 28 | 70 | 180 | 10 |
| | 5 | E | Disintegration | 6.0 | 150 | 5.5 | 42 | 145 | 410 | 30 |
| Comparative Example | 1 | F | No disintegration | 0.5 | 28 | 4.5 | 55 | 90 | 254 | 289 |
| | 2 | G | Disintegration | 0.0 | 45 | 5.3 | 51 | 110 | 309 | 76 |
| | 3 | H | Disintegration | 1.0 | 38 | 6.3 | 54 | 72 | 203 | 110 |
| | 4 | I | Disintegration | 0.0 | 105 | 4.4 | 44 | 66 | 190 | 35 |
| | 5 | J | Disintegration | 21.0 | 203 | 3.1 | 36 | 52 | 150 | 16 |
| | 6 | K | No disintegration | -4.5 | 174 | 2.1 | 35 | 45 | 127 | 245 |
| | 7 | L | No disintegration | -5.0 | 48 | 4.5 | 48 | 80 | 225 | 210 |
| | 8 | M | Disintegration | 19.0 | 49 | 3.2 | 44 | 57 | 161 | 12 |
| | 9 | N | Disintegration | 40.0 | 35 | 2 | 41 | 40 | 113 | 11 |
| | 10 | O | Disintegration | 0.0 | 47 | 5.4 | 56 | 101 | 188 | 150 |
| | 11 | P | Disintegration | 1.0 | 50 | 6.3 | 59 | 106 | 210 | 220 |
| | 12 | Q | No disintegration | 0.0 | 220 | 1.1 | 26 | 0 | 0 | — |
| | 13 | R | No disintegration | 1.0 | 93 | 1.3 | 32 | 5 | 10 | — |
| | 14 | S | Disintegration | 0.0 | 50 | 7.5 | 50 | 108 | 280 | 268 |
| | 15 | T | Disintegration | 2 | 31 | 4 | 43 | 145 | 409 | 75 |
| | 16 | U | Disintegration | 3 | 248 | 5 | 38 | 90 | 254 | 22 |
| | 17 | V | Disintegration | 4 | 190 | 2 | 26 | 60 | 169 | 9 |

Example 6 and Comparative Examples 18-28

The following were placed in a 100 L scale V-type mixer (Dalton Co., Ltd.) and mixed for 30 minutes: 55 parts of acetaminophen (powder type, API Corporation); 0.25 parts by weight of light anhydrous silicic acid (Aerosil 200 (Commercial Name) of NIPPON AEROSIL CO., LTD.); 27 parts by weight of the cellulose powder A obtained from Example 1 or the cellulose powder B, C, E-L, and O obtained from the Comparative Examples 1, 2, and 4-11, 14; 2 parts by weight of crospovidone (Kollidon CL (Commercial Name) from BASF); and 15 parts of granular lactose (Super-Tab (Commercial Name) from Lactose New Zealand). Then, 0.5 parts by weight of magnesium stearate (plant-based, made by TAIHEI CHEMICAL INDUSTRIAL CO., LTD.) are added and mixed for 5 minutes to obtain a formulated powder. The total intake for the powders was 25 kg. The formulated powder was used in a rotary tablet press (LIBRA-II (Commercial Name) from KIKUSUI SEISAKUSHO LTD, 36 stations, 410 mm turn table diameter). Pressing was performed with an 8 mm diameter, 12R punch with a turn table speed of 50 rpm and a compression force of 7.5 kN, resulting in tablets weighing 200 mg. Tablets were sampled 60 minutes after initiation of tablet pressing, and tablet weight, hardness, friability, and tablet pressing trouble rates were measured. The physical properties of the obtained tablet are shown in Table 2.

Since this formula contains a large amount of drugs with inferior compactibility, obtaining a hardness of 50 N or higher, the hardness considered practical for tablets, is difficult. Obtaining practical tablets is also made difficult because of the tendency for tablet pressing troubles to occur, i.e., sticking at low pressures and capping at high pressures. Out of the Comparative Examples, the Comparative Examples 18, 19, 26, 27, 28 provided a practical tablet hardness of 50 N or higher, but the variation of 1.8-3.5% in tablet weight was much higher than the 0.8% of the Examples, making practical implementation difficult.

Name) from KIKUSUI SEISAKUSHO LTD, 12 stations). Pressing was performed with an 8 mm diameter, 12R punch with a turntable speed of 54 rpm and a compression force of 5 kN, resulting in tablets weighing 180 mg. Tablets were sampled 10 minutes after initiation of tablet pressing, and tablet weight, hardness, friability, tablet pressing trouble rates, and disintegration times (no disk) were measured. The properties of the obtained tablet are shown in Table 3.

The type of drug in this formula was the same as the previous section, but the fluidity of this formula is inferior since the drug is crushed. Thus, the drug content is lower, making reduction of tablet weight variations difficult while obtaining a practical tablet hardness of 50 N or higher is difficult. Obtaining practical tablets is also made difficult because of the tendency for tablet pressing troubles to occur, i.e., sticking at low pressures and capping at high pressures. Out of the Comparative Examples, the Comparative Examples 29, 30, 33, 36, 37, 38, 39 provided a practical tablet hardness of 50 N or higher, but besides the Comparative Example 39 the variation of 1.6-3.5% in tablet weight was much higher than the 0.2-0.5% of the Examples, making

TABLE 2

|  |  | Cellulose powder | Physical properties of tablets that are obtained by high speed tabletting | | | |
|---|---|---|---|---|---|---|
|  |  |  | Variation of tablet weight (%) | Hardness of tablet (N) | Friability of tablet (%) | Tablet pressing trouble rate (%) |
| Example | 6 | A | 0.8 | 60 | 0.4 | 0 |
| Comparative Example | 18 | F | 2.3 | 65 | 0.6 | 0 |
|  | 19 | G | 1.8 | 67 | 0.6 | 0 |
|  | 20 | I | 1.1 | 42 | 6.0 | 30 |
|  | 21 | J | 0.6 | 38 | 15.0 | 88 |
|  | 22 | K | 0.7 | 32 | 12.0 | 48 |
|  | 23 | L | 1.5 | 48 | 5.0 | 15 |
|  | 24 | M | 1.1 | 35 | 19.0 | 72 |
|  | 25 | N | 0.8 | 30 | 22.7 | 90 |
|  | 26 | O | 2.4 | 55 | 0.9 | 0 |
|  | 27 | P | 2.3 | 57 | 0.8 | 0 |
|  | 28 | S | 3.5 | 100 | 0.1 | 0 |

Embodiments 7, 8 and Comparative Examples 29-39

The following were placed in a 100 L scale V-type mixer (Dalton Co., Ltd) and mixed for 30 minutes: 40 parts of acetaminophen (powder type from API Corporation crushed, 6 μm average particle size); 0.5 parts by weight of light anhydrous silicic acid (Aerosil 200 (Commercial Name) of NIPPON AEROSIL CO., LTD.); 30 parts by weight of the cellulose powder C and D obtained from Example 3 and Example 4 and the cellulose powder G, I—P, S, and V obtained from the Comparative Examples 2, 4-11, 14 and 17; 2 parts by weight of sodium croscarmellose (Kiccolate ND-2HS (Commercial Name) produced by NICHIRIN CHEMICAL INDUSTRIES, LTD. and distributed by Asahi Kasei Chemicals Corporation); and 27.5 parts of granular lactose (Super-Tab (Commercial Name) from Lactose New Zealand). Then, 0.5 parts by weight external ratio of magnesium stearate (plant-based, made by TAIHEI CHEMICAL INDUSTRIAL CO., LTD.) were added and mixed for 5 minutes to obtain a formulated powder. The total intake for the powders was 2 kg. The formulated powder was used in a rotary tablet press (Clean Press—12HUK (Commercial practical implementation difficult. With the Comparative Example 39, tablet hardness and tablet weight variations were similar to those of the porous cellulose aggregates of the present invention, but the disintegration time at similar hardnesses was inferior. In direct tablet pressing, stable production can be difficult because of a tendency for there to be differences between drug lots, especially in granularity. Thus, in terms of drug granularity it would be preferable to crush the drugs, but in such cases the fluidity of the crushed drug is inadequate, preventing the drug content from being increased. Of the porous cellulose aggregates of the present invention, those with good fluidity, i.e., with repose angles in a low range of 25-36°, are especially useful in overcoming this problem. Also, for drugs providing inferior tablet compactibility, excipient must be added to provide practical hardness. Thus, the excipient itself must have good fluidity and, in order to increase the drug content as much as possible, the excipient must have a degree of compactibility high enough that a limited amount can provide practical hardness. The porous cellulose aggregates of the present invention provides advantages not available in the conventional cellulose powders in that fluidity and compactibility are both high enough to overcome the above problem.

TABLE 3

Physical properties of tablets that are obtained by high speed tabletting

| | | Cellulose powder | Variation of tablet weight (%) | Hardness of tablet (N) | Friability of tablet (%) | Tablet pressing trouble rate (%) | Disintegration time (sec) |
|---|---|---|---|---|---|---|---|
| Example | 7 | C | 0.5 | 52 | 0.5 | 0 | 11 |
| | 8 | D | 0.2 | 57 | 0.3 | 0 | 15 |
| Comparative | 29 | G | 2.1 | 70 | 0.1 | 0 | 44 |
| Example | 30 | I | 1.6 | 50 | 0.4 | o | 35 |
| | 31 | J | 0.5 | 40 | 2.0 | 30 | 28 |
| | 32 | K | 0.4 | 35 | 5.0 | 40 | 55 |
| | 33 | L | 1.9 | 60 | 0.3 | 0 | 50 |
| | 34 | M | 1.5 | 45 | 0.7 | 0 | 25 |
| | 35 | N | 0.9 | 29 | 15.0 | 80 | 23 |
| | 36 | O | 3.1 | 65 | 0.2 | 0 | 45 |
| | 37 | P | 3.5 | 68 | 0.1 | 0 | 50 |
| | 38 | S | 2.0 | 69 | 0.1 | 0 | 59 |
| | 39 | V | 0.2 | 50 | 0.6 | 0 | 26 |

Embodiment 9, 10, and Comparative Examples 40-51

The following were placed in a 5 L scale V-type mixer (Dalton Co., Ltd) and mixed for 30 minutes: 60 parts of ethenzamide (API Corporation, powder grade crushed with a compact crusher); 0.5 part by weight of light anhydrous silicic acid (Aerosil 200 (Commercial Name) of NIPPON AEROSIL CO., LTD.); 10 parts by weight of the cellulose powder B and E obtained from Examples 2 and 5 and the cellulose powder G, I—P, and S—U obtained from the Comparative Examples 2, 4-11, and 14-16; 1.5 parts by weight of sodium croscarmellose (Kiccolate ND-2HS (Commercial Name) produced by NICHIRIN CHEMICAL INDUSTRIES, LTD. and distributed by Asahi Kasei Chemicals Corporation); and 28 parts of granular lactose (Super-Tab (Commercial Name) from Lactose New Zealand). Then, 0.5 part by weight external ratio of magnesium stearate (plant-based, made by TAIHEI CHEMICAL INDUSTRIAL CO., LTD.) are added and mixed for 5 minutes to obtain a formulated powder. The total intake for the powders was 2 kg. The formulated powder was used in a rotary tablet press (Clean Press—12HUK (Commercial Name) from KIKUSUI SEISAKUSHO LTD, 12 stations). Pressing was performed with an 8 mm diameter, 12R punch with a turn table speed of 54 rpm and a compression force of 8 kN, resulting in tablets weighing 180 mg. Tablets were sampled 10 minutes after initiation of tablet pressing, and tablet weight, hardness, friability, tablet pressing trouble rates, and disintegration times (no disk) were measured. The physical properties of the obtained tablet are shown in Table 4.

Since, in this formula, a drug hard to be soluble in water is crushed, water disintegration properties were inferior and fluidity was inferior, making it difficult to reduce variations in tablet weight. Furthermore, this formula results in tablet pressing troubles in the form of capping at high pressures, thus making it an example of a formula in which practical implementation with a high drug content is difficult. Out of the Comparative Examples, the Comparative Examples 40, 41, 64, 47-51 provided a practical tablet hardness of 50 N or higher, but the variation of 1.6-4.0% in tablet weight was much higher than the 0.5-0.7% of the embodiments, making practical implementation difficult. With the Comparative Examples 50, 51, tablet hardness and tablet weight variations were similar to those of the porous cellulose aggregates of the present invention, but the disintegration time at similar hardnesses was inferior. With lower drug solubility in water, the disintegration time is the rate-limiting factor, and elution time for the drug is increased. For quick absorption in the body, quick disintegration is necessary. As the water solubility of the drug goes lower, it is clear that the difference in disintegration time between the porous cellulose aggregates of the present invention and the porous cellulose aggregates of Patent Document 1 increases. Thus, the present invention is superior to the porous cellulose aggregates of Patent Document 1 especially in terms of the quick disintegration of drugs hard to be soluble in water.

TABLE 4

Physical properties of tablets that are obtained by high speed tabletting

| | | Cellulose powder | Variation of tablet weight (%) | Hardness of tablet (N) | Friability of tablet (%) | Tablet pressing trouble rate (%) | Disintegration time (sec) |
|---|---|---|---|---|---|---|---|
| Example | 9 | B | 0.5 | 70 | 0.4 | 0 | 15 |
| | 10 | E | 0.7 | 100 | 0.1 | 0 | 20 |
| Comparative | 40 | G | 2.3 | 63 | 0.5 | 0 | 40 |
| Example | 41 | I | 1.6 | 50 | 7.0 | 50 | 35 |
| | 42 | J | 0.3 | 44 | 8.0 | 60 | 20 |
| | 43 | K | 0.2 | 38 | 13.0 | 80 | 80 |
| | 44 | L | 1.7 | 64 | 0.6 | 0 | 75 |
| | 45 | M | 1.5 | 49 | 10.0 | 70 | 16 |
| | 46 | N | 0.7 | 30 | 21.0 | 88 | 15 |
| | 47 | O | 3.1 | 90 | 0.2 | 0 | 50 |

TABLE 4-continued

| | Cellulose powder | Physical properties of tablets that are obtained by high speed tabletting | | | | |
|---|---|---|---|---|---|---|
| | | Variation of tablet weight (%) | Hardness of tablet (N) | Friability of tablet (%) | Tablet pressing trouble rate (%) | Disintegration time (sec) |
| 48 | P | 4.0 | 95 | 0.2 | 0 | 76 |
| 49 | S | 2.0 | 97 | 0.2 | 0 | 85 |
| 50 | T | 0.8 | 100 | 0.1 | 0 | 42 |
| 51 | U | 0.7 | 70 | 0.5 | 0 | 25 |

Embodiment 11, 12, and Comparative Examples 52-63

The following were placed in a 5 L scale V-type mixer (Dalton Co., Ltd) and mixed for 30 minutes: 55 parts of ascorbic acid (from Ebisu Co., Ltd., crushed); 30 parts by weight of the cellulose powder B and E obtained from Examples 2 and 5 and the cellulose powder G, I—P, and S—U obtained from the Comparative Examples 2, 4-11, and 14-16; 1.5 parts by weight of sodium croscarmellose (Kiccolate ND-2HS (Commercial Name) produced by NICHIRIN CHEMICAL INDUSTRIES, LTD. and distributed by Asahi Kasei Chemicals Corporation); and 13 parts of granular lactose (Super-Tab (Commercial Name) from Lactose New Zealand). Then, 2.0 parts by weight external ratio of magnesium stearate (plant-based, made by TAIHEI CHEMICAL INDUSTRIAL CO., LTD.) are added and mixed for 5 minutes to obtain a formulated powder. The total intake for the powders was 2 kg. The formulated powder was used in a rotary tablet press (Clean Press—12HUK (Commercial Name) from KIKUSUI SEISAKUSHO LTD, 12 stations). Pressing was performed with an 8 mm diameter, 12R punch with a turn table speed of 54 rpm and a compression force of 10 kN, resulting in tablets weighing 180 mg. Tablets were sampled 10 minutes after initiation of tablet pressing, and tablet weight, hardness, friability, tablet pressing trouble rates, and disintegration times (no disk) were measured. The physical properties of the obtained tablet are shown in Table 5.

The drug used in this formula provides relatively good fluidity even when crushed. However, as the drug content is increased the fluidity of the formula gradually decreases, thus making it more difficult to reduce variations in tablet weight when higher drug content is used. Also, the drug used in this formula leads to tablet pressing troubles, i.e., sticking at low pressures and capping at high pressures, making it an example of a formula with which tablets are difficult to practically implement at higher drug contents. Out of the Comparative Examples, the Comparative Examples 52, 56, 59-63 provided a practical tablet hardness of 50 N or higher, but other than the Comparative Examples 62, 63, the variation of 1.8-2.6% in tablet weight was much higher than the 0.7-0.8% of the embodiments, making practical implementation difficult. With the Comparative Examples 62, 63, tablet hardness and tablet weight variations were similar to those of the porous cellulose aggregates of the present invention, but the disintegration time at similar hardnesses was inferior. The drug used in this formula has relatively high water solubility but water-repelling magnesium stearate must be added to avoid tablet pressing troubles. In these cases, the wettability of the tablet to water is reduced, tending to delay disintegration time even if the water solubility of the drug is high. Especially in cases where the wettability of the tablet or the like is obstructed by an a water-repellant additive or the like in the formula, the difference in disintegration times between the porous cellulose aggregates of the present invention and the porous cellulose aggregates of Patent Document 1 clearly increases. Thus the present invention is superior to the porous cellulose aggregates of Patent Document 1.

TABLE 5

| | | Cellulose powder | Physical properties of tablets that are obtained by high speed tabletting | | | | |
|---|---|---|---|---|---|---|---|
| | | | Variation of tablet weight (%) | Hardness of tablet (N) | Friability of tablet (%) | Tablet pressing trouble rate (%) | Disintegration time (sec) |
| Example | 11 | B | 0.7 | 75 | 0.3 | 0 | 25 |
| | 12 | E | 0.8 | 105 | 0.1 | 0 | 60 |
| Comparative Example | 52 | G | 1.8 | 51 | 0.9 | 0 | 79 |
| | 53 | I | 1.2 | 45 | 2.5 | 5 | 65 |
| | 54 | J | 0.6 | 44 | 5.0 | 30 | 30 |
| | 55 | K | 0.5 | 40 | 10.0 | 40 | 110 |
| | 56 | L | 2.1 | 70 | 0.4 | 0 | 100 |
| | 57 | M | 1.1 | 48 | 1.9 | 21 | 29 |
| | 58 | N | 0.7 | 35 | 25.0 | 50 | 25 |
| | 59 | O | 2.3 | 85 | 0.2 | 0 | 90 |
| | 60 | P | 2.6 | 88 | 0.3 | 0 | 105 |
| | 61 | S | 1.9 | 90 | 0.1 | 0 | 119 |
| | 62 | T | 0.8 | 105 | 0.1 | 0 | 90 |
| | 63 | U | 0.7 | 73 | 0.5 | 0 | 35 |

Embodiment 13

Five grams of cellulose powder A was added to 20 g of an active component solution in which an ibuprofen polyethyleneglycol solution (1:5 ratio) is diluted by 10 with ethanol (Wako Pure Chemical Industries, Ltd., reagent), and this was mixed in a beaker with a magnetic stirrer for 5 minutes. The resulting mixed solution was vacuum dried with an evaporator to produce a powder. A die (from KIKUSUI SEISAKUSHO LTD, made with SUS 2, 3) was filled with 0.2 g of the obtained powder, and a circular flat punch (from KIKUSUI SEISAKUSHO LTD, made with SUS 2, 3) with a diameter of 0.8 cm was used to apply compression until the pressure reached 100 MPa (PCM-1A (Commercial Name) from AIKOH ENGINEERING CO., LTD. was used with a compression rate of 1 cm/min). The cylindrical molded body was released after the target pressure was maintained for 10 seconds. The surface of the compression-molded molded body was observed and no effusion of fluid components was observed. Also, 100 mL of pure water was placed in a beaker and stirred with a stirrer. A sieve with a mesh size of 1000 μm was placed over the stirrer, and the molded body was placed on the sieve and left for one minute and observed. The results are shown in Table 6.

Comparative Example 64

A molded body with a fluid component was produced using operations similar to those from Example 13 except that the cellulose particles A were replaced with the cellulose powder K (corresponds to Example 2 in Patent Document 2). Fluid component effusion and disintegration tests were conducted. The results are shown in Table 6.

Comparative Example 65

A molded body with a fluid component was produced using operations similar to those from Example 13 except that the cellulose particles A were replaced with the cellulose powder L (corresponds to Example 2 in Patent Document 3). Fluid component effusion and disintegration tests were conducted. The results are shown in Table 6.

Comparative Example 66

A molded body with a fluid component was produced using operations similar to those from Example 13 except that the cellulose particles A were replaced with the cellulose powder M (corresponds to the embodiment in Patent Document 4). Fluid component effusion and disintegration tests were conducted. The results are shown in Table 6.

Comparative Example 67

A molded body with a fluid component was produced using operations similar to those from Example 13 except that the cellulose particles A were replaced with the cellulose powder N (corresponds to Example 1 in Patent Document 5). Fluid component effusion and disintegration tests were conducted. The results are shown in Table 6.

Comparative Example 68

A molded body with a fluid component was produced using operations similar to those from Example 13 except that the cellulose particles A were replaced with the cellulose powder G (corresponds to Example 5 in Patent Document 9). Fluid component effusion and disintegration tests were conducted. The results are shown in Table 6.

Comparative Example 69

A molded body with a fluid component was produced using operations similar to those from Example 13 except that the cellulose particles A were replaced with the cellulose powder S (corresponds to Example 2 in Patent Document 10). Fluid component effusion and disintegration tests were conducted. The results are shown in Table 6.

TABLE 6

| | | Physical properties of compression molded body | |
|---|---|---|---|
| | Cellulose particle | Effusion of liquid components | Disintegration property |
| Example 13 | A | No effusion | Disintegration |
| Comparative Example 64 | K | No effusion | No disintegration |
| Comparative Example 65 | L | No effusion | No disintegration |
| Comparative Example 66 | M | Effusion | Disintegration |
| Comparative Example 67 | N | Effusion | Disintegration |
| Comparative Example 68 | G | Effusion | Disintegration |
| Comparative Example 69 | S | No effusion | No disintegration |

Embodiment 14

Cellulose particles A were used. A commercially available ibuprofen (an active component indicated as being almost completely insoluble in water according to Japanese Pharmacopeia 14) was dissolved in polyethylene glycol (Macrogol 400 from Sanyo Kasei Co., Ltd.) at a proportion of 1:5, and then diluted by 10 with ethanol. This was added to the cellulose particles A to result in 10% by weight. The mixture was stirred in a die. A die (from KIKUSUI SEISAKUSHO LTD, made with SUS 2, 3) was filled with 0.2 g of the obtained powder, and a circular flat punch (from KIKUSUI SEISAKUSHO LTD, made with SUS 2, 3) with a diameter of 0.8 cm was used to apply compression until the pressure reached 100 MPa (PCM-1A (Commercial Name) from AIKOH ENGINEERING CO., LTD. was used with a compression rate of 1 cm/min). The cylindrical molded body was released after the target pressure was maintained for 10 seconds. Fluid component effusion on the surface of the molded body was observed, drug elution from the cylindrical molded body (elution tests were conducted with a JASCO Corporation ultraviolet absorption spectrometer at paddle speed 100 rpm and 900 mL of Pharmacopeia I liquid, in which fluid absorbance was measured and the elution rate was calculated 3 minutes after) and disintegration time of the cylindrical molded bodies was measured. The results are shown in Table 7. There was no effusion of polyethylene glycol from the cylindrical molded body, and the disintegration property was good with a high drug elution rate after 3 minutes, and it was confirmed that the dissolution was quick.

Comparative Example 70

A molded body was produced using operations similar to those from Example 14 except that the cellulose particles A were replaced with the cellulose powder K (corresponds to Example 2 in Patent Document 2). Fluid component effusion on the surface of the molded body was observed, the rate of drug elution from the cylindrical molded body was measured, and disintegratability was observed. The results are shown in Table 7. Effusion of the fluid component was not observed on the surface of the cylindrical molded body, but in the elution test the tablets did not disintegrate in 3 minutes and floated on the liquid surface instead and the disintegration property was poor.

Comparative Example 71

A molded body was produced using operations similar to those from Example 14 except that the cellulose particles A were replaced with the cellulose powder L (corresponds to Example 2 in Patent Document 3). Fluid component effusion on the surface of the molded body was observed, the rate of drug elution from the cylindrical molded body was measured, and disintegratability was observed. The results are shown in Table 7. Effusion of the fluid component was not observed on the surface of the cylindrical molded body, but in the elution test the tablets did not disintegrate in 3 minutes and floated on the liquid surface instead and disintegratability was poor.

Comparative Example 72

A molded body was produced using operations similar to those from Example 14 except that the cellulose particles A were replaced with the cellulose powder IM (corresponds to the embodiment in Patent Document 4). Fluid component effusion on the surface of the molded body was observed, the rate of drug elution from the cylindrical molded body was measured, and disintegratability was observed. The results are shown in Table 7. Effusion of the fluid component was observed on the surface of the cylindrical molded body, and elution tests could not be performed since tablets could not be formed.

Comparative Example 73

A molded body was produced using operations similar to those from Example 14 except that the cellulose particles A were replaced with the cellulose powder N (corresponds to Example 1 in Patent Document 5). Fluid component effusion on the surface of the molded body was observed, the rate of drug elution from the cylindrical molded body was measured, and disintegratability was observed. The results are shown in Table 7. Effusion of the fluid component was observed on the surface of the cylindrical molded body. Tablets were not formed and elution tests could not be conducted.

Comparative Example 74

A molded body was produced using operations similar to those from Example 14 except that the cellulose particles A were replaced with the cellulose powder G (corresponds to Example 5 in Patent Document 9). Fluid component effusion on the surface of the molded body was observed, the rate of drug elution from the cylindrical molded body was measured, and disintegratability was observed. The results are shown in Table 7. Effusion of the fluid component was observed on the surface of the cylindrical molded body. Tablets were not formed and elution tests could not be conducted.

Comparative Example 75

A molded body was produced using operations similar to those from Example 14 except that the cellulose particles A were replaced with the cellulose powder S (corresponds to Example 2 in Patent Document 10). Fluid component effusion on the surface of the molded body was observed, the rate of drug elution from the cylindrical molded body was measured, and disintegratability was observed. The results are shown in Table 7. Effusion of the fluid component was not observed on the surface of the cylindrical molded body, but disintegratability was not good, with no disintegration in 3 minutes in the effusion test.

TABLE 7

| | | Physical properties of compression molded body | | |
|---|---|---|---|---|
| | Cellulose | Condition of molded body | Condition of disintegration | Elution rate after 3 minutes (%) |
| Example 14 | A | No effusion, solidification | Disintegration | 97 |
| Comparative Example 70 | K | No effusion, solidification | No disintegration | 35 |
| Comparative Example 71 | L | No effusion, solidification | No disintegration | 38 |
| Comparative Example 72 | M | Effusion, no solidification | not done | Cannot be done |
| Comparative Example 73 | N | Effusion, no solidification | not done | Cannot be done |
| Comparative Example 74 | G | Effusion, no solidification | not done | Cannot be done |
| Comparative Example 75 | S | No effusion, solidification | No disintegration | 10 |

Embodiment 15

A solution was formed by dissolving ethenzamide (API Corporation, powder grade crushed with a compact crusher) in ethanol (Wako Pure Chemical Industries, Ltd., reagent chemical) at a proportion of 5:95. One gram of cellulose particles A was added to 10 mL of the solution, and this was stirred for 3 minutes with a magnetic stirrer. The resulting dispersion was placed in an evaporator to perform complete solvent removal, resulting in a powder sample. This powder was used as in Example 14 except that compression was performed at 50 MPa when forming the cylindrical molded body. An elusion test was performed. The results are shown in Table 8.

Comparative Example 76

An elution test was performed on just ethenzamide crushed according to Example 15. The results are shown in Table 8.

TABLE 8

| | Physical properties of compression molded body | |
|---|---|---|
| | Cellulose | Elution rate after 1 hour (%) |
| Example 15 | A | 100 |
| Comparative Example 76 | Ethenzamide material powder | 9 |

Embodiment 16

Cellulose particles A were used. A commercial ibuprofen (an active component indicated as being almost completely insoluble in water according to Japanese Pharmacopeia 14) was dissolved in ethanol (Wako Pure Chemical Industries, Ltd., reagent chemical) at a proportion of 1:5, and this was added to the cellulose particles A to result in 10% by weight. The mixture was stirred in a die. The ethanol was completely removed from the resulting wet powder mixture using an evaporator, providing a dry powder. A die (from KIKUSUI SEISAKUSHO LTD, made with SUS 2, 3) was filled with 0.2 g of the obtained powder, and a circular flat punch (from KIKUSUI SEISAKUSHO LTD, made with SUS 2, 3) with a diameter of 0.8 cm was used to apply compression until the pressure reached 100 MPa (PCM-1A (Commercial Name) from AIKOH ENGINEERING CO., LTD. was used with a compression rate of 1 cm/min). The cylindrical molded body was released after the target pressure was maintained for 10 seconds. One hundred of the cylindrical molded bodies were placed in a bottle and sealed for 2 weeks at 40° C. Fogging on the bottle was observed. Also, for the obtained cylindrical molded bodies, tests were conducted for elution of active components (elution tests were conducted with a JASCO Corporation ultraviolet absorption spectrometer at paddle speed 100 rpm and 900 mL of Pharmacopeia I liquid, in which fluid absorbance was measured 1 minute after and the elution rate was calculated 3 minutes after starting the test) and disintegration property of the molded bodies was observed. The results are shown in Table 9.

Comparative Example 77

Operations similar to those of Example 16 were performed except that cellulose particles A were replaced with cellulose powder K (corresponds to Example 2 of Patent Document 2). Clouding of bottles after sealing in the cylindrical molded bodies was observed, elution tests were performed, and disintegratability was observed. The results are shown in Table 9. No clouding of bottles was observed, but the tablets did not disintegrate in 1 minute and floated on the liquid surface instead.

Comparative Example 78

Operations similar to those of Example 16 were performed except that cellulose particles A were replaced with cellulose powder L (corresponds to Example 2 of Patent Document 3). Clouding of bottles after sealing in the cylindrical molded bodies was observed, elution tests were performed, and disintegratability was observed. The results are shown in Table 9. No clouding of bottles was observed, but the tablets did not disintegrate in 1 minute and floated on the liquid surface instead.

Comparative Example 79

Operations similar to those of Example 16 were performed except that cellulose particles A were replaced with cellulose powder M (corresponds to the embodiment of Patent Document 4). Clouding of bottles after sealing in the cylindrical molded bodies was observed, elution tests were performed, and disintegratability was observed. The results are shown in Table 9. Clouding of the bottle was observed due to the recrystallization on the bottle walls of sublimated ibuprofen.

TABLE 9

| | | Physical properties of compression molded body | | |
|---|---|---|---|---|
| | Cellulose particle | Cloudiness of vial | Disintegration property | Elution rate (%) |
| Example 16 | A | None | Disintegration | 95 |
| Comparative Example 77 | K | None | No disintegration | 32 |
| Comparative Example 78 | L | None | No disintegration | 30 |
| Comparative Example 79 | M | Present | Disintegration | 18 |

Embodiment 17

Twenty grams of acetaminophen (powder type, API Corporation, crushed with a compact crusher so that the resulting acetaminophen has an average particle size of 16 μm and 20 g of talc (Wako Pure Chemical Industries, Ltd.) were placed in a polyethylene bag and mixed thoroughly by hand for 3 minutes. In addition to this 40 g of mixed powder, the following were placed in a 5 L capacity V-type mixer (Dalton Co., Ltd) and mixed for 30 minutes: 952 g of 100 mesh lactose (Pharmatose 100M (Commercial Name) from DMV Corporation); and 408 g of Japanese Pharmacopeia corn starch (NIPPON STARCH CHEMICAL CO., LTD.). This was used as a component model A having low fluidity. After 30 minutes of mixing, the repose angle was measured to be 47°.

Next, 20 g of acetaminophen (powder type, API Corporation, crushed with a compact crusher so that the resulting acetaminophen has an average particle size of 16 μm and 20 g of talc (Wako Pure Chemical Industries, Ltd.) were placed in a polyethylene bag and mixed thoroughly by hand for 3 minutes. In addition to this 40 g of mixed powder, the following were placed in a 5 L capacity V-type mixer (Dalton Co., Ltd) and mixed for 30 minutes: 952 g of 100 mesh lactose (Pharmatose 100M (Commercial Name) from DMV Corporation); 408 g of Japanese Pharmacopeia corn starch (NIPPON STARCH CHEMICAL CO., LTD.); and 600 g of porous cellulose particles A. After 30 minutes of mixing, 10 g of magnesium stearate (0.5% external ratio) was added and the result was mixed for 5 more minutes. The repose angle was measured for the final formula powder (final composition: acetaminophen/talc/100 mesh lactose/corn starch/porous cellulose aggregate/magnesium stearate=1.0/1.0/47.6/20.4/30.0/0.5). The results are shown in Table 10.

The final formulated powder was used in a rotary tablet press (LIBRA-II (Commercial Name) from KIKUSUI SEISAKUSHO LTD, 36 stations, 410 mm turn table diameter). Pressing was performed with an 8 mm diameter, 12R punch with a turn table speed of 50 rpm (108,000 tablets an hour) and a compression force of 10 kN, resulting in tablets weighing 180 mg. Tablets were sampled 10 minutes after initiation of tablet pressing, and tablet weight variation, hardness, and friability were measured. The physical properties of the obtained tablet are shown in Table 10.

Comparative Examples 80-83

Operations similar to those from Example 17 were performed except that the porous cellulose particles A were replaced with the cellulose powder K, M, N, or G. The results are shown in Table 10.

Embodiment 18

The following were placed in a 5 L scale V-type mixer (Dalton Co., Ltd) and mixed for 30 minutes: 200 g of acetaminophen (powder type, API Corporation, crushed with a compact crusher so that the resulting acetaminophen has an average particle size of 16 μm; 760 g granular lactose (SUPER-TAB (Commercial Name) made by Lactose New Zealand, sold by Asahi Kasei Chemicals Corporation); and 40 g of sodium croscarmellose (Kiccolate ND-2HS (Commercial Name) produced by NICHIRIN CHEMICAL INDUSTRIES, LTD. and distributed by Asahi Kasei Chemicals Corporation). This was used as a component model B having low fluidity. After 30 minutes of mixing, the repose angle was measured to be 50°.

Next, the following were placed in a 5 L capacity V-type mixer (Dalton Co., Ltd) and mixed for 30 minutes: 200 g of acetaminophen (powder type, API Corporation, crushed with a compact crusher so that the resulting acetaminophen has an average particle size of 16 μm; 760 g granular lactose (SUPER-TAB (Commercial Name) made by Lactose New Zealand, sold by Asahi Kasei Chemicals Corporation); 40 g of sodium croscarmellose (Kiccolate ND-2HS (Commercial Name) produced by NICHIRIN CHEMICAL INDUSTRIES, LTD. and distributed by Asahi Kasei Chemicals Corporation); and 1000 g of porous cellulose particles A. After 30 minutes of mixing, 10 g of magnesium stearate (0.5% external ratio) was added to the formula powder and the result was mixed for 5 more minutes. The repose angle was measured for the final formula powder (final composition: acetaminophen/granular lactose/sodium croscarmellose/porous cellulose aggregate/magnesium stearate=10/38.0/2.0/50.0/0.5). The results are shown in Table 10.

Next, the final formulated powder was used in a rotary tablet press (Libra-II (Commercial Name) from KIKUSUI SEISAKUSHO LTD, 36 stations, 410 mm turn table diameter). Pressing was performed with an 8 mm diameter, 12R punch with a turn table speed of 50 rpm (108,000 tablets an hour) and a compression force of 10 kN, resulting in tablets weighing 180 mg. Tablets were sampled 10 minutes after initiation of tablet pressing, and tablet weight variation, hardness, and friability were measured. The physical properties of the obtained tablet are shown in Table 10.

Comparative Examples 84-87

Operations similar to those from Example 18 were performed except that the porous cellulose particles A were replaced with the cellulose powder K, M, N, or G. The results are shown in Table 10.

Embodiment 19

Acetaminophen (powder type, API Corporation, crushed with a compact crusher so that the resulting acetaminophen has an average particle size of 16 μm) was used as a component model C having low fluidity. The repose angle was measured to be 55°.

Next, 200 g of acetaminophen (powder type, API Corporation, crushed with a compact crusher so that the resulting acetaminophen has an average particle size of 16 μm) and 18000 g of porous cellulose particles A were mixed for 30 minutes in a 5 L capacity V-type mixer (Dalton Co., Ltd). After 30 minutes of mixing, 10 g each (0.5% external ratio each) of light anhydrous silicic acid and magnesium stearate were added to the formula powder and mixed for 5 more minutes. The repose angle was measured for the final formula powder (final composition: acetaminophen/porous cellulose aggregate/light anhydrous silicic acid/magnesium stearate=10/90/0.5/0.5). The results are shown in Table 10.

Next, the final formulated powder was used in a rotary tablet press (LIBRA-II (Commercial Name) from KIKUSUI SEISAKUSHO LTD, 36 stations, 410 mm turn table diameter). Pressing was performed with an 8 mm diameter, 12R punch with a turn table speed of 50 rpm (108,000 tablets an hour) and a compression force of 2 kN, resulting in tablets weighing 180 mg. Tablets were sampled 10 minutes after initiation of tablet pressing, and tablet weight variation, hardness, and friability were measured. The physical properties of the obtained tablet are shown in Table 10.

Comparative Examples 88-91

Operations similar to those from Example 19 were performed except that the porous cellulose particles A were replaced with the cellulose powder K, M, N, or G. The results are shown in Table 10.

Out of the Comparative Examples, the Comparative Examples with a practical tablet hardness of 50 N or higher had significant variations in tablet weight, making practical implementation difficult. The ones with less variation in drug content in the final powder and tablet weight did not provide practical hardness, making practical implementation difficult.

TABLE 10

| | Cellulose | Component model | Repose angle (°) Before the addition of cellulose | Repose angle (°) After addition of cellulose | Drug content CV value of the final powder | Tablet weight CV (%) | Tablet hardness (N) |
|---|---|---|---|---|---|---|---|
| Example 17 | A | A | 47 | 42 | 1.4 | 0.5 | 60 |
| Comparative Example 80 | K | | | 39 | 3.0 | 0.3 | 32 |
| Comparative Example 81 | M | | | 46 | 2.0 | 1.1 | 30 |
| Comparative Example 82 | N | | | 44 | 2.5 | 0.8 | 15 |
| Comparative Example 83 | G | | | 49 | 1.5 | 2.5 | 55 |
| Example 18 | A | B | 50 | 43 | 0.8 | 0.8 | 55 |
| Comparative Example 84 | K | | | 40 | 2.0 | 0.6 | 25 |
| Comparative Example 85 | M | | | 47 | 1.6 | 1.8 | 20 |
| Comparative Example 86 | N | | | 45 | 1.9 | 1.1 | 9 |
| Comparative Example 87 | G | | | 50 | 1.1 | 3.0 | 51 |

TABLE 10-continued

| | Cellulose | Component model | Repose angle (°) Before the addition of cellulose | Repose angle (°) After addition of cellulose | Drug content CV value of the final powder | Tablet weight CV (%) | Tablet hardness (N) |
|---|---|---|---|---|---|---|---|
| Example 19 | A | C | 55 | 44 | 0.6 | 1.5 | 74 |
| Comparative Example 88 | K | | | 42 | 1.8 | 1.4 | 40 |
| Comparative Example 89 | M | | | 48 | 1.1 | 2.5 | 32 |
| Comparative Example 90 | N | | | 46 | 1.2 | 1.8 | 17 |
| Comparative Example 91 | G | | | 52 | 0.8 | 3.5 | 56 |

INDUSTRIAL APPLICABILITY

A high-fluidity porous cellulose aggregate, and a compacting composition containing the cellulose particles thereof and at least one type of active ingredient according to the present invention provides superior compactibility and disintegration property. In the present invention: the porous structure has a crystal structure I and an aggregation of primary particles; the specific surface area is in a predetermined range; the intraparticular pore volume is large; disintegration takes place quickly in water; the repose angle is low. The present invention can be used effectively primarily in the medical field.

The invention claimed is:

1. A porous cellulose aggregate having a secondary aggregate structure formed by aggregation of primary cellulose particles, a pore volume within a particle of 0.265 cm$^3$/g-2.625 cm$^3$/g, containing type I crystals, and having an average particle size of more than 30 μm and 250 μm or less, a specific surface area of 0.1 m$^2$/g or more and less than 20 m$^2$/g, a repose angle of 25° or more and less than 44°, a swelling degree of 5% or more, and properties to disintegrate in water, wherein porous cellulose aggregate is obtained by a production method comprising:

a step of obtaining a dispersion (hereinafter may also be designated as a cellulose dispersion) comprising a liquid medium and a natural cellulose material in which primary cellulose particles have an average particle size of 10 μm or larger and less than 50 μm, average width of 2-30 μm and average thickness of 0.5-5 μm, and a step of drying thus obtained cellulose dispersion.

2. The porous cellulose aggregate according to claim 1, wherein a cylinder-like molded body obtained by compressing said porous cellulose aggregates at 10 MPa has a hardness of 70-160 N and a repose angle of over 36° and less than 44°.

3. The porous cellulose aggregate according to claim 1, wherein a cylinder-like molded body obtained by compressing said porous cellulose aggregates to 10 MPa has a hardness of 60-100 N and a repose angle of 25° or above and 36° or less.

4. The porous cellulose aggregate according to claim 1, wherein said cellulose dispersion contains 10% by weight or less of particles that are not sedimented at a centrifugal condition of centrifugal force of 4900 m/s$^2$.

* * * * *